US009802919B1

(12) United States Patent
Sutton et al.

(10) Patent No.: US 9,802,919 B1
(45) Date of Patent: Oct. 31, 2017

(54) COMPOUNDS

(71) Applicant: CHIESI FARMACEUTICI S.P.A., Parma (IT)

(72) Inventors: Jonathan Mark Sutton, Harlow (GB); Robert Andrew Heald, Harlow (GB); Andrew Stephen Robert Jennings, Harlow (GB); Carmelida Capaldi, Parma (IT); Elisabetta Armani, Parma (IT)

(73) Assignee: CHIESI FARMACEUTICI S.p.A., Parma (IT)

( * ) Notice: Subject to any disclaimer, the term of this patent is extended or adjusted under 35 U.S.C. 154(b) by 0 days.

(21) Appl. No.: 15/606,313

(22) Filed: May 26, 2017

(30) Foreign Application Priority Data

May 31, 2016 (EP) .................................... 16172196

(51) Int. Cl.
| | |
|---|---|
| *C07D 403/04* | (2006.01) |
| *C07D 401/14* | (2006.01) |
| *C07D 403/14* | (2006.01) |
| *C07D 413/14* | (2006.01) |
| *C07D 471/04* | (2006.01) |
| *C07D 417/14* | (2006.01) |
| *A61K 31/4178* | (2006.01) |
| *A61K 31/4155* | (2006.01) |
| *A61K 31/4196* | (2006.01) |
| *A61K 31/454* | (2006.01) |
| *C07C 309/29* | (2006.01) |

(52) U.S. Cl.
CPC .......... *C07D 403/04* (2013.01); *C07C 309/29* (2013.01); *C07D 401/14* (2013.01); *C07D 403/14* (2013.01); *C07D 413/14* (2013.01); *C07D 417/14* (2013.01); *C07D 471/04* (2013.01)

(58) Field of Classification Search
None
See application file for complete search history.

(56) References Cited

U.S. PATENT DOCUMENTS 9,409,870 B2 * 8/2016 Armani ................ C07D 233/70
2011/0082155 A1 4/2011 Murugan et al.

FOREIGN PATENT DOCUMENTS

WO 2016/096638 6/2016

OTHER PUBLICATIONS

European Search Report in Application No. 16172196.4 dated Aug. 8, 2016.

* cited by examiner

*Primary Examiner* — Michael Barker
(74) *Attorney, Agent, or Firm* — Oblon, McClelland, Maier & Neustadt, L.L.P.

(57) ABSTRACT

Compounds of formula (I) defined herein exhibit human neutrophil elastase inhibitory properties and are useful for the treatment of disease or conditions in which HNE is implicated.

14 Claims, No Drawings

COMPOUNDS

CROSS REFERENCES TO RELATED APPLICATIONS

This application claims priority to European Patent Application No. 16172196.4, filed on May 31, 2016, which is incorporated herein by reference in its entirety.

BACKGROUND OF THE INVENTION

Field of the Invention

The present invention relates to imidazolone derivatives having exhibit human neutrophil elastase inhibitory properties, and the therapeutic use of such a derivative.

Discussion of the Background

Human neutrophil elastase (HNE) is a 32 kDa serine proteinase found in the azurophilic granules of neutrophils. It has a role in the degradation of a wide range of extracellular matrix proteins, including fibronectin, laminin, proteoglycans, Type III and Type IV collagens as well as elastin (see Bieth, G. in *Regulation of Matrix accumulation*, Mecham, R. P. (Eds), Academic Press, NY, USA 1986, 217-306, which is incorporated herein by reference in its entirety). HNE has long been considered to play an important role in homeostasis through repair and disposal of damaged tissues via degradation of the tissue structural proteins. It is also relevant in the defense against bacterial invasion by means of degradation of the bacterial body. In addition to its effects on matrix tissues, HNE has been implicated in the upregulation of IL-8 gene expression and also induces IL-8 release from the epithelial cells of the lung. In animal models of Chronic Obstructive Pulmonary Disease induced by tobacco smoke exposure both small molecule inhibitors and protein inhibitors of HNE inhibit the inflammatory response and the development of emphysema (see Wright, J. L. et al. *Am. J. Respir. Crit. Care Med.* 2002, 166, 954-960; Churg, A. et al. *Am. J. Respir. Crit. Care Med.* 2003, 168, 199-207, which are incorporated herein by reference in their entireties). Thus, HNE may play a role both in matrix destruction and in amplifying inflammatory responses in chronic respiratory diseases where neutrophil influx is a characteristic feature. Indeed, HNE is believed to play a role in several pulmonary diseases, including chronic obstructive pulmonary disease (COPD), cystic fibrosis (CF), acute respiratory distress syndrome (ARDS), pulmonary emphysema, pneumonia and lung fibrosis. It is also implicated in several cardiovascular diseases in which tissue remodeling is involved, for example, in heart failure and the generation of ischemic tissue injury following acute myocardial infarction.

COPD is an umbrella term encompassing three different pathological conditions, all of which contribute to limitation of airflow: chronic bronchitis, emphysema and small-airway disease. Generally all three will exist to varying extents in patients presenting with COPD, and all three may be due to neutrophil-mediated inflammation, as supported by the increased number of neutrophils observed in bronchoalveolar leakage (BAL) fluids of COPD patients (see Thompson, A. B.; Daughton, D.; et al. *Am. Rev. Respir. Dis.* 1989, 140, 1527-1537, which is incorporated herein by reference in its entierty). The major pathogenic determinant in COPD has long been considered to be the protease-anti-protease balance (also known as the "elastase:anti-elastase hypothesis"), in which an imbalance of HNE and endogenous antiproteases such as a1-antitrypsin ($\alpha_1$-AT), secretory leukocyte protease inhibitor (SLPI) and pre-elafin leads to the various inflammatory disorders of COPD. Individuals that have a genetic deficiency of the protease inhibitor $\alpha$1-antitrypsin develop emphysema that increases in severity over time (see Laurrell, C. B.; Erikkson, S *Scand. J. Clin. Invest.* 1963 15, 132-140, which is incorporated herein by reference in its entirety). An excess of HNE is therefore destructive, leading to the breakdown of pulmonary morphology with loss of elasticity and destruction of alveolar attachments of airways in the lung (emphysema) whilst simultaneously increasing microvascular permeability and mucus hypersecretion (chronic bronchitis).

Several human neutrophil inhibitors have been disclosed so far. In particular, WO2011/110858, WO2011/110859, WO 2014/095700, and WO 2015/091281, which are incorporated herein by reference in their entireties, describe pyrimidine derivatives having human neutrophil elastase inhibitory properties.

Although several HNE inhibitors have been disclosed so far as above reported, there is still a need for further HNE inhibitors. Particularly, there is still a need for further FINE inhibitors endowed with a high potency for FINE enzyme inhibition. Particularly advantageous would also be the identification of further FINE inhibitors endowed with a high potency for HNE enzyme inhibition and which would show an appropriate developability profile as an inhalation treatment.

SUMMARY OF THE INVENTION

Accordingly, it is one object of the present invention to provide novel imidazolone derivatives having exhibit human neutrophil elastase inhibitory properties.

It is another object of the present invention to provide novel methods of treating and/or preventing certain diseases by administering such an imidazolone derivative.

These and other objects, which will become apparent during the following detailed description, have been achieved by the inventors' discovery of the compounds of formula (I) described below.

Thus, in one aspect, the present invention provides a compound of formula (I), or a pharmaceutically acceptable salt thereof:

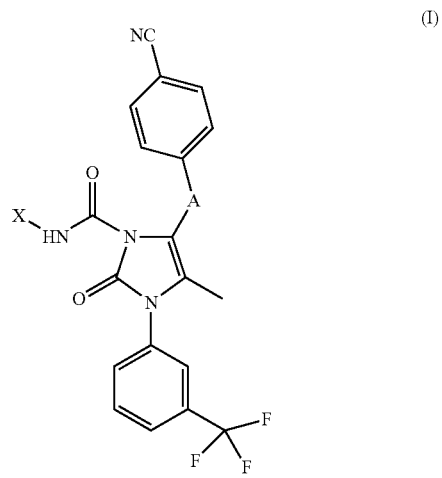

wherein
A is selected from the group consisting of

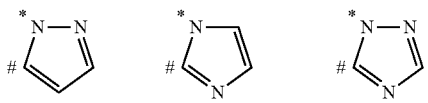

X is selected from the group consisting of

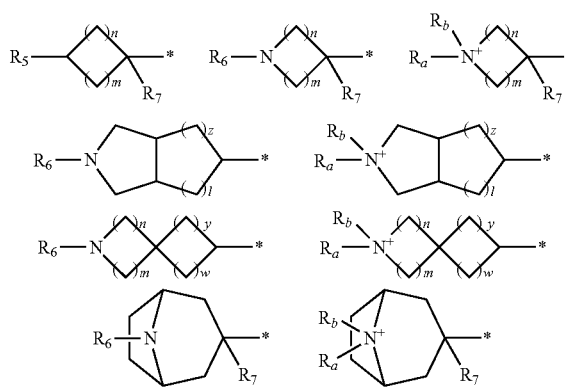

or is selected from the group consisting of

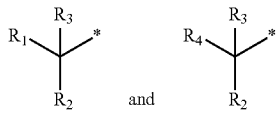

$R_1$ is selected from the group consisting of

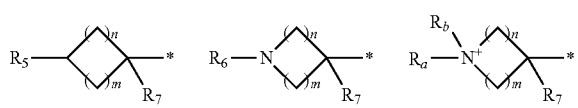

n is an integer from 1 to 4;
m is 0 or an integer from 1 to 4;
t is 0 or an integer from 1 to 4;
y is an integer from 1 to 4;
w is an integer from 1 to 4;
z is 0 or 1;
l is 0 or 1;
$R_2$ is —H or linear or branched —($C_1$-$C_4$)alkyl;
$R_3$ is linear or branched —($C_1$-$C_4$)alkyl or $R_2$ and $R_3$ may form together a cycloalkyl;
$R_4$ is selected from the group consisting of -arylene-($C_1$-$C_4$)alkylene-$NR_dR_e$, -arylene-($C_1$-$C_4$)alkylene-$N^+R_aR_bR_c$, -heteroarylene-($C_1$-$C_4$)alkylene-$NR_dR_e$, -heteroarylene-($C_1$-$C_4$)alkylene-$N^+R_aR_bR_c$ and heteroaryl, wherein any of such arylene-($C_1$-$C_4$)alkylene-$NR_dR_e$, -arylene-($C_1$-$C_4$)alkylene-$N^+R_aR_bR_c$, -heteroarylene-($C_1$-$C_4$)alkylene-$NR_dR_e$, -heteroarylene-($C_1$-$C_4$)alkylene-$N^+R_aR_bR_c$ and heteroaryl may be optionally substituted by one or more —($C_1$-$C_4$)alkyl or $R_4$ is selected from the group consisting of

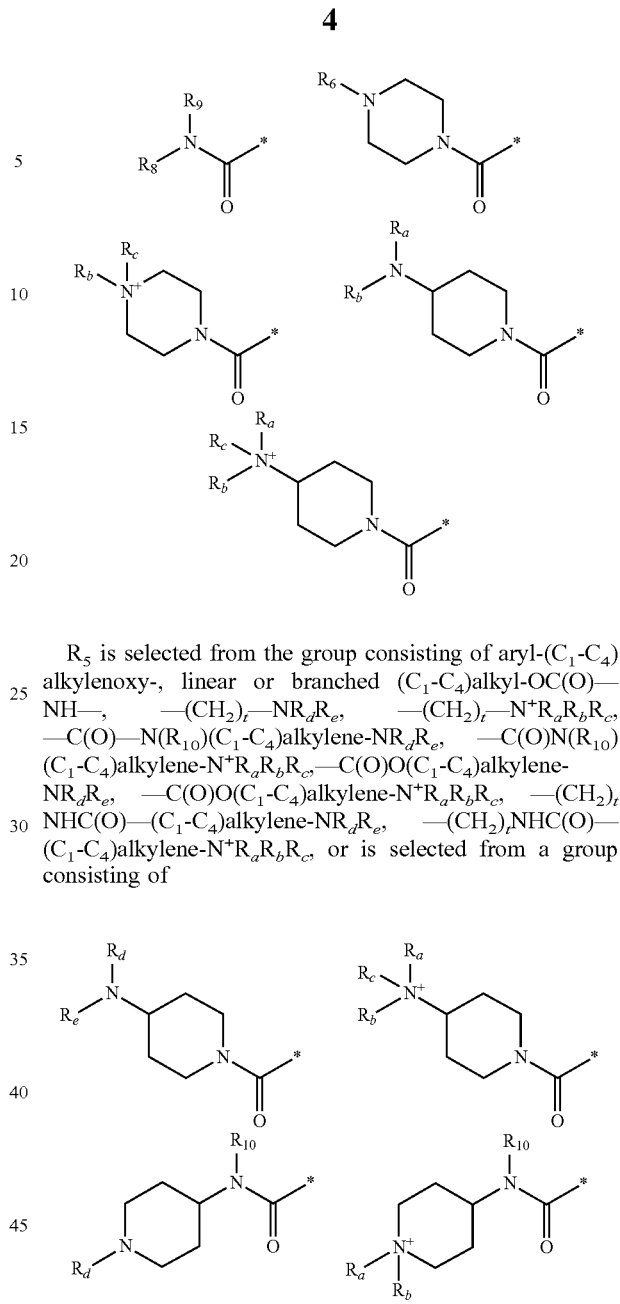

$R_5$ is selected from the group consisting of aryl-($C_1$-$C_4$)alkylenoxy-, linear or branched ($C_1$-$C_4$)alkyl-OC(O)—NH—, —($CH_2$)$_t$—$NR_dR_e$, —($CH_2$)$_t$—$N^+R_aR_bR_c$, —C(O)—N($R_{10}$)($C_1$-$C_4$)alkylene-$NR_dR_e$, —C(O)N($R_{10}$)($C_1$-$C_4$)alkylene-$N^+R_aR_bR_c$, —C(O)O($C_1$-$C_4$)alkylene-$NR_dR_e$, —C(O)O($C_1$-$C_4$)alkylene-$N^+R_aR_bR_c$, —($CH_2$)$_t$NHC(O)—($C_1$-$C_4$)alkylene-$NR_dR_e$, —($CH_2$)$_t$NHC(O)—($C_1$-$C_4$)alkylene-$N^+R_aR_bR_c$, or is selected from a group consisting of

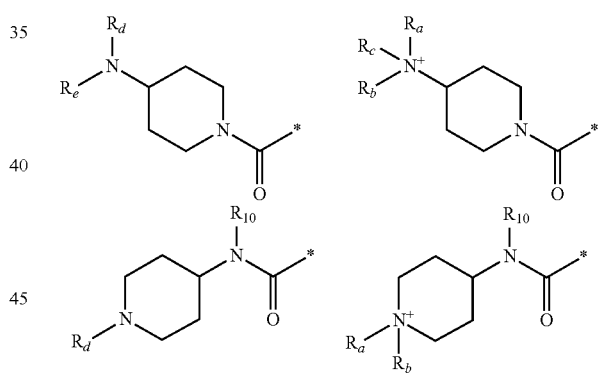

$R_6$ is selected from the group consisting of —H, —($C_1$-$C_4$)alkyl, aryl-($C_1$-$C_4$)alkylene-OCO—, $CF_3C(O)$—, aryl-($C_1$-$C_4$)alkylene, linear or branched ($C_1$-$C_4$)alkyl-OC(O)—, —C(O)—($C_1$-$C_4$)alkylene-$NRA_e$, —C(O)—($C_1$-$C_4$)alkylene-$N^+R_aR_bR_c$, —C(O)O—($C_1$-$C_4$)alkylene-$NR_dR_e$, —C(O)O—($C_1$-$C_4$)alkylene-$N^+R_aR_bR_c$, —C(O)—N($R_{10}$)($C_1$-$C_4$)alkylene-$NR_dR_e$, —C(O)N($R_{10}$)($C_1$-$C_4$)alkylene-$N^+R_aR_bR_c$;
$R_a$ is —($C_1$-$C_4$)alkyl;
$R_b$ is —($C_1$-$C_4$)alkyl;
$R_c$ is selected from —($C_1$-$C_4$)alkyl, aryl-($C_1$-$C_4$)alkylene and heteroaryl-($C_1$-$C_4$)alkylene, wherein said heteroaryl-($C_1$-$C_4$)alkylene may be optionally substituted by one or more —($C_1$-$C_4$)alkyl groups;
$R_d$ is —H or —($C_1$-$C_4$)alkyl;
$R_e$ is —H or —($C_1$-$C_4$)alkyl;
$R_7$ is —H or —($C_1$-$C_4$)alkyl;
$R_8$ is —H or —($C_1$-$C_4$)alkyl;

R₉ is selected from the group consisting of heterocycloalkyl, heterocycloalkyl-(C₁-C₄)alkylene-, (C₁-C₄)alkylene-NR_aR_e and (C₁-C₄)alkylene-N⁺R_aR_bR_c;

R₁₀ is —H or —(C₁-C₄)alkyl;

wherein any of such heterocycloalkyl, aryl, heteroaryl and aryl-(C₁-C₄)alkylene may be optionally substituted by one or more groups independently selected from (C₁-C₄)alkyl and OR₇ and wherein the nitrogen atom in the heterocycloalkyl and heteroaryl groups may be quaternized.

The compounds of formula (I) can be prepared in the form of salts, particularly pharmaceutically acceptable salts, N-oxides, hydrates, solvates and polymorphs thereof. Any reference to a compound herein, or reference to "compounds of the invention", "compounds of formula (I)", and the like includes such compounds whether or not in salt, N-oxide, hydrate, solvate or polymorphic form.

The compounds of the present invention can be used in the treatment or prevention of diseases in which HNE is implicated, for example chronic obstructive pulmonary disease (COPD), bronchiectasis, chronic bronchitis, lung fibrosis, pneumonia, acute respiratory distress syndrome (ARDS), pulmonary emphysema, smoking-induced emphysema and cystic fibrosis.

Hence other aspects of the invention are (i) a pharmaceutical composition comprising a compound of the invention and a pharmaceutically acceptable carrier or excipient; and (ii) the use of a compound of the invention for the manufacture of a medicament for the treatment or prevention of a disease or condition in which HNE is implicated.

DETAILED DESCRIPTION OF THE PREFERRED EMBODIMENTS

Terminology

The term "(C_a-C_b)alkyl" wherein a and b are integers refers to a straight or branched chain alkyl radical having from a to b carbon atoms. Thus when a is 1 and b is 6, for example, the term includes methyl, ethyl, n-propyl, isopropyl, n-butyl, isobutyl, sec-butyl, t-butyl, n-pentyl and n-hexyl.

The term "(C_a-C_b) cycloalkyl", wherein a and b are integers, refers to saturated monocyclic, bicyclic or tricyclic hydrocarbon groups containing from a to b ring carbon atoms, as appropriate. Examples include cyclopropyl, cyclobutyl, cyclopentyl, cyclohexyl, cycloheptyl, and adamantyl.

The term "heterocyclic" relates to a saturated mono-, bi- or tri-cyclic non-aromatic radical containing one or more heteroatoms selected from S, N and O. In the case of bicyclic heterocyclic systems, included within the scope of the term are fused, Spiro and bridged bicyclic systems, such as for example a quinuclidine ring. In particular, the term "C_a-C_bheterocycloalkyl" refers to monocyclic (C_a-C_b)cycloalkyl groups, in which at least one ring carbon atom is replaced by a heteroatom (e.g. N, NH, S or O). Examples of (C_a-C_b) heterocycloalkyl include pyrrolidinyl, thiazolidinyl, piperazinyl, piperidinyl, morpholinyl, thiomorpholinyl.

By analogy, the expression "heterocycloalkylene" refers to a divalent heterocyclic radical as above defined. In particular, the expression "(C_a-C_b)heterocycloalkylene" refers to a divalent (C_a-C_b)heterocycloalkyl radical (such as for example pyrrolidinene) wherein "(C_a-C_b)heterocycloalkyl group is as above defined.

The expression "heteroaryl" refers to mono or bi-cyclic ring systems with 5 to 11 ring atoms, in which at least one ring is aromatic and in which at least one ring atom is a heteroatom (e.g. N, NH, S or O).

Examples of suitable 5,6-membered heteroaryl monocyclic systems include, for instance thiophene (thiophenyl), pyrrole (pyrrolyl), pyrazole (pyrazolyl), imidazole (imidazolyl), isoxazole (isoxazolyl), oxazole (oxazolyl), isothiazole (isothiazolyl), thiazole (thiazolyl), pyridine (pyridinyl), pyrimidine (pyrimidinyl), pyridazine (pyridazinyl), and furan (furanyl) radicals and the like.

Examples of suitable bi-cyclic heteroaryl ring systems include quinolones (quinolonyl), isoquinolines (isoquinolinyl), indole (indolyl), isoindole (isoindolyl), indolizine (indolizinyl), benzimidazole (benzimidazolyl), azabenzimidazole (azabenzimidazolyl), benzoxazole (benzoxazolyl), and benzothiazole (benzothiazolyl) radicals and the like.

Throughout the specification the use of an asterisk "*" and "#" in the definition of a structural formula, indicates the points of attachment for the radical groups to the rest of the molecule. In particular, the nitrogen atom indicated with * in group A is directly linked to the carbon atom of fragment

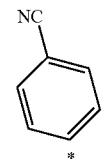

also indicated with *, and the carbon atom indicated with # in group A is directly linked to the carbon atom of fragment

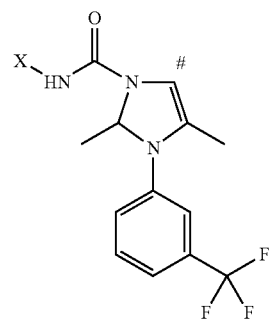

also indicated with #.

The term "pharmaceutically acceptable salts" refers to derivatives of compounds of formula (I) wherein the parent compound is modified by converting any of the free acid or basic group, if present, into the corresponding addition salt with any base or acid conventionally intended as being pharmaceutically acceptable.

Where the compounds of the invention have at least one stereogenic center, they can exist as enantiomers. When the compounds according to the invention possess two or more stereogenic centers, they can additionally exist as diastereoisomers. It is to be understood that all such isomers and mixtures thereof in any proportion are encompassed within the scope of the present invention.

It is to be understood that all preferred groups or embodiments described here below for compounds of formula (I) may be combined among each other mutatis mutandis.

In one embodiment for compounds of formula (I), A is

In another embodiment, X is selected from the group consisting of

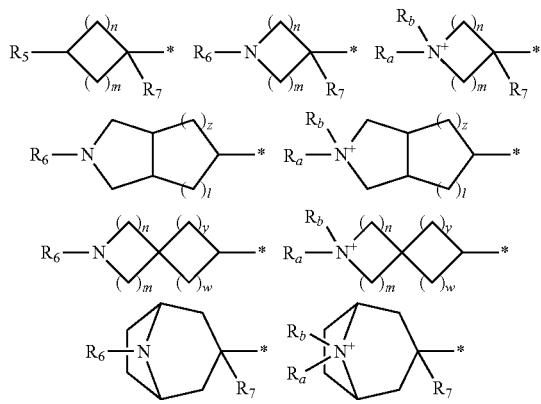

wherein n is 1, 2 or 3, m is 0, 1 or 2, z is 0 or 1, l is 0 or 1, y is 1 or 2, w is 1 or 2.

In another embodiment, X is selected from the group consisting of

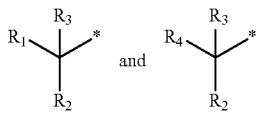

In another embodiment, $R_1$ is selected from the group consisting of

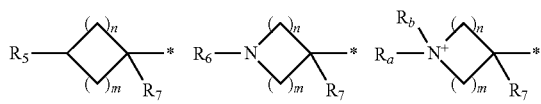

n is 1, 2 or 3; m is 0, 1 or 2.

In another embodiment, $R_2$ is —H or linear or branched —(C$_1$-C$_4$)alkyl.

In another embodiment, $R_3$ is linear or branched —(C$_1$-C$_4$)alkyl or $R_2$ and $R_3$ may form together a cycloalkyl.

In another embodiment, $R_4$ is selected from the group consisting of -arylene-(C$_1$-C$_4$)alkylene-NR$_d$R$_e$, -arylene-(C$_1$-C$_4$)alkylene-N$^+$R$_a$R$_b$R$_c$, -heteroarylene-(C$_1$-C$_4$)alkylene-NR$_d$R$_e$, -heteroarylene-(C$_1$-C$_4$)alkylene-N$^+$R$_a$R$_b$R$_c$, and heteroaryl or is selected from the group consisting of

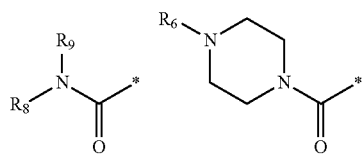

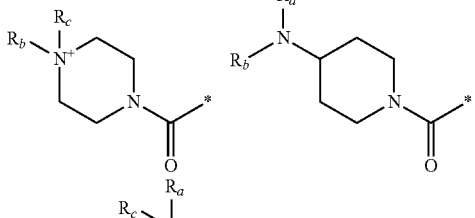

In another embodiment, $R_5$ is selected from the group consisting of aryl-(C$_1$-C$_4$)alkylenoxy-, linear or branched (C$_1$-C$_4$)alkyl-OC(O)—NH—, —(CH$_2$)$_t$—NR$_d$R$_e$, —(CH$_2$)$_t$—N$^+$R$_a$R$_b$R$_c$, —C(O)—N(R$_{10}$)(C$_1$-C$_4$)alkylene-NR$_d$R$_e$, —C(O)N(R$_{10}$)(C$_1$-C$_4$)alkylene-N$^+$R$_a$R$_b$R$_c$, —C(O)O(C$_1$-C$_4$)alkylene-NR$_d$R$_e$, —C(O)O(C$_1$-C$_4$)alkylene-N$^+$R$_a$R$_b$R$_c$, —(CH$_2$)$_t$NHC(O)—(C$_1$-C$_4$)alkylene-NR$_d$R$_e$, —(CH$_2$)$_t$NHC(O)—(C$_1$-C$_4$)alkylene-N$^+$R$_a$R$_b$R$_c$, or is selected from a group consisting of

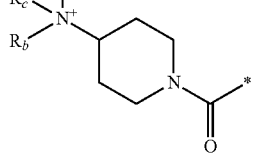

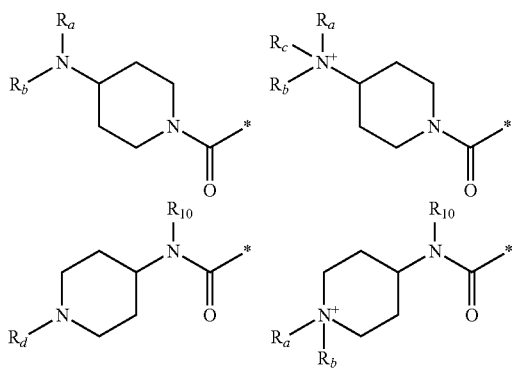

In another embodiment, $R_6$ is selected from the group consisting of —H, —(C$_1$-C$_4$)alkyl, aryl-(C$_1$-C$_4$)alkylene-OCO—, CF$_3$C(O)—, aryl-(C$_1$-C$_4$)alkylene, linear or branched (C$_1$-C$_4$)alkyl-OC(O)—, —C(O)—(C$_1$-C$_4$)alkylene-NR$_d$R$_e$, —C(O)—(C$_1$-C$_4$)alkylene-N$^+$R$_a$R$_b$R$_c$, —C(O)O—(C$_1$-C$_4$)alkylene-NR$_d$R$_e$, —C(O)O—(C$_1$-C$_4$)alkylene-N$^+$R$_a$R$_b$R$_c$, —C(O)—N(R$_{10}$)(C$_1$-C$_4$)alkylene-NR$_d$R$_e$, —C(O)N(R$_{10}$)(C$_1$-C$_4$)alkylene-N$^+$R$_a$R$_b$R$_c$.

In another embodiment, R$_a$ and R$_b$ are independently —(C$_1$-C$_4$)alkyl, R$_c$ is selected from —(C$_1$-C$_4$)alkyl, aryl-(C$_1$-C$_4$)alkylene and heteroaryl-(C$_1$-C$_4$)alkylene, wherein said heteroaryl-(C$_1$-C$_4$)alkylene may be optionally substituted by one or more —(C$_1$-C$_4$)alkyl groups.

In another embodiment, R$_d$ and R$_e$ are independently —H or —(C$_1$-C$_4$)alkyl.

In another embodiment, $R_7$ and $R_8$ are independently —H or —(C$_1$-C$_4$)alkyl; $R_9$ is selected from the group consisting of heterocycloalkyl, heterocycloalkyl-(C$_1$-C$_4$)alkylene-, (C$_1$-C$_4$)alkylene-NR$_d$R$_e$, and (C$_1$-C$_4$)alkylene-N$^+$R$_a$R$_b$R$_c$; $R_{10}$ is —H or —(C$_1$-C$_4$)alkyl.

In another embodiment, any heterocycloalkyl, aryl, heteroaryl and aryl-(C$_1$-C$_4$)alkylene may be optionally substituted by one or more groups independently selected from $(C_1-C_4)$alkyl and $OR_7$ and wherein the nitrogen atom in the heterocycloalkyl and heteroaryl groups may be quaternized.

In another embodiment, A is

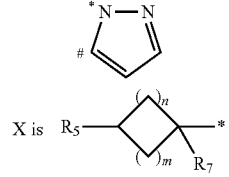

n is 2 or 3; m is 0 or 2; $R_7$ is —H; $R_5$ is selected from aryl-$(C_1-C_4)$alkylenoxy-, linear or branched $(C_1-C_4)$alkyl-OC(O)—NH, $C(O)O(C_1-C_4)$alkylene-$N^+R_aR_bR_c$, —$(CH_2)$NHC(O)—$(C_1-C_4)$alkylene-$NR_dR_e$, —$(CH_2)$NHC(O)—$(C_1-C_4)$alkylene-$N^+R_aR_bR_c$ and —$C(O)N(R_{10})(C_1-C_4)$alkylene-$N^+R_aR_bR_c$— wherein t is 0 or 1, $R_a$ and $R_b$ are independently —$(C_1-C_4)$alkyl, $R_c$ is selected from —$(C_1-C_4)$alkyl, heteroaryl-$(C_1-C_4)$alkylene and aryl-$(C_1-C_4)$alkylene, $R_d$ and $R_e$ are independently —$(C_1-C_4)$alkyl, $R_{10}$ is —H or —$(C_1-C_4)$alkyl.

In another embodiment, A is

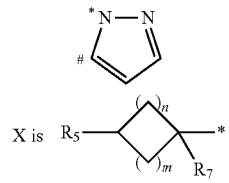

n is 1 or 2; m is 1 or 2; $R_7$ is —H; $R_5$ is selected from —$(CH_2)_t$—$NR_dR_e$, —$(CH_2)_t$—$N^+R_aR_bR_c$, wherein t is 0 or 1, $R_a$ and $R_b$ are independently —$(C_1-C_4)$alkyl, $R_c$ is selected from —$(C_1-C_4)$alkyl, heteroaryl-$(C_1-C_4)$alkylene and aryl-$(C_1-C_4)$alkylene.

In another embodiment, A is

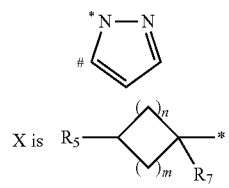

n is 2; m is 2; $R_7$ is —H; $R_5$ is

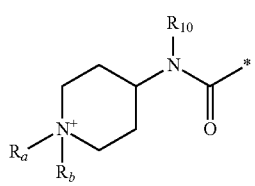

$R_a$ is —$(C_1-C_4)$alkyl; $R_b$ is —$(C_1-C_4)$alkyl; $R_{10}$ is —H or —$(C_1-C_4)$alkyl.

In another embodiment, A is

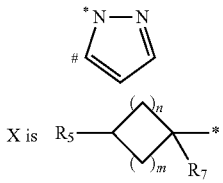

n is 2; m is 2; $R_7$ is —H; $R_5$ is

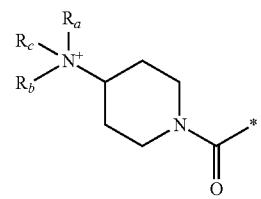

$R_a$, $R_b$ and $R_c$ are independently —$(C_1-C_4)$alkyl.

In another embodiment, A is

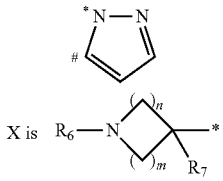

n is 2; m is 2; $R_7$ is —H or —$(C_1-C_4)$alkyl; $R_6$ is selected from aryl-$(C_1-C_4)$alkyl enoxy-,aryl-$(C_1-C_4)$alkylene-OCO—, $CF_3C(O)$—, —$C(O)$—$(C_1-C_4)$alkylene-$NR_dR_e$, —$C(O)O$—$(C_1-C_4)$alkylene-$N^+R_aR_bR_c$, —$C(O)N(R_{10})(C_1-C_4)$alkylene-$N^+R_aR_bR_c$, and —$C(O)$—$(C_1-C_4)$alkylene-$N^+R_aR_bR_c$ wherein $R_d$ is —H or —$(C_1-C_4)$alkyl; $R_e$ is —H or —$(C_1-C_4)$alkyl, $R_a$ is —$(C_1-C_4)$alkyl; $R_b$ is —$(C_1-C_4)$alkyl; $R_c$ is selected from —$(C_1-C_4)$alkyl; $R_{10}$ is —H or —$(C_1-C_4)$alkyl.

In another embodiment, A is

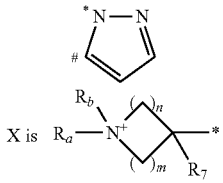

n is 1 or 2; m is 2; $R_7$ is —H or —$(C_1-C_4)$alkyl; $R_a$ and $R_b$ are independently —$(C_1-C_4)$alkyl.

In another embodiment, A is

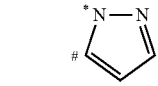

-continued

X is 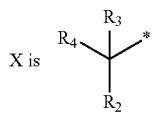

R$_2$ is —H or linear or branched —(C$_1$-C$_4$)alkyl and R$_3$ is linear or branched —(C$_1$-C$_4$)alkyl; R$_4$ is

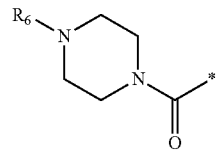

wherein R$_6$ is —(C$_1$-C$_4$)alkyl.

In another embodiment, A is

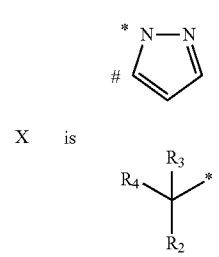

R$_2$ is —H or linear or branched —(C$_1$-C$_4$)alkyl and R$_3$ is linear or branched —(C$_1$-C$_4$)alkyl; R$_4$ is

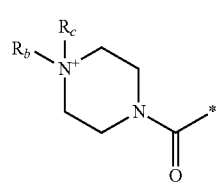

wherein R$_b$ is —(C$_1$-C$_4$)alkyl and R$_c$ is selected from —(C$_1$-C$_4$)alkyl and aryl-(C$_1$-C$_4$)alkylene.

In another embodiment, A is

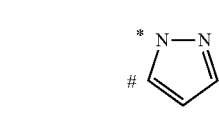

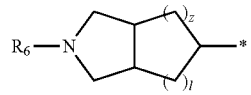

z is 0 or 1; 1 is 0 or 1; R$_6$ is aryl-(C$_1$-C$_4$)alkylene optionally substituted by one or more OR$_7$, wherein R$_7$ is —(C$_1$-C$_4$)alkyl or R$_6$ is linear or branched (C$_1$-C$_4$)alkyl-OC(O)—.

In another embodiment, A is

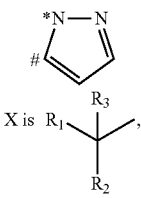

R$_2$ is —H and R$_3$ is linear or branched —(C$_1$-C$_4$)alkyl; R$_1$ is

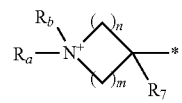

n is 1 or 2; m is 2; R$_a$ and R$_b$ are independently —(C$_1$-C$_4$)alkyl; R$_7$ is —H.

In another embodiment, A is

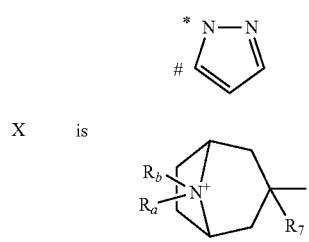

R$_a$ and R$_b$ are independently —(C$_1$-C$_4$)alkyl; R$_7$ is —H.

In another embodiment, A is

z is 0 or 1; 1 is 0 or 1; R$_a$ and R$_b$ are independently —(C$_1$-C$_4$)alkyl.

In another embodiment, A is

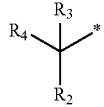

R$_2$ is —H or linear or branched —(C$_1$-C$_4$)alkyl, R$_3$ is linear or branched —(C$_1$-C$_4$)alkyl or R$_2$ and R$_3$ may form together a cycloalkyl; R$_4$ is heteroaryl optionally substituted by $(C_1-C_4)$alkyl or $R_4$ is selected from -heteroarylene-$(C_1-C_4)$alkylene-$NR_dR_e$ and -heteroarylene-$(C_1-C_4)$alkylene-$N^+R_aR_bR_c$, wherein $R_a$ is —$(C_1-C_4)$alkyl; $R_b$ is —$(C_1-C_4)$alkyl; $R_c$ is selected from —$(C_1-C_4)$alkyl, $R_d$ is —H or —$(C_1-C_4)$alkyl; $R_e$ is —H or —$(C_1-C_4)$alkyl.

In another embodiment, A is

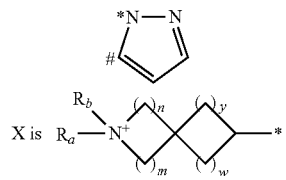

$R_a$ and $R_b$ are independently —$(C_1-C_4)$alkyl, n is 2, m is 2, y is 1 or 2 and w is 1 or 2.

In another embodiment, A is

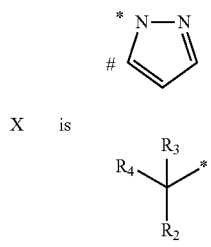

$R_2$ is —H and $R_3$ is linear or branched —$(C_1-C_4)$alkyl; $R_4$ is

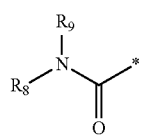

$R_8$ is —H or —$(C_1-C_4)$alkyl; $R_9$ is selected from -heterocycloalkyl and heterocycloalkyl-$(C_1-C_4)$alkylene-, wherein the heterocycloalkyl and the heterocycloalkyl-$(C_1-C_4)$alkylene- may optionally substituted by one or more $(C_1-C_4)$alkyl and wherein the nitrogen atom in the heterocycloalkyl group may be quaternized or $R_9$ is selected from —$(C_1-C_4)$alkylene-$NR_dR_e$ and —$(C_1-C_4)$alkylene-$N^+R_aR_bR_c$, wherein $R_a$ is —$(C_1-C_4)$alkyl; $R_b$ is —$(C_1-C_4)$alkyl; $R_c$ is —$(C_1-C_4)$alkyl, $R_d$ is —H or —$(C_1-C_4)$alkyl; $R_e$ is —H or —$(C_1-C_4)$alkyl.

In another embodiment, A is

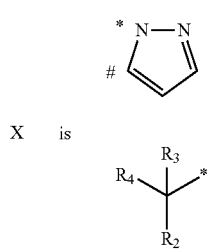

$R_2$ is —H and $R_3$ is linear or branched —$(C_1-C_4)$alkyl; $R_4$ is -arylene-$(C_1-C_4)$alkylene-$NR_dR_e$, wherein $R_d$ is —H or —$(C_1-C_4)$alkyl; $R_e$ is —H or —$(C_1-C_4)$alkyl or $R_4$ is -arylene-$(C_1-C_4)$alkylene-$N^+R_aR_bR_c$, wherein $R_a$ is —$(C_1-C_4)$alkyl; $R_b$ is —$(C_1-C_4)$alkyl; $R_c$ is —$(C_1-C_4)$alkyl.

In another embodiment, A is

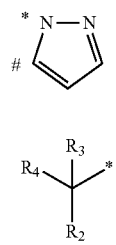

$R_2$ is —H and $R_3$ is linear or branched —$(C_1-C_4)$alkyl; $R_4$ is

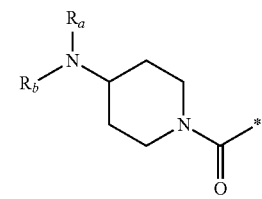

wherein $R_a$ is —$(C_1-C_4)$alkyl; $R_b$ is —$(C_1-C_4)$alkyl.

In another embodiment, A is

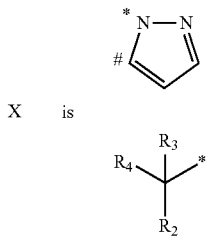

$R_2$ is —H and $R_3$ is linear or branched —$(C_1-C_4)$alkyl; $R_4$ is

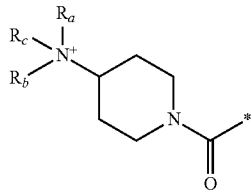

wherein $R_a$ is —$(C_1-C_4)$alkyl; $R_b$ is —$(C_1-C_4)$alkyl; $R_c$ is selected from —$(C_1-C_4)$alkyl and aryl-$(C_1-C_4)$alkylene.

In another embodiment, A is

X is

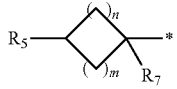

n is 2; m is 2; $R_7$ is —H; $R_5$ is —$(CH_2)_t$—$N^+R_aR_bR_c$, wherein t is 1, $R_a$ and $R_b$ are independently —$(C_1$-$C_4)$alkyl, $R_c$ is aryl-$(C_1$-$C_4)$alkylene.

In another embodiment, A is

X is

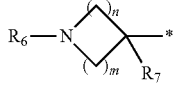

n is 2; m is 2; $R_7$ is —H, $R_6$ is selected from —C(O)—$(C_1$-$C_4)$alkylene-$NR_dR_e$, —C(O)—$(C_1$-$C_4)$alkylene-$N^+$ $R_aR_bR_c$, wherein $R_d$ is —$(C_1$-$C_4)$alkyl; $R_e$ is $(C_1$-$C_4)$alkyl, $R_a$ is —$(C_1$-$C_4)$alkyl; $R_b$ is —$(C_1$-$C_4)$alkyl; $R_c$ is selected from —$(C_1$-$C_4)$alkyl.

In another embodiment, X is selected from the group consisting of

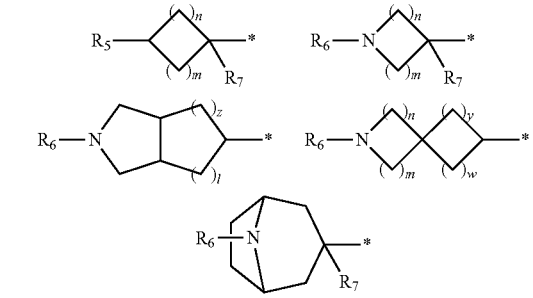

or is selected from the group consisting of

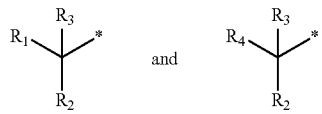

In another embodiment, a compound of the invention is selected in the group consisting of

| Example | Chemical name |
|---------|---------------|
| 1 | 5-[2-(4-Cyano-phenyl)-2H-pyrazol-3-yl]-4-methyl-2-oxo-3-(3-trifluoromethyl-phenyl)-2,3-dihydro-imidazole-1-carboxylic acid trans-(4-dimethylaminomethyl-cyclohexyl)-amide |
| 2 | 5-[2-(4-Cyano-phenyl)-2H-pyrazol-3-yl]-4-methyl-2-oxo-3-(3-trifluoromethyl-phenyl)-2,3-dihydro-imidazole-1-carboxylic acid ((1S,2S)-2-benzyloxy-cyclopentyl)-amide |
| 3 | 4-{[5-[2-(4-Cyano-phenyl)-2H-pyrazol-3-yl]-4-methyl-2-oxo-3-(3-trifluoromethyl-phenyl)-2,3-dihydro-imidazole-1-carbonyl]-amino}-piperidine-1-carboxylic acid benzyl ester |
| 4 | 5-[2-(4-Cyano-phenyl)-2H-pyrazol-3-yl]-4-methyl-2-oxo-3-(3-trifluoromethyl-phenyl)-2,3-dihydro-imidazole-1-carboxylic acid [1-(2,2,2-trifluoro-acetyp-piperidin-4-yl]-amide |
| 5 | 5-[2-(4-Cyano-phenyl)-2H-pyrazol-3-yl]-4-methyl-2-oxo-3-(3-trifluoromethyl-phenyl)-2,3-dihydro-imidazole-1-carboxylic acid ((S)-1-pyridin-4-yl-ethyl)-amide |
| 6 | 5-[2-(4-Cyano-phenyl)-2H-pyrazol-3-yl]-4-methyl-2-oxo-3-(3-trifluoromethyl-phenyl)-2,3-dihydro-imidazole-1-carboxylic acid ((R)-1-pyridin-4-yl-ethyl)-amide |
| 7 | 5-[2-(4-Cyano-phenyl)-2H-pyrazol-3-yl]-4-methyl-2-oxo-3-(3-trifluoromethyl-phenyl)-2,3-dihydro-imidazole-1-carboxylic acid [3-(4-methoxy-benzyl)-3-aza-bicyclo[3.1.0]hex-6-yl]-amide |
| 8 | (Trans-4-{[5-[2-(4-cyano-phenyl)-2H-pyrazol-3-yl]-4-methyl-2-oxo-3-(3-trifluoromethyl-phenyl)-2,3-dihydro-imidazole-1-carbonyl]-amino}}-cyclohexyl)-carbamic acid tert-butyl ester |
| 9 | 5-[2-(4-Cyano-phenyl)-2H-pyrazol-3-yl]-4-methyl-2-oxo-3-(3-trifluoromethyl-phenyl)-2,3-dihydro-imidazole-1-carboxylic acid (trans-4-dimethylamino-cyclohexyl)-amide |
| 10 | (3aS,5R,6aR)-5-{[5-[2-(4-Cyano-phenyl)-2H-pyrazol-3-yl]-4-methyl-2-oxo-3-(3-trifluoromethyl-phenyl)-2,3-dihydro-imidazole-1-carbonyl]-amino}-hexahydro-cyclopenta[c]pyrrole-2-carboxylic acid tert-butyl ester |
| 11 | 5-[2-(4-Cyano-phenyl)-2H-pyrazol-3-yl]-4-methyl-2-oxo-3-(3-trifluoromethyl-phenyl)-2,3-dihydro-imidazole-1-carboxylic acid [(S)-1-methyl-2-(4-methyl-piperazin-1-yl)-2-oxo-ethyl]-amide |
| 12 | (3aR,5S,6aS)-5-{[5-[2-(4-Cyano-phenyl)-2H-pyrazol-3-yl]-4-methyl-2-oxo-3-(3-trifluoromethyl-phenyl)-2,3-dihydro-imidazole-1-carbonyl]-amino}-hexahydro-cyclopenta[c]pyrrole-2-carboxylic acid tert-butyl ester |
| 13 | 5-[2-(4-Cyano-phenyl)-2H-pyrazol-3-yl]-4-methyl-2-oxo-3-(3-trifluoromethyl-phenyl)-2,3-dihydro-imidazole-1-carboxylic acid [(S)-1-(1-methyl-piperidin-4-ylcarbamoyl)-ethyl]-amide |

-continued

| Example | Chemical name |
|---|---|
| 14 | 5-[2-(4-Cyano-phenyl)-2H-pyrazol-3-yl]-4-methyl-2-oxo-3-(3-trifluoromethyl-phenyl)-2,3-dihydro-imidazole-1-carboxylic acid [(S)-1-(4-dimethylaminomethyl-phenyl)-ethyl]-amide |
| 15 | 5-[2-(4-Cyano-phenyl)-2H-pyrazol-3-yl]-4-methyl-2-oxo-3-(3-trifluoromethyl-phenyl)-2,3-dihydro-imidazole-1-carboxylic acid [1-(3-dimethylamino-propionyl)-piperidin-4-yl]-amide |
| 16 | 5-[2-(4-Cyano-phenyl)-2H-pyrazol-3-yl]-4-methyl-2-oxo-3-(3-trifluoromethyl-phenyl)-2,3-dihydro-imidazole-1-carboxylic acid [(S)-1-(5-dimethylaminomethyl-oxazol-2-yl)-ethyl]-amide |
| 17 | 5-[2-(4-Cyano-phenyl)-2H-pyrazol-3-yl]-4-methyl-2-oxo-3-(3-trifluoromethyl-phenyl)-2,3-dihydro-imidazole-1-carboxylic acid [1-(2-dimethylamino-acetyl)-piperidin-4-yl]-amide |
| 18 | 5-[2-(4-Cyano-phenyl)-2H-pyrazol-3-yl]-4-methyl-2-oxo-3-(3-trifluoromethyl-phenyl)-2,3-dihydro-imidazole-1-carboxylic acid {(S)-1-[methyl-(1-methyl-piperidin-4-ylmethyl)-carbamoyl]-ethyl}-amide |
| 19 | 5-[2-(4-Cyano-phenyl)-2H-pyrazol-3-yl]-4-methyl-2-oxo-3-(3-trifluoromethyl-phenyl)-2,3-dihydro-imidazole-1-carboxylic acid [(S)-2-(4-dimethylamino-piperidin-1-yl)-1-methyl-2-oxo-ethyl]-amide |
| 20 | 5-[2-(4-Cyano-phenyl)-2H-pyrazol-3-yl]-4-methyl-2-oxo-3-(3-trifluoromethyl-phenyl)-2,3-dihydro-imidazole-1-carboxylic acid {(S)-1-[(2-dimethylamino-ethyl)-methyl-carbamoyl]-ethyl}-amide |
| 21 | 5-[2-(4-Cyano-phenyl)-2H-pyrazol-3-yl]-4-methyl-2-oxo-3-(3-trifluoromethyl-phenyl)-2,3-dihydro-imidazole-1-carboxylic acid [(S)-1-(5-dimethylaminomethyl-oxazol-2-yl)-2-methyl-propyl]-amide |
| 22 | 5-[2-(4-Cyano-phenyl)-2H-pyrazol-3-yl]-4-methyl-2-oxo-3-(3-trifluoromethyl-phenyl)-2,3-dihydro-imidazole-1-carboxylic acid [(S)-1-(5-dimethylaminomethyl-oxazol-2-yl)-propyl]-amide |
| 23 | 5-[2-(4-Cyano-phenyl)-2H-pyrazol-3-yl]-4-methyl-2-oxo-3-(3-trifluoromethyl-phenyl)-2,3-dihydro-imidazole-1-carboxylic acid [[1-(5-dimethylaminomethyl-oxazol-2-yl)-cyclopropyl]-amide |
| 24 | 5-[2-(4-Cyano-phenyl)-2H-pyrazol-3-yl]-4-methyl-2-oxo-3-(3-trifluoromethyl-phenyl)-2,3-dihydro-imidazole-1-carboxylic acid [1-(5-dimethylaminomethyl-oxazol-2-yl)-1-methyl-ethyl]-amide |
| 25 | 5-[2-(4-Cyano-phenyl)-2H-pyrazol-3-yl]-4-methyl-2-oxo-3-(3-trifluoromethyl-phenyl)-2,3-dihydro-imidazole-1-carboxylic acid [1-(2-dimethylamino-acetyl)-4-methyl-piperidin-4-yl]-amide |
| 26 | 5-[2-(4-Cyano-phenyl)-2H-pyrazol-3-yl]-4-methyl-2-oxo-3-(3-trifluoromethyl-phenyl)-2,3-dihydro-imidazole-1-carboxylic acid [trans-4-(2-dimethylamino-acetylamino}-cyclohexyl]-amide |
| 27 | 5-[2-(4-Cyano-phenyl)-2H-pyrazol-3-yl]-4-methyl-2-oxo-3-(3-trifluoromethyl-phenyl)-2,3-dihydro-imidazole-1-carboxylic acid {trans-4-[(2-dimethylamino-acetylamino)-methyl]-cyclohexyl}-amide |
| 28 | 5-[2-(4-Cyano-phenyl)-2H-pyrazol-3-yl]-4-methyl-2-oxo-3-(3-trifluoromethyl-phenyl)-2,3-dihydro-imidazole-1-carboxylic acid {(S)-1-[methyl-(1-methyl-piperidin-4-yl)-carbamoyl]-ethyl}-amide |
| 29 | (Trans-4-{[5-[2-(4-cyano-phenyl)-2H-pyrazol-3-yl]-4-methyl-2-oxo-3-(3-trifluoromethyl-phenyl)-2,3-dihydro-imidazole-1-carbonyl]-amino}-cyclohexylmethyl)-trimethyl-ammonium benzene sulfonate |
| 30 | Benzyl-(trans-4-{[5-[2-(4-cyano-phenyl)-2H-pyrazol-3-yl]-4-methyl-2-oxo-3-(3-trifluoromethyl-phenyl)-2,3-dihydro-imidazole-1-carbonyl]-amino}-cyclohexylmethyl)-dimethyl-ammonium bromide |
| 31 | (Trans-4-{[5-[2-(4-cyano-phenyl)-2H-pyrazol-3-yl]-4-methyl-2-oxo-3-(3-trifluoromethyl-phenyl)-2,3-dihydro-imidazole-1-carbonyl]-amino}-cyclohexylmethyl)-ethyl-dimethyl-ammonium benzene sulfonate |
| 32 | 4-{[5-[2-(4-Cyano-phenyl)-2H-pyrazol-3-yl]-4-methyl-2-oxo-3-(3-trifluoromethyl-phenyl)-2,3-dihydro-imidazole-1-carbonyl]-amino}-1,1-dimethyl-piperidinium benzenesulfonate |
| 33 | (R)-3-{[5-[2-(4-Cyano-phenyl)-2H-pyrazol-3-yl]-4-methyl-2-oxo-3-(3-trifluoromethyl-phenyl)-2,3-dihydro-imidazole-1-carbonyl]amino}-1,1-dimethyl-pyrrolidinium benzenesulfonate |
| 34 | (S)-3-{[5-[2-(4-Cyano-phenyl)-2H-pyrazol-3-yl]-4-methyl-2-oxo-3-(3-trifluoromethyl-phenyl)-2,3-dihydro-imidazole-1-carbonyl]-amino}-1,1-dimethyl-pyrrolidinium benzenesulfonate |
| 35 | 4-(1-{[5-[2-(4-Cyano-phenyl)-2H-pyrazol-3-yl]-4-methyl-2-oxo-3-(3-trifluoromethyl-phenyl)-2,3-dihydro-imidazole-1-carbonyl]-amino}-ethyl)-1,1-dimethyl-piperidinium benzene sulfonate |
| 36 | (1S,3R,5R)-3-{[5-[2-(4-Cyano-phenyl)-2H-pyrazol-3-yl]-4-methyl-2-oxo-3-(3-trifluoromethyl-phenyl)-2,3-dihydro-imidazole-1-carbonyl]-amino}-8,8-dimethyl-8-azonia-bicyclo[3.2.1]octane benzene sulfonate |
| 37 | (3aS,5R,6aR)-5-{[5-[2-(4-Cyano-phenyl)-2H-pyrazol-3-yl]-4-methyl-2-oxo-3-(3-trifluoromethyl-phenyl)-2,3-dihydro-imidazole-1-carbonyl]-amino}-2,2-dimethyl-octahydro-cyclopenta[c]pyrrolium benzene sulfonate |
| 38 | 4-((S)-1-{[5-[2-(4-Cyano-phenyl)-2H-pyrazol-3-yl]-4-methyl-2-oxo-3-(3-trifluoromethyl-phenyl)-2,3-dihydro-imidazole-1-carbonyl]-amino}-ethyl)-1-methyl-pyridinium benzene sulfonate |

-continued

| Example | Chemical name |
|---|---|
| 39 | (1R,3S,5S)-3-{[5-[2-(4-Cyano-phenyl)-2H-pyrazol-3-yl]-4-methyl-2-oxo-3-(3-trifluoromethyl-phenyl)-2,3-dihydro-imidazole-1-carbonyl]-amino}-8,8-dimethyl-8-azonia-bicyclo[3.2.1]octane benzene sulfonate |
| 40 | 4-{5-[2-(4-Cyano-phenyl)-2H-pyrazol-3-yl]-4-methyl-2-oxo-3-(3-trifluoromethyl-phenyl)-2,3-dihydro-imidazole-1-carbonyl]-amino}-1,1-diethyl-piperidinium benzene sulfonate |
| 41 | (Trans-4-{[5-[2-(4-cyano-phenyl)-2H-pyrazol-3-yl]-4-methyl-2-oxo-3-(3-trifluoromethyl-phenyl)-2,3-dihydro-imidazole-1-carbonyl]-amino}-cyclohexyl)-trimethyl-ammonium benzene sulfonate |
| 42 | 4-((S)-1-{[5-[2-(4-Cyano-phenyl)-2H-pyrazol-3-yl]-4-methyl-2-oxo-3-(3-trifluoromethyl-phenyl)-2,3-dihydro-imidazole-1-carbonyl]-amino}-ethyl)-1-ethyl-pyridinium benzene sulfonate |
| 43 | Benzyl-(trans-4-{[5-[2-(4-cyano-phenyl)-2H-pyrazol-3-yl]-4-methyl-2-oxo-3-(3-trifluoromethyl-phenyl)-2,3-dihydro-imidazole-1-carbonyl]-amino}-cyclohexyl)-dimethyl-ammonium bromide |
| 44 | (Trans-4-{[5-[2-(4-cyano-phenyl)-2H-pyrazol-3-yl]-4-methyl-2-oxo-3-(3-trifluoromethyl-phenyl)-2,3-dihydro-imidazole-1-carbonyl]-amino}-cyclohexyl)-ethyl-dimethyl-ammonium benzene sulfonate |
| 45 | (Cis-4-{[5-[2-(4-cyano-phenyl)-2H-pyrazol-3-yl]-4-methyl-2-oxo-3-(3-trifluoromethyl-phenyl)-2,3-dihydro-imidazole-1-carbonyl]-amino}-cyclohexyl)-trimethyl-ammonium benzene sulfonate |
| 46 | Benzyl-(cis-4-{[5-[2-(4-cyano-phenyl)-2H-pyrazol-3-yl]-4-methyl-2-oxo-3-(3-trifluoromethyl-phenyl)-2,3-dihydro-imidazole-1-carbonyl]-amino}-cyclohexyl)-dimethyl-ammonium bromide |
| 47 | 4-(1-{[5-[2-(4-Cyano-phenyl)-2H-pyrazol-3-yl]-4-methyl-2-oxo-3-(3-trifluoromethyl-phenyl)-2,3-dihydro-imidazole-1-carbonyl]-amino}-1-methyl-ethyl)-1-methyl-pyridinium benzene sulfonate |
| 48 | (Cis-4-{[5-[2-(4-cyano-phenyl)-2H-pyrazol-3-yl]-4-methyl-2-oxo-3-(3-trifluoromethyl-phenyl)-2,3-dihydro-imidazole-1-carbonyl]-amino}-cyclohexyl)-ethyl-dimethyl-ammonium benzene sulfonate |
| 49 | 1-Benzyl-4-((S)-2-{[5-[2-(4-cyano-phenyl)-2H-pyrazol-3-yl]-4-methyl-2-oxo-3-(3-trifluoromethyl-phenyl)-2,3-dihydro-imidazole-1-carbonyl]-amino}-propionyl)-1-methyl-piperazin-1-ium bromide |
| 50 | 4-((S)-2-{[5-[2-(4-Cyano-phenyl)-2H-pyrazol-3-yl]-4-methyl-2-oxo-3-(3-trifluoromethyl-phenyl)-2,3-dihydro-imidazole-1-carbonyl]-amino}-propionyl)-1,1-dimethyl-piperazin-1-ium benzene sulfonate |
| 51 | 2-{[5-[2-(4-Cyano-phenyl)-2H-pyrazol-3-yl]-4-methyl-2-oxo-3-(3-trifluoromethyl-phenyl)-2,3-dihydro-imidazole-1-carbonyl]-amino}-7,7-dimethyl-7-azonia-spiro[3.5]nonane benzene sulfonate |
| 52 | 4-((R)-1-{[5-[2-(4-Cyano-phenyl)-2H-pyrazol-3-yl]-4-methyl-2-oxo-3-(3-trifluoromethyl-phenyl)-2,3-dihydro-imidazole-1-carbonyl]-amino}-ethyl)-1-methyl-pyridinium benzene sulfonate |
| 53 | (Cis-4-{[5-[2-(4-cyano-phenyl)-2H-pyrazol-3-yl]-4-methyl-2-oxo-3-(3-trifluoromethyl-phenyl)-2,3-dihydro-imidazole-1-carbonyl]-amino}-cyclohexylmethyl)-trimethyl-ammonium benzene sulfonate |
| 54 | Benzyl-(cis-4-{[5-[2-(4-cyano-phenyl)-2H-pyrazol-3-yl]-4-methyl-2-oxo-3-(3-trifluoromethyl-phenyl)-2,3-dihydro-imidazole-1-carbonyl]-amino}-cyclohexylmethyl)-dimethyl-ammonium bromide |
| 55 | (Cis-4-{[5-[2-(4-cyano-phenyl)-2H-pyrazol-3-yl]-4-methyl-2-oxo-3-(3-trifluoromethyl-phenyl)-2,3-dihydro-imidazole-1-carbonyl]-amino}-cyclohexylmethyl)-ethyl-dimethyl-ammonium benzene sulfonate |
| 56 | (3aR,5S,6aS)-5-{[5-[2-(4-Cyano-phenyl)-2H-pyrazol-3-yl]-4-methyl-2-oxo-3-(3-trifluoromethyl-phenyl)-2,3-dihydro-imidazole-1-carbonyl]-amino}-2,2-dimethyl-octahydro-cyclopenta[c]pyrrolium benzene sulfonate |
| 57 | 4-((S)-2-{[5-[2-(4-Cyano-phenyl)-2H-pyrazol-3-yl]-4-methyl-2-oxo-3-(3-trifluoromethyl-phenyl)-2,3-dihydro-imidazole-1-carbonyl]-amino}-propionylamino)-1,1-dimethyl-piperidinium benzene sulfonate |
| 58 | [4-((S)-1-{[5-[2-(4-Cyano-phenyl)-2H-pyrazol-3-yl]-4-methyl-2-oxo-3-(3-trifluoromethyl-phenyl)-2,3-dihydro-imidazole-1-carbonyl]-amino}-ethyl)-benzyl]-trimethyl-ammonium benzene sulfonate |
| 59 | [4-((S)-1-{[5-[2-(4-Cyano-phenyl)-2H-pyrazol-3-yl]-4-methyl-2-oxo-3-(3-trifluoromethyl-phenyl)-2,3-dihydro-imidazole-1-carbonyl]-amino}-ethyl)-benzyl]-trimethyl-ammonium benzene sulfonate |
| 60 | [54(S)-1-{[5-[2-(4-Cyano-phenyl)-2H-pyrazol-3-yl]-4-methyl-2-oxo-3-(3-trifluoromethyl-phenyl)-2,3-dihydro-imidazole-1-carbonyl]-amino}-ethyl)-[1,2,4]oxadiazol-3-ylmethyl]-trimethyl-ammonium benzene sulfonate |
| 61 | [2-(4-{[5-[2-(4-Cyano-phenyl)-2H-pyrazol-3-yl]-4-methyl-2-oxo-3-(3-trifluoromethyl-phenyl)-2,3-dihydro-imidazole-1-carbonyl]-amino}-piperidin-1-yl)-2-oxo-ethyl]-trimethyl-ammonium benzene sulfonate |
| 62 | 4-1[((S)-2-{[5-[2-(4-Cyano-phenyl)-2H-pyrazol-3-yl]-4-methyl-2-oxo-3-(3-trifluoromethyl-phenyl)-2,3-dihydro-imidazole-1-carbonyl]-amino}-propionyl)-methyl-amino]-methyl}-1,1-dimethyl-piperidinium benzene sulfonate |
| 63 | [5-((S)-1-{[5-[2-(4-Cyano-phenyl)-2H-pyrazol-3-yl]-4-methyl-2-oxo-3-(3-trifluoromethyl-phenyl)-2,3-dihydro-imidazole-1-carbonyl]-amino}-ethyl)-[1,3,4]oxadiazol-2-ylmethyl]-trimethyl-ammonium benzene sulfonate |

-continued

| Example | Chemical name |
|---|---|
| 64 | [2-((S)-1-{[5-[2-(4-Cyano-phenyl)-2H-pyrazol-3-yl]-4-methyl-2-oxo-3-(3-trifluoromethyl-phenyl)-2,3-dihydro-imidazole-1-carbonyl]-amino}-ethyl)-oxazol-5-ylmethyl]-trimethyl-ammonium benzene sulfonate |
| 65 | [3-(4-{[5-[2-(4-Cyano-phenyl)-2H-pyrazol-3-yl]-4-methyl-2-oxo-3-(3-trifluoromethyl-phenyl)-2,3-dihydro-imidazole-1-carbonyl]-amino}-piperidin-1-yl)-3-oxo-propyl]-trimethyl-ammonium benzene sulfonate |
| 66 | 9-{[5-[2-(4-Cyano-phenyl)-2H-pyrazol-3-yl]-4-methyl-2-oxo-3-(3-trifluoromethyl-phenyl)-2,3-dihydro-imidazole-1-carbonyl]-amino}-3,3-dimethyl-3-azonia-spiro[5.5]undecane benzene sulfonate |
| 67 | (Cis-3-{[5-[2-(4-cyano-phenyl)-2H-pyrazol-3-yl]-4-methyl-2-oxo-3-(3-trifluoromethyl-phenyl)-2,3-dihydro-imidazole-1-carbonyl]-amino}-cyclobutylmethyl)-trimethyl-ammonium benzene sulfonate |
| 68 | (Trans-3-{[5-[2-(4-cyano-phenyl)-2H-pyrazol-3-yl]-4-methyl-2-oxo-3-(3-trifluoromethyl-phenyl)-2,3-dihydro-imidazole-1-carbonyl]-amino}-cyclobutylmethyl)-trimethyl-ammonium benzene sulfonate |
| 69 | [1-((S)-2-{[5-[2-(4-Cyano-phenyl)-2H-pyrazol-3-yl]-4-methyl-2-oxo-3-(3-trifluoromethyl-phenyl)-2,3-dihydro-imidazole-1-carbonyl]-amino}-propionyl)-piperidin-4-yl]-trimethyl-ammonium benzene sulfonate |
| 70 | Benzyl-[1-((S)-2-{[5-[2-(4-cyano-phenyl)-2H-pyrazol-3-yl]-4-methyl-2-oxo-3-(3-trifluoromethyl-phenyl)-2,3-dihydro-imidazole-1-carbonyl]-amino}-propionyl)-piperidin-4-yl]-dimethyl-ammonium bromide |
| 71 | {2-[((S)-2-{[5-[2-(4-Cyano-phenyl)-2H-pyrazol-3-yl]-4-methyl-2-oxo-3-(3-trifluoromethyl-phenyl)-2,3-dihydro-imidazole-1-carbonyl]-amino}-propionyl)-methyl-amino]-ethyl}-trimethyl-ammonium benzene sulfonate |
| 72 | (Trans-4-{[5-[2-(4-cyano-phenyl)-2H-pyrazol-3-yl]-4-methyl-2-oxo-3-(3-trifluoromethyl-phenyl)-2,3-dihydro-imidazole-1-carbonyl]-amino}-cyclohexyl)-dimethyl-[1,2,4]oxadiazol-3-ylmethyl-ammonium chloride |
| 73 | [2-((S)-1-{[5-[2-(4-Cyano-phenyl)-2H-pyrazol-3-yl]-4-methyl-2-oxo-3-(3-trifluoromethyl-phenyl)-2,3-dihydro-imidazole-1-carbonyl]amino}-2-methyl-propyl)-oxazol-5-ylmethyl]-trimethyl-ammonium benzene sulfonate |
| 74 | [2-((S)-1-{[5-[2-(4-Cyano-phenyl)-2H-pyrazol-3-yl]-4-methyl-2-oxo-3-(3-trifluoromethyl-phenyl)-2,3-dihydro-imidazole-1-carbonyl]-amino}-propyl)-oxazol-5-ylmethylI-trimethyl-ammonium benzene sulfonate |
| 75 | (4-{[5-[2-(4-Cyano-phenyl)-2H-pyrazol-3-yl]-4-methyl-2-oxo-3-(3-trifluoromethyl-phenyl)-2,3-dihydro-imidazole-1-carbonyl]amino}-cyclohexyl)-dimethyl-(5-methyl-isoxazol-3-ylmethyl)-ammonium chloride |
| 76 | (4-{[5-[2-(4-Cyano-phenyl)-2H-pyrazol-3-yl]-4-methyl-2-oxo-3-(3-trifluoromethyl-phenyl)-2,3-dihydro-imidazole-1-carbonyl]-amino}-cyclohexyl)-(2,5-dimethyl-2H-pyrazol-3-ylmethyl)-dimethyl-ammonium chloride |
| 77 | {2-[(Trans-4-{[5-[2-(4-cyano-phenyl)-2H-pyrazol-3-yl]-4-methyl-2-oxo-3-(3-trifluoromethyl-phenyl)-2,3-dihydro-imidazole-1-carbonyl]-amino}-cyclohexanecarbonyl)-amino]-ethyl}-trimethyl-ammonium benzene sulfonate |
| 78 | [2-(1-{[5-[2-(4-Cyano-phenyl)-2H-pyrazol-3-yl]-4-methyl-2-oxo-3-(3-trifluoromethyl-phenyl)-2,3-dihydro-imidazole-1-carbonyl]-amino}-1-methyl-ethyl)-oxazol-5-ylmethyl]-trimethyl-ammonium benzene sulfonate |
| 79 | [2-(1-{[5-[2-(4-Cyano-phenyl)-2H-pyrazol-3-yl]-4-methyl-2-oxo-3-(3-trifluoromethyl-phenyl)-2,3-dihydro-imidazole-1-carbonyl]-amino}-cyclopropyl)-oxazol-5-ylmethyThtrimethyl-ammonium benzene sulfonate |
| 80 | {2-[(Cis-4-{[5-[2-(4-cyano-phenyl)-214-pyrazol-3-yl]-4-methyl-2-oxo-3-(3-trifluoromethyl-phenyl)-2,3-dihydro-imidazole-1-carbonyl]-amino}-cyclohexanecarbonyl)-amino]-ethyl}-trimethyl-ammonium benzene sulfonate |
| 81 | {2-[(Cis-3-{[5-[2-(4-cyano-phenyl)-2H-pyrazol-3-yl]-4-methyl-2-oxo-3-(3-trifluoromethyl-phenyl)-2,3-dihydro-imidazole-1-carbonyl]-amino}-cyclobutanecarbonyl)-amino]-ethyl}-trimethyl-ammonium benzene sulfonate |
| 82 | [2-(Trans-4-{[5-[2-(4-cyano-phenyl)-2H-pyrazol-3-yl]-4-methyl-2-oxo-3-(3-trifluoromethyl-phenyl)-2,3-dihydro-imidazole-1-carbonyl]-amino}-cyclohexaneearbonyloxy)-ethyl]-trimethyl-ammonium benzene sulfonate |
| 83 | {2-[(Trans-3-{[5-[2-(4-cyano-phenyl)-2H-pyrazol-3-yl]-4-methyl-2-oxo-3-(3-trifluoromethyl-phenyl)-2,3-dihydro-imidazole-1-carbonyl]-amino}-cyclobutanecarbonyl)-amino]-ethyl}-trimethyl-ammonium benzene sulfonate |
| 84 | [2-(4-{[5-[2-(4-Cyano-phenyl)-2H-pyrazol-3-yl]-4-methyl-2-oxo-3-(3-trifluoromethyl-phenyl)-2,3-dihydro-imidazole-1-carbonyl]-amino}-4-methyl-piperidin-1-yl)-2-oxo-ethyl]trimethyl-ammonium benzene sulfonate |
| 85 | ±[2-(1-{[5-[2-(4-Cyano-phenyl)-2H-pyrazol-3-yl]-4-methyl-2-oxo-3-(3-trifluoromethyl-phenyl)-2,3-dihydro-imidazole-1-carbonyl]-amino}-ethyl)-thiazol-4-ylmethyl]-trimethyl-ammonium benzene sulfonate |
| 86 | {[(Trans-4-{[5-[2-(4-cyano-phenyl)-2H-pyrazol-3-yl]-4-methyl-2-oxo-3-(3-trifluoromethyl-phenyl)-2,3-dihydro-imidazole-1-carbonyl]-amino}-cyclohexylmethyl)-carbamoyl]-methyl}-trimethyl-ammonium benzene sulfonate |

| Example | Chemical name |
|---|---|
| 87 | [(Trans-4-{5-[2-(4-cyano-phenyl)-2H-pyrazol-3-yl]-4-methyl-2-oxo-3-(3-trifluoromethyl-phenyl)-2,3-dihydro-imidazole-1-carbonyl]-amino}-cyclohexylcarbamoyl)-methyl]-trimethyl-ammonium benzene sulfonate |
| 88 | [1-(Trans-4-{5-[2-(4-cyano-phenyl)-2H-pyrazol-3-yl]-4-methyl-2-oxo-3-(3-trifluoromethyl-phenyl)-2,3-dihydro-imidazole-1-carbonyl]-amino}-cyclohexanecarbonyl)-piperidin-4-yl]-trimethyl-ammonium benzene sulfonate |
| 89 | {2-[(Trans-4-{5-[2-(4-cyano-phenyl)-2H-pyrazol-3-yl]-4-methyl-2-oxo-3-(3-trifluoromethyl-phenyl)-2,3-dihydro-imidazole-1-carbonyl]-amino}-cyclohexanecarbonyl)-methyl-amino]-ethyl}-trimethyl-ammonium benzene sulfonate |
| 90 | 4-[(Trans-4-{5-[2-(4-cyano-phenyl)-2H-pyrazol-3-yl]-4-methyl-2-oxo-3-(3-trifluoromethyl-phenyl)-2,3-dihydro-imidazole-1-carbonyl]-amino}-cyclohexanecarbonyl)-amino]-1,1-dimethyl-piperidinium benzene sulfonate |
| 91 | 4-[((S)-2-{5-[2-(4-Cyano-phenyl)-2H-pyrazol-3-yl]-4-methyl-2-oxo-3-(3-trifluoromethyl-phenyl)-2,3-dihydro-imidazole-1-carbonyl]-amino}-propionyl)-methyl-amino]-1,1-dimethyl-piperidinium benzene sulfonate |
| 92 | {2-[(4-{5-[2-(4-Cyano-phenyl)-2H-pyrazol-3-yl]-4-methyl-2-oxo-3-(3-trifluoromethyl-phenyl)-2,3-dihydro-imidazole-1-carbonyl]-amino}-piperidine-1-carbonyl)-amino]-ethyl}-trimethyl-ammonium benzene sulfonate |
| 93 | [2-(4-{5-[2-(4-Cyano-phenyl)-2H-pyrazol-3-yl]-4-methyl-2-oxo-3-(3-trifluoromethyl-phenyl)-2,3-dihydro-imidazole-1-carbonyl]-amino}-piperidine-1-carbonyloxy)-ethyl]-trimethyl-ammonium benzene sulfonate |
| 94 | [2-(4-{[1-(4-Cyano-phenyl)-5'-methyl-2'-oxo-1'-(3-trifluoromethyl-phenyl)-1',2'-dihydro-1H-[2,4']biimidazolyl-3'-carbonyl]-amino}-piperidin-1-yl)-2-oxo-ethyl]-trimethyl-ammonium benzene sulfonate |

The therapeutic utility of the present compounds is pertinent to any disease that is known to be at least partially mediated by the action of human neutrophil elastase. For example, the present compounds can be beneficial in the treatment of chronic obstructive pulmonary disease (COPD), cystic fibrosis (CF), bronchiectasis, acute respiratory distress syndrome (ARDS), pulmonary emphysema, pneumonia and lung fibrosis.

Compounds of the present invention are useful for treatment of inflammatory respiratory disorders, for example asthma (mild, moderate or severe), steroid resistant asthma, bronchitis, chronic obstructive pulmonary disease (COPD), cystic fibrosis (CF), pulmonary edema, pulmonary embolism, pneumonia, pulmonary sarcoidosis, pulmonary emphysema, silicosis, pulmonary fibrosis, pulmonary hypertension, respiratory failure, acute respiratory distress syndrome (ARDS), emphysema, chronic bronchitis, tuberculosis, aspergillosis and other fungal infections, hypersensitivity pneumonitis, vasculitic and thrombotic disorders of the lung vasculature, antitussive activity including treatment of chronic cough associated with inflammatory and secretory conditions of the airways, infection due to respiratory syncytial virus, influenza, coronavirus (including severe acute respiratory syndrome, SARS) and adenovirus, bronchiectasis and lung cancer.

The present invention is also concerned with pharmaceutical formulations comprising, as an active ingredient, a compound of the invention. Other compounds can be combined with compounds of this invention for the prevention and treatment of inflammatory diseases of the lung. Thus, the present invention is also concerned with pharmaceutical compositions for preventing and treating inflammatory diseases of the lung comprising a therapeutically effective amount of a compound of the invention and one or more other therapeutic agents.

Suitable therapeutic agents for a combination therapy with compounds of the invention include: (1) a corticosteroid, for example budesonide, beclomethasone, beclomethasone (e.g., as the mono or the dipropionate ester), flunisolide, fluticasone (e.g. as the propionate or furoate ester), Ciclesonide, mometasone (e.g. as the furoate ester), mometasone desonide, rofleponide, hydrocortisone, prednisone, prednisolone, methyl prednisolone, naflocort, deflazacort, halopredone acetate, fluocinolone acetonide, fluocinonide, clocortolone, tipredane, prednicarbate, alclometasone dipropionate, halometasone, rimexolone, deprodone propionate, triameinolone, betamethasone, fludrocortisone, desoxycorticosterone, rofleponide, etiprednol dicloacetate and the like. Steroid drugs can additionally include steroids in clinical or pre-clinical development for respiratory diseases such as GW-685698, GW-799943, GSK 870086, QAE397, NCX-1010, NCX-1020, NO-dexamethasone, PL-2146, NS-126 (formerly ST-126). Steroid drugs can also additionally include next generation molecules in development with reduced side effect profiles such as selective glucocorticoid receptor agonists (SEGRAs), including ZK-216348 and AZD5423; (2) a β2-adrenoreceptor agonist, such as albuterol, bambuterol, terbutaline, fenoterol, formoterol, formoterol fumarate, salmeterol, salmeterol xinafoate, arformoterol, arfomoterol tartrate, indacaterol (QAB-149), carmoterol, BI 1744 CL, GSK159797 (milveterol), GSK59790, GSK159802, GSK642444 (vilanterol), GSK678007, GSK96108, clenbuterol, procaterol, bitolterol, LAS100977 (abediterol), BI1744CL (olodaterol) and brodxaterol; (3) a leukotriene modulator, for example montelukast, zafirlukast or pranlukast; (4) anticholinergic agents, for example selective muscarinic-3 (M3) receptor antagonists such as ipratropium bromide, tiotropium, tiotropium bromide (Spiriva®), glycopyrronium bromide, aclidinium bromide, LAS34273, GSK656398, GSK233705, GSK 573719 (umeclidinium), LAS35201, QAT370 and oxytropium bromide; (5) phosphodiesterase-IV (PDE-IV) inhibitors, for example roflumilast, cilomilast or theophylline; (6) an antitussive agent, such as codeine or dextramorphan; and (7) a non-steroidal anti-inflammatory agent (NSAID), for example ibuprofen or ketoprofen; (8) a mucolytic, for example N acetyl cysteine or fudostein; (9) an expectorant/mucokinetic modulator, for example ambroxol, hypertonic solutions (e.g. saline or mannitol) or surfactant; (10) a peptide mucolytic, for example recombinant human deoxyribonuclease I (dornase-alfa and rhDNase) or helicidin; (11) antibiotics, for example azithromycin, tobramycin and aztreonam; and (12) p38 Mitogen Activated Protein (MAP) kinase inhibitors, such as GSK 856553 and GSK 681323; (13) inhibitors of Janus Kinases (JAK) such as CP-690550 or GLPG0634; (14) Spleen Tyrosine Kinase (SYK) inhibitors such as R406, R343 or PRT062607; (15) inhibitors of delta and/or gamma isoforms of Phosphatidylinositol 3-kinase (PI3K).; (16) anti-retroviral agents such as ribavirin, zanamivir or laninamivir; (17) PPAR-γ agonists such as pioglitazone and rosiglitazone.

In one aspect, the invention concerns the use of inhaled administration of compounds of the invention in combination with other anti-inflammatory drugs and bronchodilator drug combinations (i.e. triple combination product), including but not limited to salmeterol xinafoate/fluticasone propionate (Advair/Seretide®), vilanterol/fluticasone furoate (BREO ELLIPTA™), formoterol fumarate/budesonide (Symbicort®), formoterol fumarate/mometasone furoate, formoterol fumarate/beclometasone dipropionate (Foster®), formoterol fumarate/fluticasone propionate (FlutiForm®), Indacaterol/mometasone furoate, Indacaterol/QAE-397, GSK159797/GSK 685698, G5K159802/GSK 685698, GSK642444/GSK 685698, formoterol fumarate/ciclesonide, arformoterol tartrate/ciclesonide.

In another aspect, the invention concerns the use of inhaled administration of compounds of the invention in combination with other bronchodilator drug combinations, particularly $\beta_2$ agonist/$M_3$ antagonist combinations (i.e. triple combination product), including but not limited to salmeterol xinafoate/tiotropium bromide, formoterol fumarate/tiotropium bromide, formoterol fumarate/glycopyrrolate (PT003), BI 1744 CL/tiotropium bromide, indacaterol/NVA237, indacaterol/QAT-370, formoterol/LAS34273, umeclidinium/vilanterol (Anoro™), GSK159797/GSK 573719, GSK159802/GSK 573719, GSK642444/GSK 573719, GSK159797/GSK 233705, GSK159802/GSK 233705, GSK642444/GSK 233705.

The weight ratio of the first and second active ingredients can be varied and will depend upon the effective dose of each ingredient. Generally, an effective dose of each will be used.

The magnitude of prophylactic or therapeutic dose of a compound of the invention will, of course, vary with the nature of the severity of the condition to be treated and with the particular compound and its route of administration, and will generally be determined by clinical trial as required in the pharmaceutical art. It will also vary according to the age, weight and response of the individual patient. In general, the daily dose range will lie within the range of from about 0.001 mg to about 100 mg per kg body weight of a mammal, preferably 0.01 mg to about 50 mg per kg, and most preferably 0.1 to 10 mg per kg, in single or divided doses. On the other hand, it can be necessary to use dosages outside these limits in some cases.

Another aspect of the present invention concerns pharmaceutical compositions which comprise a compound of the invention and a pharmaceutically acceptable carrier. The pharmaceutical compositions of the present invention comprise a compound of the present invention as an active ingredient or a pharmaceutically acceptable salt thereof, and can also contain a pharmaceutically acceptable carrier and optionally other therapeutic ingredients.

Any suitable route of administration can be employed for providing a mammal, especially a human, with an effective dosage of a compound of the invention. In therapeutic use, the active compound can be administered by any convenient, suitable or effective route. Suitable routes of administration are known, and include oral, intravenous, rectal, parenteral, topical, ocular, nasal, buccal and pulmonary (by inhalation).

Compositions suitable for administration by inhalation are known, and can include carriers and/or diluents that are known for use in such compositions. The composition can contain 0.01-99% by weight of active compound. Preferably, a unit dose comprises the active compound in an amount of 1 µg to 10 mg.

The most suitable dosage level can be determined by any known suitable method. It will be understood, however, that the specific amount for any particular patient will depend upon a variety of factors, including the activity of the specific compound that is used, the age, body weight, diet, general health and sex of the patient, time of administration, the route of administration, the rate of excretion, the use of any other drugs, and the severity of the disease to be treated.

For delivery by inhalation, the active compound is preferably in the form of microparticles. They can be prepared by a variety of techniques, including spray-drying, freeze-drying and micronization.

By way of example, a composition of the invention can be prepared as a suspension for delivery from a nebuliser or as an aerosol in a liquid propellant, for example for use in a pressurised metered dose inhaler (PMDI). Propellants suitable for use in a PMDI are known and include CFC-12, HFA-134a, HFA-227, HCFC-22 (CCl2F2) and HFA-152 (CH4F2 and isobutane).

In a preferred embodiment, a composition is in dry powder form, for delivery using a dry powder inhaler (DPI). Many types of DPI are known.

Microparticles for delivery by administration can be formulated with excipients that aid delivery and release. For example, in a dry powder formulation, microparticles can be formulated with large carrier particles that aid flow from the DPI into the lung. Suitable carrier particles are known, and include lactose particles; they can have a mass median aerodynamic diameter of greater than 90 µm.

In the case of an aerosol-based formulation, a preferred composition is:

| | |
|---|---|
| Compound of the invention | 24 mg/canister |
| Lecithin, NF Liq. Conc. | 1.2 mg/canister |
| Trichlorofluoromethane, NF | 4.025 g/canister |
| Dichlorodifluoromethane, NF | 12.15 g/canister. |

The compounds of the present invention can be used in combination with other drugs that are used in the treatment/prevention/suppression or amelioration of the diseases or conditions for which present compounds are useful. Such other drugs can be administered, by a route and in an amount commonly used therefore, contemporaneously or sequentially with a compound of the invention. When a compound of the invention is used contemporaneously with one or more other drugs, a pharmaceutical composition containing such other drugs in addition to the compound of the invention is preferred. Accordingly, the pharmaceutical compositions of the invention include those that also contain one or more other active ingredients, in addition to a compound of the invention.

The agents of the present invention can be administered in inhaled form. Aerosol generation can be carried out using, for example, pressure-driven jet atomizers or ultrasonic atomizers, preferably using propellant-driven metered aerosols or propellant-free administration of micronized active compounds from, for example, inhalation capsules or other "dry powder" delivery systems.

The active compounds can be dosed as described depending on the inhaler system used. In addition to the active compounds, the administration forms can additionally contain excipients, such as, for example, propellants (e.g. Frigen in the case of metered aerosols), surface-active substances, emulsifiers, stabilizers, preservatives, flavorings, fillers (e.g. lactose in the case of powder inhalers) or, if appropriate, further active compounds.

For the purposes of inhalation, a large number of systems are available with which aerosols of optimum particle size can be generated and administered, using an inhalation technique which is appropriate for the patient. In addition to the use of adaptors (spacers, expanders) and pear-shaped containers (e.g. Nebulator®, Volumatic®), and automatic devices emitting a puffer spray (Autohaler®), for metered aerosols, in particular in the case of powder inhalers, a number of technical solutions are available (e.g. Diskhaler®, Rotadisk®, Turbohaler® or the inhalers for example as described EP-A-0505321).

Procedure for the Preparation of Compounds of Formula (I)

The present invention further provides a process for the preparation of a compound of formula (I) or a pharmaceutically acceptable salt or quaternary salt thereof as defined above. Compounds of the invention (I) may be prepared according to routes illustrated below in Scheme A.

The skilled person may introduce, where appropriate, suitable variations to the conditions specifically described in the experimental in order to adapt the synthetic routes to the provision of further compounds of the invention. Such variations may include, but are not limited to, use of appropriate starting materials to generate different compounds, changes in the solvent and temperature of reactions, replacements of reagents with analogous chemical role, introduction or removal of protection/deprotection stages of functional groups sensitive to reaction conditions and reagents.

Also, introduction or removal of specific synthetic steps oriented to further functionalization of the chemical scaffold may be contemplated and is included within the scope of the present invention. Processes which can be used and are described and reported in the Examples and Schemes, should not be viewed as limiting the scope of the synthetic methods available for the preparation of the compounds of the invention.

Compounds used as starting materials or intermediates may be commercially available, their preparation may be specifically described in the literature or they may be prepared according to known methods. In some instances, procedures for the preparation of intermediates or starting materials may be also provided in the experimental.

The process described is particularly advantageous as it is susceptible of being properly modulated, through any known proper variant, so as to obtain any of the desired compounds of the invention. Such variants are comprised within the scope of the present invention.

From all of the above, it should be clear that any of the described groups may be present as such or in any properly protected form.

In particular, functional groups present in the intermediate and compounds and which could generate unwanted side reaction and by-products, need to be properly protected before the alkylation, acylation, coupling or sulfonylation takes place. Likewise, subsequent deprotection of those same protected groups may follow upon completion of the said reactions.

In the present invention, unless otherwise indicated, the term "protecting group" designates a protective group adapted to preserve the function of the group it is bound to. Typically, protective groups are used to preserve amino, hydroxyl, or carboxyl functions. Appropriate protecting groups may thus include, for example, benzyl, benzyloxycarbonyl, t-butoxycarbonyl, alkyl or benzyl esters or the like, which are well known (see, for a general reference, T. W. Green; Protective Groups in Organic Synthesis (Wiley, N.Y. 1981), which is incorporated herein by reference in its entirety).

Likewise, selective protection and deprotection of any of the said groups, for instance including carbonyl, hydroxyl or amino groups, may be accomplished according to very well-known methods commonly employed in organic synthetic chemistry.

From all of the above, it should be clear that the above process, comprehensive of any variant thereof for the preparation of suitable compounds of the invention, may be conveniently modified so that to adapt the reaction conditions to the specific needs, for instance by choosing appropriate condensing agents, solvents and protective groups, as the case may be.

In the following Scheme, for compounds of formula (I) to (X), unless otherwise indicated, groups A and X have the same meanings as described for compounds of formula (I) above.

Scheme A

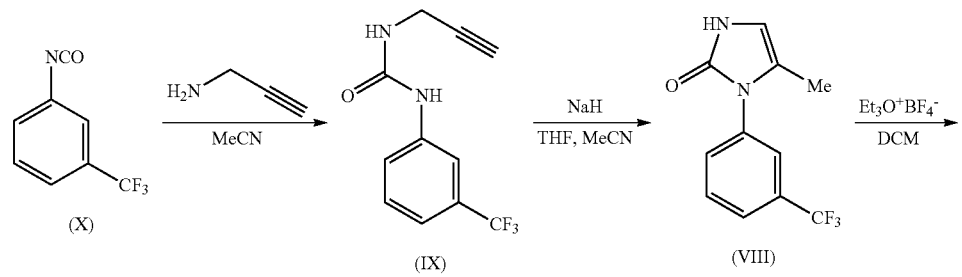

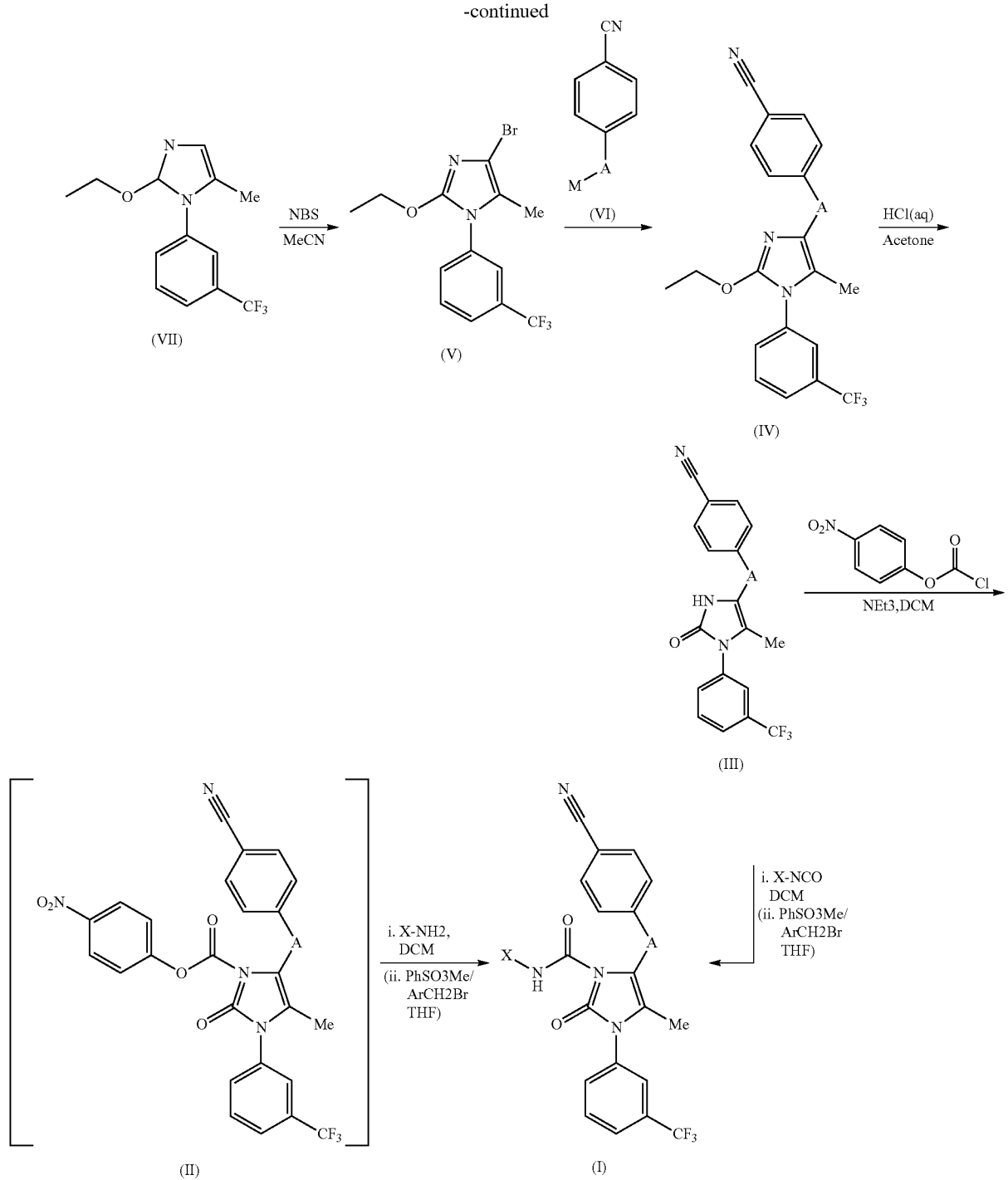

Compounds of formula (I) may be prepared from compounds of formula (III) by reaction with para-nitrophenol chloroformate in the presence of a base such as triethylamine in a solvent such as dichloromethane at an appropriate temperature of between 0° C. and the boiling point of the solvent. This gives activated carbamate of formula (II) which can subsequently be reacted with an amine of formula X—NH$_2$ in a solvent such as dichloromethane at an appropriate temperature of between 0° C. and the boiling point of the solvent to give compounds of formula (I).

Compounds of formula (I) may also be prepared from compounds of formula (III) by reaction with an appropriate isocyanate of formula X—NCO or equivalent in a suitable solvent such as dichloromethane at an appropriate temperature of between 0° C. and the boiling point of the solvent.

In the instances where compounds of formula (I) contain a quaternary ammonium moiety then a quaternisation step may also be used. This can be carried out by reaction with an alkylating agent such as methyl benzenesulphonate or benzyl bromide in a solvent such as THF at an appropriate temperature between ambient and the boiling point of the solvent.

A compound of formula (III) may be synthesized from a compound of formula (IV) by deprotection using an acid such as an aqueous hydrochloric acid solution in a solvent such as acetone at an appropriate temperature between 0° C. and the boiling point of the solvent.

A compound of formula (IV) may be synthesized from a compound of formula (V) by palladium coupling with a suitable partner fragment of formula (VI) wherein M may be, for example, a group such as —Sn(n-Bu)$_3$. The coupling can be carried out with a catalyst such as Pd(PPh$_3$)$_4$ in an appropriate solvent such as 1,4-dioxane at a suitable temperature between ambient and the boiling point of the solvent. If M is halide, for example bromide, then suitable reagents such as 2-dicyclohexylphosphino-2',4',6'-triisopropylbiphenyl, (2-dicyclohexylphosphino-2',4',6'-triisopropyl-1,1'-biphenyl)palladium(II) dichloride and tetrahydroxydiboron in the presence of potassium acetate and K$_2$CO$_3$ in an appropriate solvent such as ethanol at a suitable temperature between ambient and the boiling point of the solvent, may be used.

A compound of formula (V) may be synthesized from a compound of formula (VII) by bromination using a reagent such as N-bromosuccinimide in an appropriate solvent such as acetonitrile at a suitable temperature between 0° C. and the boiling point of the solvent.

A compound of formula (VII) may be synthesized from a compound of formula (VIII) by ethylation using a regent such as Meerwein's reagent (Et$_3$O$^+$BF$_4^-$) in an appropriate solvent such as dichloromethane at a suitable temperature between 0° C. and the boiling point of the solvent.

A compound of formula (VIII) may be synthesized from a compound of formula (IX) using a strong base such as sodium hydride in an appropriate solvent such as tetrahydrofuran/acetonitrile at a suitable temperature between 0° C. and the boiling point of the solvent.

A compound of formula (IX) maybe synthesized from a compound of formula (X) by reaction with an amine such as propargylamine in an appropriate solvent such as acetonitrile at a suitable temperature between 0° C. and the boiling point of the solvent.

Other features of the invention will become apparent in the course of the following descriptions of exemplary embodiments which are given for illustration of the invention and are not intended to be limiting thereof.

EXAMPLES

Reactions were not carried out under an inert atmosphere unless specified and all solvents and commercial reagents were used as received.

Purification by chromatography refers to purification using the CombiFlash® Companion purification system or the Biotage SP1 purification system. Where products were purified using an Isolute® SPE Si II cartridge, 'Isolute SPE Si cartridge' refers to a pre-packed polypropylene column containing unbonded activated silica with irregular particles with average size of 50 µm and nominal 60 Å porosity. Fractions containing the required product (identified by TLC and/or LCMS analysis) were pooled and concentrated in vacuo. Where HPLC was used for purification (Purification by MDAP) fractions containing the required product (identified by TLC and/or LCMS analysis) were pooled, the bulk of the organic fraction removed by evaporation, and the remaining aqueous fraction lyophilised, to give the final product. Alternatively the pooled product fraction was evaporated to dryness under reduced pressure. Where thin layer chromatography (TLC) has been used, it refers to silica gel TLC using plates, typically 3×6 cm silica gel on aluminium foil plates with a fluorescent indicator (254 nm), (e.g. Fluka 60778). Microwave experiments were carried out using a Biotage Initiator 60™ which uses a single-mode resonator and dynamic field tuning. Temperature from 40-250° C. can be achieved, and pressures of up to 30 bar can be reached.

NMR spectra were obtained on a Varian Unity Inova 400 spectrometer with a 5 mm inverse detection triple resonance probe operating at 400 MHz or on a Bruker Avance DRX 400 spectrometer with a 5 mm inverse detection triple resonance TXI probe operating at 400 MHz or on a Bruker Avance DPX 300 spectrometer with a standard 5 mm dual frequency probe operating at 300 MHz. Shifts are given in ppm relative to tetramethylsilane.

Compound names were generated using ACD/Name 2012 or AutoNom.

Analytical LC-MS Conditions

LC-MS Method 1

The Waters ZQ quadrupole mass spectrometer with a C18-reverse-phase column (30×4.6 mm Phenomenex Luna 3 µm particle size), elution with A: water+0.1% formic acid; B: MeCN+0.1% formic acid. Gradient:

| Gradient-Time | flow (mL/min) | %A | %B |
| --- | --- | --- | --- |
| 0.00 | 2.0 | 95 | 5 |
| 0.30 | 2.0 | 95 | 5 |
| 4.30 | 2.0 | 5 | 95 |
| 5.30 | 2.0 | 5 | 95 |
| 5.80 | 2.0 | 95 | 5 |
| 6.00 | 2.0 | 95 | 5 |

Detection-MS, UV (200 µl/min split to the ESI source with in-line HP1100 PDA detector)
MS ionization method-Electrospray (positive and negative ion)

LC-MS Method 2

Waters Micromass ZMD quadrupole mass spectrometer with a C18-reverse-phase column (30×4.6 mm Phenomenex Luna 3 µm particle size), elution with A: water+0.1% formic acid; B: MeCN+0.1% formic acid. Gradient:

| Gradient-Time | flow (mL/min) | %A | %B |
| --- | --- | --- | --- |
| 0.00 | 2.0 | 95 | 5 |
| 0.50 | 2.0 | 95 | 5 |
| 4.50 | 2.0 | 5 | 95 |
| 5.50 | 2.0 | 5 | 95 |
| 6.00 | 2.0 | 95 | 5 |

Detection-MS, ELS, UV (200 µl split to MS with in-line UV detector)
MS ionization method-Electrospray (positive and negative ion)

LC-MS Method 3

Waters Micromass ZQ2000 mass spectrometer with a C18-reverse-phase column (100×2.1 mm Acquity BEH with 1.7 µm particle size) maintained at 40° C., elution with A: water+0.1% formic acid; B: MeCN+0.1% formic acid. Alternatively, where specified, a C18-reverse-phase (100× 2.1 mm Acquity UPLC BEH Shield 1.7 µm particle size) column was used.

Gradient:

| Gradient-Time | flow (mL/min) | %A | %B |
|---|---|---|---|
| 0.00 | 0.4 | 95 | 5 |
| 0.40 | 0.4 | 95 | 5 |
| 6.00 | 0.4 | 5 | 95 |
| 6.80 | 0.4 | 5 | 95 |
| 7.00 | 0.4 | 95 | 5 |
| 8.00 | 0.4 | 95 | 5 |

Detection-MS, UV PDA
MS ionization method-Electrospray (positive/negative ion).

LC-MS Method U1

Acquity H-Class (quaternary pump/PDA detector) plus QDa Mass Spectrometer with an Acquity UPLC BEH C18-reverse-phase column (1.7 μm particle size, 50×2.1 mm at 50° C.), elution with A: water+0.1% formic acid; B: MeCN+0.1% formic acid.

Gradient:

| Gradient-Time | flow (mL/min) | %A | %B |
|---|---|---|---|
| 0.00 | 1.0 | 97 | 3 |
| 1.50 | 1.0 | 1 | 99 |
| 1.90 | 1.0 | 1 | 99 |
| 2.00 | 1.0 | 97 | 3 |
| 2.50 | 1.0 | 97 | 3 |

Detection-MS, UV
MS ionization method-Electrospray (positive and negative ion).

LC-MS Method U2

Acquity H-Class (quaternary pump/PDA detector) plus QDa Mass Spectrometer with an Acquity UPLC BEH C18-reverse-phase column (1.7 μm particle size, 50×2.1 mm at 40° C.), elution with A: water+0.1% formic acid; B: MeCN+0.1% formic acid.

Gradient:

| Gradient-Time | flow (mL/min) | %A | %B |
|---|---|---|---|
| 0.00 | 1.0 | 97 | 3 |
| 1.50 | 1.0 | 1 | 99 |
| 1.90 | 1.0 | 1 | 99 |
| 2.00 | 1.0 | 97 | 3 |
| 2.50 | 1.0 | 97 | 3 |

Detection-MS, UV
MS ionization method-Electrospray (positive and negative ion).

LC-MS Method 7

HP1100 (quaternary pump/PDA detector) plus ZQ Mass Spectrometer with a Phenomenex Luna C18(2) 3μ, 30×4.6 mm column, elution with A: water+0.1% formic acid; B: MeCN+0.1% formic acid.

Gradient:

| Gradient-Time | flow | %A | %B |
|---|---|---|---|
| 0.00 | 2.0 | 95 | 5 |
| 0.30 | 2.0 | 95 | 5 |
| 4.30 | 2.0 | 5 | 95 |
| 5.30 | 2.0 | 5 | 95 |
| 5.80 | 2.0 | 95 | 5 |
| 6.00 | 2.0 | 95 | 5 |

Detection-MS, UV
MS ionization method-Electrospray (positive and negative ion)

Abbreviations used in the experimental section:
DCM Dichloromethane
DIPEA Di-isopropylethylamine
DMF N,N-dimethylformamide
DMSO Dimethylsulphoxide
$Et_2O$ Diethyl ether
EtOAc Ethyl acetate
h Hour
HPLC High performance liquid chromatography
IMS Industrial methylated spirits
LC-MS Liquid chromatography-mass spectrometry
MeCN Acetonitrile
MDAP Mass Directed Automatic Purification
Min Minutes
NBS N-Bromosuccinimide
Rt Retention time
RT Room temperature
THF Tetrahydrofuran In the procedures that follow, some of the starting materials are identified through an "Intermediate" or "Example" number. The starting material may not necessarily have been prepared from the batch referred to.

When reference is made to the use of a "similar" or "analogous" procedure such a procedure may involve minor variations, for example reaction temperature, reagent/solvent amount, reaction time, work-up conditions or chromatographic purification conditions.

The present invention will now be further described by the following examples.

Intermediate A. 4-(5-{5-Methyl-2-oxo-1-[3-(trifluoromethyl)phenyl]-2,3-dihydro-1H-imidazol-4-yl}-1H-pyrazol-1-yl)benzonitrile

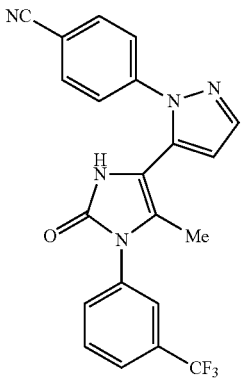 [SMILES: Cc1c(-c2ccnn2-c2ccc(C#N)cc2)[nH]c(=O)n1-c1cccc(C(F)(F)F)c1]

Intermediate A1.
1-Prop-2-yn-1-yl-3-[3-(trifluoromethyl)phenyl]urea

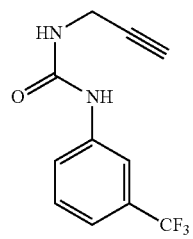 [SMILES: C#CCNC(=O)Nc1cccc(C(F)(F)F)c1]

A solution of propargyl amine (4.41 g, 5.13 mL, 80 mmol) in MeCN (30 mL) was added to a stirred solution of 3-(trifluoromethyl)phenyl isocyanate (15.0 g, 12.12 mL, 80 mmol) in MeCN (60 mL) under a nitrogen atmosphere. The reaction mixture was cooled with a RT cooling bath and the rate of addition was such that the internal temperature did not exceed 35° C. After 1.5 h the mixture was concentrated in vacuo. EtOAc (10 ml) was added to the residue and the mixture was sonicated for 2 minutes. The resultant slurry was diluted with cyclohexane (40 ml). The mixture was stirred for 10 minutes and the solid was then recovered by filtration. The mother liquors were concentrated in vacuo and the residue dissolved in EtOAc (10 mL). Dilution with cyclohexane (90 ml) precipitated a second batch of product which was recovered by filtration. The two batches were combined as an ethyl acetate solution and concentrated in vacuo to afford the title compound as a fawn solid (16.65 g).

LCMS (Method 2): Rt=3.22 min, m/z 243 [M+H]$^+$

Intermediate A2. 5-Methyl-1-[3-(trifluoromethyl) phenyl]-1,3-dihydro-2H-imidazol-2-one

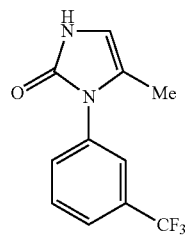 [SMILES: Cc1c[nH]c(=O)n1-c1cccc(C(F)(F)F)c1]

A solution of 1-prop-2-yn-1-yl-3-[3-(trifluoromethyl)phenyl]urea (intermediate A1) (11.2 g, 46 mmol) in THF (60 mL) and acetonitrile (120 mL) was added, under a nitrogen atmosphere, to a stirred suspension of sodium hydride (60% dispersion in mineral oil) (4.62 g, 115 mmol) in THF (60 mL) at such a rate that gas evolution was not over-vigorous and the internal temperature remained below 30° C. The mixture was stirred at RT for 2.5 h, a thick precipitate having formed within 1 h. The reaction mixture was cautiously quenched with water (15 mL) and the resulting solution was treated with 1 M hydrochloric acid (150 mL, 150 mmol). The mixture was stirred for 4 hours then allowed to stand for 15 hours. Saturated brine (150 mL) was added and the phases were partitioned. The aqueous phase was extracted with EtOAc (100 mL). The combined organic phase was washed with saturated brine (100 mL), dried (sodium sulfate) and concentrated in vacuo. The residue was triturated with EtOAc (33 mL). The resultant solid was taken into DCM and filtered. The filtrate was concentrated in vacuo to afford the title compound (10.0 g) as a fawn solid.

LCMS (Method 1): Rt=2.63 min, m/z 243 [M+H]$^+$

Intermediate A3. 2-Ethoxy-5-methyl-1-[3-(trifluoromethyl)phenyl]-1H-imidazole

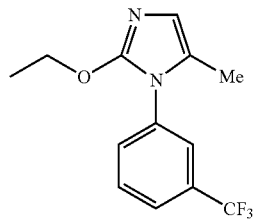 [SMILES: CCOc1ncc(C)n1-c1cccc(C(F)(F)F)c1]

A solution of triethyloxonium tetrafluoroborate (9.0 g, 47 mmol) in DCM (62 mL) was added to a stirred solution of 5-methyl-1-[3-(trifluoromethyl)phenyl]-1,3-dihydro-2H-imidazol-2-one (Intermediate A2, 9.0 g, 37 mmol) in DCM (124 mL) under a nitrogen atmosphere. The solution was stirred at RT for 2.5 h then treated with water (50 mL) then 1 M sodium hydroxide (50 mL). The phases were partitioned. The aqueous phase was washed with DCM (2×50 mL). The combined organic phase was dried (sodium sulfate). The solution of the crude product was filtered through 2×50 g flash SCX 2 cartridges. Each cartridge was rinsed with 10% methanol in DCM (100 mL) then the product fraction was eluted with 2M methanolic ammonia solution (100 mL). The fractions recovered with methanolic ammonia were combined and concentrated in vacuo to afford the title compound (7.92 g) as a brown solid.

LCMS (Method 1): Rt=2.41 min, m/z 271 [M+H]$^+$

Intermediate A4. 4-Bromo-2-ethoxy-5-methyl-1-[3-(trifluoromethyl)phenyl]-1H-imidazole

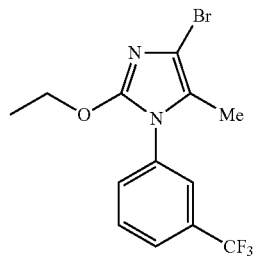 [SMILES: CCOc1nc(Br)c(C)n1-c1cccc(C(F)(F)F)c1]

A solution of NBS (5.16 g, 29 mmol) in MeCN (60 mL) was added to a stirred solution of 2-ethoxy-5-methyl-1-[3-(trifluoromethyl)phenyl]-1H-imidazole (Intermediate A3, 7.92 g, 29 mmol) in MeCN (115 mL) at such a rate that the internal temperature of the mixture did not exceed 25° C. (a RT cooling bath was used). After 0.5 h the mixture was diluted with water (50 mL) and saturated sodium carbonate (aq) (50 mL). Ethyl acetate (50 mL) was added. The mixture was stirred vigorously then the phases were separated. The organic phase was washed with saturated brine (50 mL), dried (sodium sulfate) and concentrated in vacuo. The residue was taken into dichloromethane and filtered through a 25 g Si II SPE cartridge. The cartridge was washed with DCM and 10% EtOAc in DCM. The filtrate was concentrated in vacuo to afford the title compound as an off-white solid (8.93 g).

LCMS (Method 1): Rt=3.86 min, m/z 349 [M($^{79}$Br)+H]$^+$

Intermediate A5. 4-(5-{2-Ethoxy-5-methyl-1-[3-(trifluoromethyl)phenyl]-1H-imidazol-4-yl}-1H-pyrazol-1-yl)benzonitrile

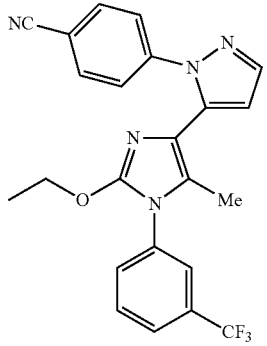 [SMILES: CCOc1nc(-c2ccnn2-c2ccc(C#N)cc2)c(C)n1-c1cccc(C(F)(F)F)c1]

A solution of 4-bromo-2-ethoxy-5-methyl-1-[3-(trifluoromethyl)phenyl]-1H-imidazole (Intermediate A4, 3.14 g, 9 mmol) and 4-(5-tributylstannyl-pyrazol-1-yl)-benzonitrile (see WO2014009425A1, which is incorporated herein by reference in its entirety) (6.19 g, 13.5 mmol) in 1,4-dioxane (45 mL) was degassed by bubbling argon through the solution for 5 minutes. Tetrakis(triphenylphosphine)palladium(0) (0.52 g, 0.45 mmol) was added and after a further period of degassing the mixture was heated at 94° C. under an argon atmosphere during 17 h. The mixture was cooled to RT and filtered through a 50 g flash SCX 2 cartridge. The cartridge was eluted with DCM, 10% methanol in DCM then a 1:1 mixture of 2M ammonia in methanol and DCM. Concentration of the appropriate fractions in vacuo afforded the crude product. This was triturated with cyclohexane and dried in vacuo to afford the title compound (3.01 g).

LCMS (Method 1): Rt=3.84 min, m/z 438 [M+H]$^+$

4-(5-{5-Methyl-2-oxo-1-[3-(trifluoromethyl)phenyl]-2,3-dihydro-1H-imidazol-4-yl}-1H-pyrazol-1-yl)benzonitrile (Intermediate A)

A suspension of 4-(5-{2-ethoxy-5-methyl-1-[3-(trifluoromethyl)phenyl]-1H-imidazol-4-yl}-1H-pyrazol-1-yl)benzonitrile (0.71 g, 1.6 mmol) in acetone (10 mL) and 1M hydrochloric acid (1.6 mL) was heated at 60° C. for 14 h. The mixture was cooled, diluted with acetone (50 mL) and filtered through a 5 g flash NH2 column. The filtrate was concentrated in vacuo. The residue was twice taken into acetonitrile and reconcentrated. The residue was triturated with acetone (10 mL) and dried in vacuo to afford the title compound (0.45 g)

LCMS (Method 3): Rt=4.32 min, m/z 410.1 [M+H]$^+$
$^1$H NMR (400 MHz, CDCl$_3$): δ 9.27 (1H, br s), 7.78 (1H, d J=1.8 Hz), 7.73-7.63 (4H, m), 7.60-7.56 (3H, m), 7.49 (1H, dJ=7.5 Hz), 6.56 (1H, d J=1.8 Hz), 1.84 (3H, S).

Intermediate B. (S)-1-(3-Dimethylaminomethyl-[1,2,4]oxadiazol-5-yl)-ethylamine TFA salt

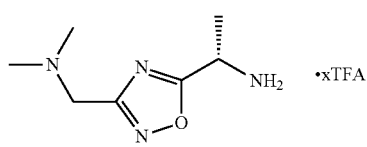

Intermediate B1. [(S)-1-(3-Dimethylaminomethyl-[1,2,4]oxadiazol-5-yl)-ethyl]-carbamic acid tert-butyl ester

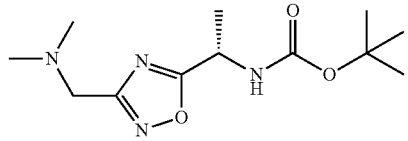 [SMILES: C[C@H](NC(=O)OC(C)(C)C)c1nc(CN(C)C)no1]

A solution of 2-(dimethylamino)-N-hydroxyethanimidamide (500 mg, 4.27 mmol) and Boc-alanine (890 mg, 4.70 mmol) was formed in dichloromethane (20 mL) with N,N-diisopropylethylamine (1.1 g, 8.54 mmol). HATU (1.95 g, 5.12 mmol) was added and the mixture stirred at ambient temperature for 1 h then was heated at reflux for 1 h. The mixture was allowed to cool to RT then partitioned between DCM and sat. aqueous sodium bicarbonate. The organic phase was washed with brine, dried over MgSO$_4$ then evaporated. This material was then dissolved in Dioxane (10 mL) and heated at reflux for 4 h. The mixture was then allowed to cool and diluted with ethyl acetate, washed with 10% aqueous potassium carbonate, brine, dried over MgSO$_4$ then evaporated. Purification by flash column chromatography (40 g Si cartridge) eluting with a gradient of 0-10% (2N NH3 in MeOH) in DCM gave Intermediate B1 as a white solid (230 mg, 20%)

LCMS (Method U1): Rt=0.70 min, m/z 271.2 [M+H]$^+$

(S)-1-(3-Dimethylaminomethyl-[1,2,4]oxadiazol-5-yl)-ethylamine TFA salt

Intermediate B1 (230 mg, 0.85 mmol) was dissolved in DCM (6 mL). Trifluoroacetic acid (2 mL) was added and the mixture stirred for 2 h at ambient temperature. Evaporation gave Intermediate B containing ~4 eq of TFA (320 mg, 60%).
$^1$H NMR (400 MHz, d6-DMSO): δ 9.01 (3H, br s), 5.05-4.96 (1H, m), 4.68 (2H, s), 2.90 (6H, s), 1.64 (3H, d, J=7.0).

Intermediate C. (S)-1-(5-Dimethylaminomethyl-[1,3,4]oxadiazol-2-yl)-ethylamine TFA salt

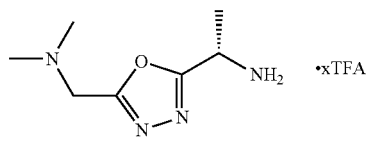

Intermediate C1. {(S)-2-[N'-(2-Dimethylaminoacetyl)-hydrazino]-1-methyl-2-oxo-ethyl}-carbamic acid tert-butyl ester

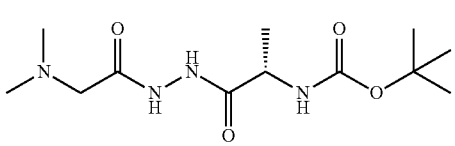 [SMILES: C[C@H](NC(=O)OC(C)(C)C)C(=O)NNC(=O)CN(C)C]

A solution of Boc-Alanine (1 g, 5.3 mmol) was formed in DCM (40 mL). EDC hydrochloride (1.02 g, 5.3 mmol) was added followed by 1-hydroxybenzotriazole hydrate (716 mg, 5.3 mmol) and the mixture stirred for 5 mins. N,N-diisopropylethylamine (1.85 mL, 10.6 mmol) was added giving a yellow solution. Girard's Reagent D (1.1 g, 5.8 mmol) was added and the mixture stirred for 24 h. The mixture was partitioned between DCM and sat. aqueous sodium bicarbonate The organic phase was isolated using a phase separation cartridge and evaporated. Purification by flash column chromatography (40 g Si cartridge) eluting with a gradient of 0-10% (2N NH3 in MeOH) in DCM gave Intermediate C1 as a colourless gum (870 mg, 57%).

$^1$H NMR (400 MHz, CDCl$_3$): δ 8.63 (1H, br s), 5.00-4.89 (1H, m), 4.34-4.22 (1H, m), 3.08 (2H, s), 2.34 (6H, s), 1.46 (9H, s), 1.41 (3H, d, J=7.1 Hz).

Intermediate C2. [(S)-1-(5-Dimethylaminomethyl-[1,3,4]oxadiazol-2-yl)-ethyl]-carbamic acid tert-butyl ester

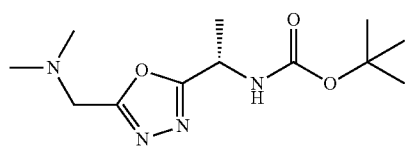 [SMILES: C[C@H](NC(=O)OC(C)(C)C)c1nnc(CN(C)C)o1]

A solution of Intermediate C1 (288 mg, 1 mmol) was formed in DCM (10 mL). Burgess Reagent (357 mg, 1.5 mmol) was added and the mixture stirred over night at ambient temperature. The mixture was partitioned between water and DCM. The organic phase was isolated using a phase separation cartridge and evaporated. Purification by flash column chromatography (12 g Si cartridge) eluting with a gradient of 0-10% (2N NH3 in MeOH) in DCM gave Intermediate C2 as a colourless oil (260 mg, 96%).

$^1$H NMR (400 MHz, CDCl$_3$): δ 5.09 (2H, br s), 3.75 (2H, s), 2.35 (6H, s), 1.59 (3H, m, partially obscured by water peak), 1.45 (9H, s).

(S)-1-(5-Dimethylaminomethyl-[1,3,4]oxadiazol-2-yl)-ethylamine TFA salt

Intermediate C2 (230 mg, 0.85 mmol) was dissolved in DCM (6 mL). Trifluoroacetic acid (2 mL) was added and the mixture stirred for 2.5 h at ambient temperature. Evaporation gave Intermediate C containing ~3 eq of TFA (530 mg, quant).

$^1$H NMR (400 MHz, d6-DMSO): δ 8.93 (3H, br s), 4.95-4.86 (1H, m), 4.77 (2H, s), 2.90 (6H, s), 1.61 (3H, d, J=7.0).

Intermediate D. (S)-1-(5-Dimethylaminomethyl-oxazol-2-yl)-ethylamine TFA salt

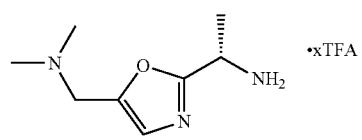

Intermediate D1. ((S)-1-Prop-2-ynylcarbamoyl-ethyl)-carbamic acid tert-butyl ester

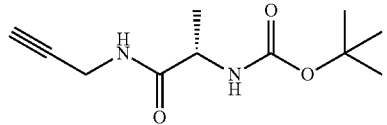 [SMILES: C#CCNC(=O)[C@H](C)NC(=O)OC(C)(C)C]

A solution of Boc-alanine (1 g, 5.3 mmol) was formed in DCM (40 mL). EDC hydrochloride (1.02 g, 5.3 mmol) was added followed by 1-hydroxybenzotriazole hydrate (716 mg, 5.3 mmol) and the mixture stirred for 5 mins. Propargyl amine (407 µL, 6.4 mmol) was added and the mixture stirred for 27 h at ambient temperature. The mixture was partitioned between DCM and water. The organic phase was isolated using a phase separation cartridge and evaporated. Purification by flash column chromatography (40 g Si cartridge) eluting with a gradient of 0-100% EtOAc in DCM gave Intermediate D1 as a white solid (1.04 g, 87%).

$^1$H NMR (400 MHz, CDCl$_3$): δ 6.39 (1H, br s), 4.89 (1H, br s), 4.19-4.09 (1H, m), 4.09-4.00 (2H, m), 2.22 (1H, t, J=2.5 Hz), 1.45 (9H, s), 1.36 (3H, d, J=7.1 Hz).

Intermediate D2. [(S)-1-(5-Bromomethyl-oxazol-2-yl)-ethyl]-carbamic acid tert-butyl ester

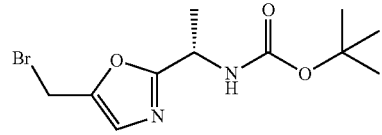 [SMILES: C[C@H](NC(=O)OC(C)(C)C)c1ncc(CBr)o1]

A solution of Intermediate D1 (500 mg, 2.21 mmol) was formed in chloroform (10 mL). Gold (III) chloride (7 mg, 0.022 mmol) was added and the mixture was stirred at ambient temperature for 4 hours before cooling to 0° C. 2,6-Lutadine (260 mg, 2.43 mmol) was added followed by bromine (350 mg, 2.21 mmol) in chloroform (2 mL). The mixture was allowed to warm to RT overnight. The mixture was diluted with DCM and washed with an aqueous sodium thiosulphate solution, sat. aqueous sodium bicarbonate solution, brine and then dried over MgSO$_4$. Purification by flash column chromatography (24 g Si cartridge) eluting with a gradient of 0-100% EtOAc in cyclohexane gave Intermediate D2 as a colourless oil (320 mg, 47%).

$^1$H NMR (400 MHz, CDCl$_3$): δ 6.99 (1H, s), 5.10 (1H, br s), 4.95 (1H, br s), 4.46 (2H, s), 1.54 (3H, d, partially obscured by water), 1.45 (9H, s).

Intermediate D3. [(S)-1-(5-Dimethylaminomethyl-oxazol-2-yl)-ethyl]-carbamic acid tert-butyl ester

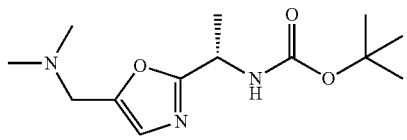 [SMILES: C[C@H](NC(=O)OC(C)(C)C)c1ncc(CN(C)C)o1]

Intermediate D2 (320 mg, 1.04 mmol) was dissolved in a solution of 2N NH₃ in THF and stirred at ambient temperature for 1 hour. The mixture was filtered through celite to remove the white precipitate and the filtrate was evaporated. Purification by flash column chromatography (12 g Si cartridge) eluting with a gradient of 0-100% EtOAc in cyclohexane gave Intermediate D3 as a yellow oil (200 mg, 73%).

¹H NMR (400 MHz, CDCl₃): δ 6.85 (1H, s), 5.17 (1H, br s), 4.93 (1H, br s), 3.50 (2H, s), 2.27 (6H, s), 1.52 (3H, d, J=6.9 Hz), 1.44 (9H, s).

(S)-1-(5-Dimethylaminomethyl-oxazol-2-yl)-ethyl-amine TFA salt

Intermediate D3 (200 mg, 0.76 mmol) was dissolved in DCM (6 mL). Trifluoroacetic acid (2 mL) was added and the mixture stirred for 2 h at ambient temperature. Evaporation gave Intermediate D containing ~4 eq of TFA (490 mg, quant).

¹H NMR (400 MHz, d6-DMSO): δ 8.75 (3H, br s), 7.46 (1H, s), 4.71 (1H, br s), 4.50 (2H, s), 2.79 (6H, s), 1.56 (3H, d, J=6.9 Hz).

Intermediate E. (S)-1-(5-Dimethylaminomethyl-oxazol-2-yl)-2-methyl-propylamine TFA salt

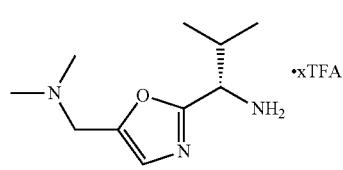

Intermediate E was synthesized from Boc-valine using a similar procedure to that for Intermediate D.

¹H NMR (400 MHz, d6-DMSO): δ 8.77 (3H, br s), 7.49 (1H, s), 4.52 (2H, s), 4.46, (1H, s), 2.78 (6H, s), 2.31-2.16 (1H, m), 1.01 (3H, d, J=6.8 Hz), 0.87 (3H, d, J=6.8 Hz).

Intermediate F. (S)-1-(5-Dimethylaminomethyl-oxazol-2-yl)-propylamine TFA salt

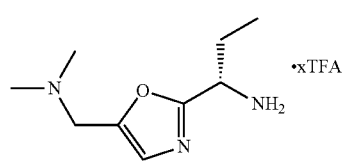

Intermediate F was synthesized from Boc-(S)-2-aminobutyric acid using a similar procedure to that for Intermediate D.

¹H NMR (400 MHz, d6-DMSO): δ 8.77 (3H, br s), 7.48 (1H, s), 4.55 (1H, br s), 4.51, (2H, s), 2.79 (6H, s), 2.02-1.90 (2H, m), 0.91 (3H, t, J=7.4 Hz).

Intermediate G. 1-(5-Dimethylaminomethyl-oxazol-2-yl)-cyclopropylamine TFA salt

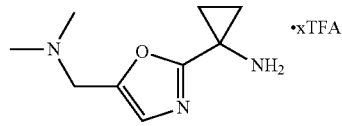

Intermediate G was synthesized from Boc-1-amino-cyclopropanecarboxylic acid using a similar procedure to that for Intermediate D.

¹H NMR (400 MHz, d6-DMSO): δ 9.20 (3H, br s), 7.43 (1H, s), 4.46 (2H, s), 2.77 (6H, s), 1.53 (4H, br s).

Intermediate H. 1-(5-Dimethylaminomethyl-oxazol-2-yl)-1-methyl-ethylamine TFA salt

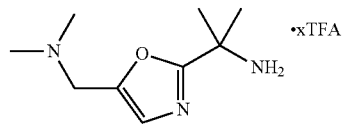

Intermediate H was synthesized from Boc-2-amino-2-methyl-propionic acid using a similar procedure to that for Intermediate D.

¹H NMR (400 MHz, d6-DMSO): □ 8.88 (3H, br s), 7.47 (1H, s), 4.51 (2H, s), 2.79 (6H, s), 1.66 (6H, s).

Intermediate I. ±1-(4-Dimethylaminomethyl-thiazol-2-yl)-ethylamine

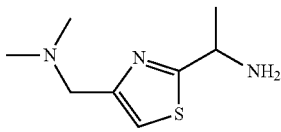

Intermediate I1.
1-(4-Dimethylaminomethyl-thiazol-2-yl)-ethanone

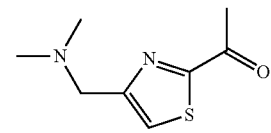

Dimethyl-thiazol-4-ylmethyl-amine (US20150166548) (0.78 g, 5.5 mmol) was stirred in THF (35 ml) at −78° C. as n-butyllithium (1.6 M in hexanes, 4.75 mL, 7.6 mmol) was added over 5 min. keeping the temperature below −60° C. After a further 15 min, N-methoxy-N-methylacetamide (1.13 g, 11 mmol) was added. The mixture was allowed to warm gradually to 0° C., then diluted with water (15 mL) and sat. brine (15 mL). The phases were separated and the aqueous was extracted with DCM (15 mL). The combined organics were dried (Na₂SO₄) and concentrated. The residue was chromatographed on a 10 g silica column eluting with 0% to 10% MeOH in DCM. The material thus obtained was further purified by SCX-2, loading in DCM and washing with 20% MeOH in DCM before eluting with 20% of 2M methanolic ammonia in DCM to give 1-(4-dimethylaminomethyl-thiazol-2-yl)-ethanone as a yellow brown oil (710 mg, 70%).

LCMS (Method U2) Rt=0.21 min, m/z=185.1 [M+H]+.

Intermediate I2. ±1-(4-Dimethylaminomethyl-thiazol-2-yl)-ethanol

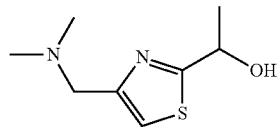

1-(4-Dimethylaminomethyl-thiazol-2-yl)-ethanone (impure, 800 mg, ca. 3.7 mmol) in MeOH (12 mL) was stirred in an ice bath and treated with sodium borohydride (168 mg, 4.44 mmol). When gas evolution had ceased it was allowed to warm slowly to RT. After a further 16 h the mixture was diluted with water (30 mL) and extracted with DCM (3×25 mL). The aqueous phase was treated with NaCl and extracted with DCM (2×25 mL). The combined organics were dried (Na$_2$SO$_4$) and evaporated to give title compound as a brown oil (0.58 g, 84%).

LCMS (Method U2) Rt=0.19 min, m/z=187 [M+H]+.

Intermediate I3. ±[2-(1-Azido-ethyl)-thiazol-4-ylmethyl]-dimethyl-amine

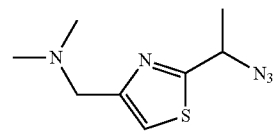

±1-(4-Dimethylaminomethyl-thiazol-2-yl)-ethanol (0.58 g, 3.1 mmol) in toluene (3.1 mL) was treated with diphenylphosphoryl azide (1.023 g, 3.72 mmol) and DBU (487 mg, 3.2 mmol). The mixture was stirred at RT for 3 days then allowed to stand for 65 h. It was then heated at 60° C. for 2 h. The mixture was cooled and diluted with DCM (20 mL). The mixture was washed with sat. Na$_2$CO$_3$ solution and the aqueous phase was extracted with more DCM (20 mL). The combined organic phases were dried (Na$_2$SO$_4$) and loaded onto a 10 g silica column and eluted with DCM followed by 5%, 10% and 15% MeOH in DCM. The product was re-chromatographed on 5 g and 2 g columns to afford the title compound (250 mg, 33%) as a brown oil.

LCMS (Method U2) Rt=0.79 min, m/z=212.1 [M+H]+.

±1-(4-Dimethylaminomethyl-thiazol-2-yl)-ethylamine

±[2-(1-Azido-ethyl)-thiazol-4-ylmethyl]-dimethyl-amine (250 mg, 1 mmol) in THF (5 mL) and water (0.5 mL) was treated with triphenylphosphine (500 mg, 1.9 mmol) and heated at 56° C. for 17 h. The mixture was cooled and filtered through a 2 g SCX-2 cartridge washing with 20% MeOH in DCM and eluting with 20% 2M methanolic ammonia in DCM to give the title compound (139 mg, ca. 70%) as a yellow oil.

LCMS (Method U2) Rt=0.22 min, m/z=186.1 [M+H]+.

The following compounds were prepared from the starting materials using analogous procedures to that described for Intermediate D1 and Intermediate D.

| Intermediate | Structure | Starting materials | | Data |
|---|---|---|---|---|
| J | 4-Trans-amino-cyclohexane-carboxylic acid (2-dimethyl-amino-ethyl)-amide TFA salt | N,N-Dimethyl-ethylene-diamine | 4-Trans-tert-butoxy-carbonyl-aminocyclo-hexane-carboxylic acid | $^1$H NMR (400 MHz, d6-DMSO): δ 9.72 (1H, br s), 8.11 (1H, m), 7.88 (3H, br s), 3.42-3.37 (2H, m), 3.17-3.10 (3H, m), 2.81 (6H, d, J = 5 Hz), 2.13-2.02 (1H, m), 2.02-1.95 (2H, m), 1.88-1.80 (2H, m), 1.49-1.22 (4H, m). |
| K | 4-Cis-amino-cyclohexane-carboxylic acid (2-dimethyl-amino-ethyl)-amide TFA salt | N,N-Dimethyl-ethylene-diamine | 4-Cis-tert-butoxy-carbonyl-amino-cyclo-hexane-carboxylic acid | $^1$H NMR (400 MHz, d6-DMSO): δ 9.65 (1H, br s), 8.04 (1H, m), 7.81 (3H, br s), 3.42-3.37 (2H, m), 3.17-3.10 (3H, m), 2.81 (6H, d, J = 5 Hz), 2.35-2.29 (1H, m), 1.90-1.81 (2H, m), 1.72-1.50 (6H, m). |

| Intermediate | Structure | Starting materials | | Data |
|---|---|---|---|---|
| L | 4-Trans-amino-cyclohexane-carboxylic acid (2-dimethyl-amino-ethyl)-methyl-amide TFA salt | N,N,N'-Trimethyl-ethylene diamine | 4-Trans-tert-butoxy-carbonyl-amino-cyclo-hexane carboxylic acid | $^1$H NMR (400 MHz, d6-DMSO): δ 8.20 (3H, br m), 3.66-3.61 (1H, m), 3.21-3.14 (2H, m), 3.05 (3H, s), 2.98-2.90 (1H, br m), 2.81-2.72 (8H, m), 2.01-1.94 (2H, m), 1.84-1.75 (2H, m), 1.52-1.31 (4H, m). |
| M | 1-(4-Amino-4-methyl-piperidin-1-yl)-2-dimethylamino-ethanone TFA salt | (4-Methyl-piperidin-4-yl)-carbamic acid tert-butyl ester | Dimethyl-amino-acetic acid | LCMS (Method U1) Rt = 0.11 min, m/z = 200 [M + H]+. |
| N | N-(Trans-4-amino-cyclohexyl-methyl)-2-dimethylamino-acetamide | (Trans-4-amino-methyl-cyclo-hexyl)-carbamic acid tert-butyl ester | Dimethyl-amino-acetic acid | $^1$H NMR (400 MHz, CDCl$_3$): δ 5.67 (1H, m), 4.46 (1H, br s), 3.76-3.69 (1H, m), 3.35 (1H, br s), 3.23-3.17 (1H, m), 3.05-3.00 (1H, m), 2.80 (6H, s), 2.05-1.99 (2H, m), 1.83-1.77 (2H, m), 1.61 (1H,brs), 1.22-0.97 (4H, m). |
| O | 3-Trans-amino-cyclobutane-carboxylic acid (2-dimethyl-amino-ethyl)-amide TFA salt | N,N-Dimethyl-ethylene-diamine | 3-Trans-tert-butoxy-carbonyl-amino-cyclo-butane-carboxylic acid | $^1$H NMR (400 MHz, d6-DMSO): δ 8.14 (1H, m), 8.03 (3H, br s), 3.81-3.72 (1H, m), 3.41-3.37 (2H, m), 3.15-3.10 (2H, m), 3.07-2.99 (1H, m), 2.81 (6H, d, J = 4.7 Hz), 2.41-2.34 (2H, m), 2.30-2.22 (2H, m). |

-continued

| Intermediate | Structure | Starting materials | | Data |
|---|---|---|---|---|
| P | 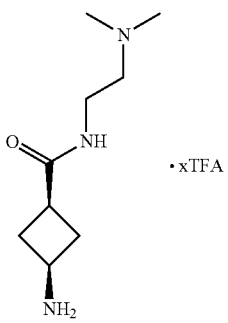<br>3-Cis-amino-cyclobutane-carboxylic acid (2-dimethyl-amino-ethyl)-amide TFA salt | N,N-Dimethyl-ethylene-diamine | 3-Cis-tert-butoxy-carbonyl-amino-cyclo-butane-carboxylic acid | $^1$H NMR (400 MHz, d6-DMSO): δ 8.16 (1H, m), 8.02 (3H, br s), 3.65-3.57 (1H, m), 3.42-3.37 (2H, m), 3.15-3.10 (2H, m), 2.83-2.76 (7H, m), 2.37-2.29 (2H, m), 2.24-2.15 (2H, m). |
| Q | 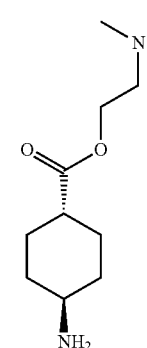<br>4-Trans-amino-cyclohexane-carboxylic acid 2-dimethylamino-ethyl ester | 2-Dimethyl-amino-ethanol | 4-Trans-tert-butoxy-carbonyl-amino-cyclo-hexane-carboxylic acid | $^1$H NMR (400 MHz, CDCl$_3$): δ 4.16 (2H, t, J = 5.7 Hz), 2.71-2.62 (1H, m), 2.55 (2H, t, J = 5.7 Hz), 2.31-2.23 (7H, m), 2.02-1.88 (4H, m), 1.53-1.43 (2H, m), 1.16-1.05 (2H, m). |
| R | 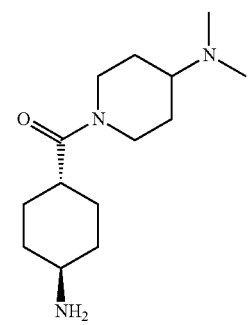<br>(4-Trans-amino-cyclohexyl)-(4-dimethylamino-piperidin-1-yl)-methanone | Dimethyl-piperidin-4-yl-amine | 4-Trans-tert-butoxy-carbonyl-amino-cyclo-hexane-carboxylic acid | $^1$H NMR (400 MHz, CDCl$_3$): δ 4.64 (1H, d, J = 13.4 Hz), 3.94 (1H, d, J = 13.4 Hz), 3.06-2.98 (1H, m), 2.76-2.67 (1H, m), 2.60-2.51 (1H, m), 2.47-2.30 (2H, m), 2.29 (6H, s), 1.96-1.56 (8H, m), 1.45-1.31 (2H, m), 1.19-1.05 (2H, m). |
| S | 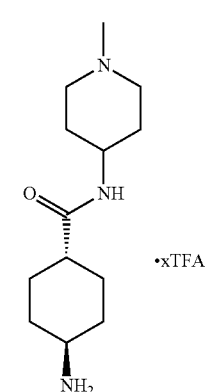<br>4-Trans-amino-cyclohexanecarboxylic acid (1-methyl-piperidin-4-yl)-amide TFA salt | 1-Methyl-piperidin-4-ylamine | 4-Trans-tert-butoxy-carbonyl-amino-cyclo-hexane-carboxylic acid | $^1$H NMR (400 MHz, d6-DMSO): δ 10.56 (1H, br s), 8.04-7.95 (4H, m), 3.73-3.65 (5H, m), 3.57 (3H, s), 3.52-3.44 (2H, m), 3.38-3.32 (2H, m), 3.26-3.20 (1H, m), 3.09-2.90 (3H, m), 2.72-2.66 (5H, m). |

Example 1. 5-[2-(4-Cyano-phenyl)-2H-pyrazol-3-yl]-4-methyl-2-oxo-3-(3-trifluoromethyl-phenyl)-2,3-dihydro-imidazole-1-carboxylic acid trans-(4-dimethylaminomethyl-cyclohexyl)-amide

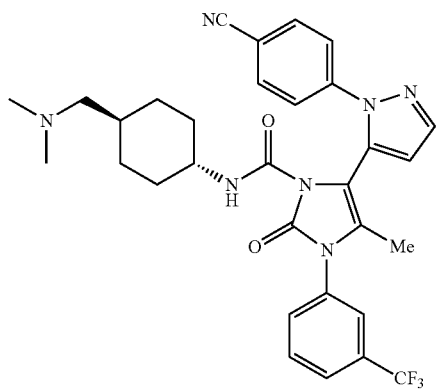 [SMILES: Cc1c(-c2ccnn2-c2ccc(C#N)cc2)n(C(=O)N[C@H]2CC[C@H](CN(C)C)CC2)c(=O)n1-c1cccc(C(F)(F)F)c1]

A stirred mixture of 4-{5-[5-methyl-2-oxo-1-(3-trifluoromethyl-phenyl)-2,3-dihydro-1H-imidazol-4-yl]-pyrazol-1-yl}-benzonitrile (Intermediate A, 500 mg, 1.22 mmol) and dichloromethane (15 mL) was treated with 4-nitrophenyl chloroformate (470 mg, 2.33 mmol). Triethylamine (726 mg, 1.0 mL, 7.12 mmol) was added to the resultant solution and stirring was continued for 30 minutes. The solution was added to trans-4-dimethylaminomethyl-cyclohexylamine trifluoroacetate salt (1.55 mmol). The mixture was stirred for 1 h then diluted with DCM (15 mL). Water (25 mL) and saturated sodium carbonate solution (5 mL) were added. The phases were partitioned. The aqueous phase was washed with DCM (2×30 mL). The combined organic phase was dried (sodium sulfate) and concentrated in vacuo. The residue was part purified using a 10 g SCX-2 column loading with DCM, washing with 4:1 DCM: methanol and eluting with 4:1 DCM: 2M methanolic ammonia. Concentration of the appropriate fractions gave the crude product. This was further purified by filtration through 2×5 g flash NH2 cartridges washing with 4:1 DCM: methanol, then flash chromatography on a 5 g SiII cartridge eluting with DCM, 50:1, 9:1 then 4:1 DCM: methanol. Concentration of the appropriate fractions gave the title compound (425 mg, 0.7 mmol, 59%).

LCMS (Method 3): Rt=3.76 min, m/z 592 [M+H]+
$^1$H NMR (400 MHz, d6-DMSO): δ 8.18 (1H, d, J=7.7 Hz), 8.02 (1H, s), 7.95-7.76 (6H, m), 7.69-7.61 (2H, m), 6.63 (1H, d, J=1.7 Hz), 3.20-3.08 (1H, m), 2.06 (6H, s), 1.94 (2H, d, J=7.2 Hz), 1.89 (3H, s), 1.75-1.61 (3H, m), 1.47-1.37 (1H, m), 1.37-1.24 (1H, m), 1.16-1.03 (1H, m), 0.99-0.71 (3H, m).

The following compounds were prepared by analogous procedures to that used in Example 1. In the table below where rotameric signals have been identified in the NMR spectrum these have been labelled by *.

| Ex | Structure | Amine | 1H NMR | LC-MS Method 3 |
|---|---|---|---|---|
| 2 | ![structure] | (1S,2S)-2-Benzyloxy-cyclopentylamine | $^1$H NMR (400 MHz, d6-DMSO): δ 8.31 (1H, d, J = 6.9 Hz), 7.93 (1H, m), 7.88-7.74 (6H, m), 7.62 (2H, d, J = 8.5 Hz), 7.34-7.20 (5H, m), 6.62 (1H, d, J = 1.75 Hz), 4.43-4.30 (2H, m), 3.79-3.70 (1H, m), 1.87 (3H, s), 1.78-1.10 (7H, m). | Rt = 5.83 min, m/z = 627.2 [M + H]+, 649.3 (M + Na)+ |
| 3 | ![structure] | 4-Amino-piperidine-1-carboxylic acid benzyl ester | $^1$H NMR (400 MHz, d6-DMSO): δ 8.32 (1H, d, J = 7.2 Hz), 8.02 (1H, m), 7.95-7.90 (2H, m), 7.90-7.79 (4H, m), 7.69-7.62 (2H, m), 7.40-7.26 (5H, m), 6.64 (1H, d, J = 1.76 Hz), 5.05 (2H, s), 3.77-3.63 (2H, m), 3.45 (1H, m), 3.08-2.84 (2H, m), 1.90 (3H, s), 1.65 (1H, m), 1.41 (1H, m), 1.29 (1H, m), 1.07 (1H, m). | Rt = 5.50 min, m/z = 670.3 [M + H]+ |

-continued

| Ex | Structure | Amine | 1H NMR | LC-MS Method 3 |
|---|---|---|---|---|
| 4 | 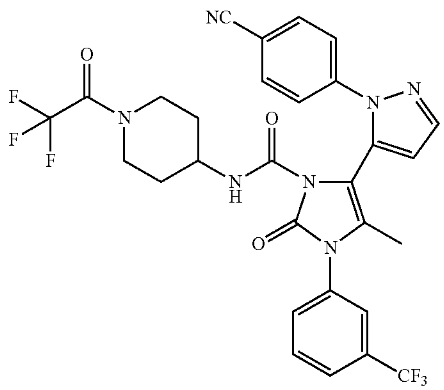 [SMILES: Cc1c(-c2ccnn2-c2ccc(C#N)cc2)n(C(=O)NC2CCN(C(=O)C(F)(F)F)CC2)c(=O)n1-c1cccc(C(F)(F)F)c1] | 1-(4-Amino-piperidin-1-yl)-2,2,2-trifluoro-ethanone | ¹H NMR (400 MHz, d6-DMSO): δ 8.34 (1H, d, J = 7.2 Hz), 8.01 (1H, m), 7.95-7.90 (2H, m), 7.90-7.78 (4H, m), 7.69-7.63 (2H, m), 6.64 (1H, d, J = 1.75 Hz), 3.98 (1H, m), 3.73-3.53 (2H, m), 3.35-3.22 (1H, m), 3.10-2.97 (1H, m), 1.90 (3H, s), 1.77 (1H, m), 1.51 (1H, m), 1.41 (1H, m), 1.26-1.08 (1H, m). | Rt = 5.20 min, m/z = 632.3 [M + H]+ |
| 5 | 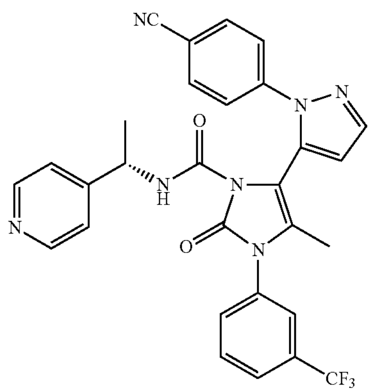 [SMILES: Cc1c(-c2ccnn2-c2ccc(C#N)cc2)n(C(=O)N[C@@H](C)c2ccncc2)c(=O)n1-c1cccc(C(F)(F)F)c1] | (S)-1-Pyridin-4-yl-ethylamine | ¹H NMR (400 MHz, CDCl₃): δ 8.88 (1H, t, J = 7 Hz), 8.59-8.53 (1H, m), 8.53-8.49 (1H, m), 7.82-7.68 (4H, m), 7.65 (1H, bs), 7.62-7.52 (3H, m), 7.43-7.37 (1H, m), 7.15-7.12 (1H, m), 6.99-6.95 (1H, m), 6.55 (0.5H, d, J = 1.77 Hz)*, 6.53 (0.5H, d, J = 1.77 Hz)*, 4.81-4.67 (1H, m), 1.95 (1.5H, s)*, 1.92 (1.5H, s)*, 1.41 (1.5H, d, J = 7 Hz)*, 1.34 (1.5H, d, J = 7 Hz)*. | Rt = 3.81 min, m/z = 558.0 [M + H]+ |
| 6 | 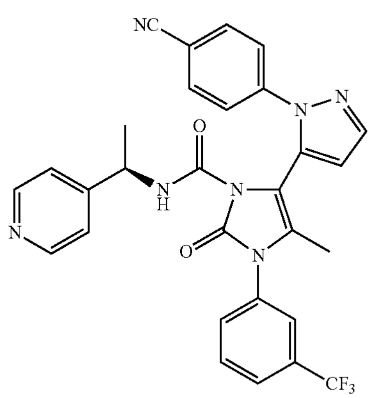 [SMILES: Cc1c(-c2ccnn2-c2ccc(C#N)cc2)n(C(=O)N[C@H](C)c2ccncc2)c(=O)n1-c1cccc(C(F)(F)F)c1] | (R)-1-Pyridin-4-yl-ethylamine | ¹H NMR (400 MHz, CDCl₃): δ 8.88 (1H, t, J = 7 Hz), 8.59-8.53 (1H, m), 8.53-8.49 (1H, m), 7.82-7.68 (4H, m), 7.65 (1H, bs), 7.62-7.52 (3H, m), 7.43-7.37 (1H, m), 7.15-7.12 (1H, m), 6.99-6.95 (1H, m), 6.55 (0.5H, d, J = 1.77 Hz)*, 6.53 (0.5H, d, J = 1.77 Hz)*, 4.81-4.67 (1H, m), 1.95 (1.5H, s)*, 1.92 (1.5H, s)*, 1.41 (1.5H, d, J = 7 Hz)*, 1.34 (1.5H, d, J = 7 Hz)*. | Rt = 3.80 min, m/z = 558.0 [M + H]+ |

| Ex | Structure | Amine | 1H NMR | LC-MS Method 3 |
|---|---|---|---|---|
| 7 | 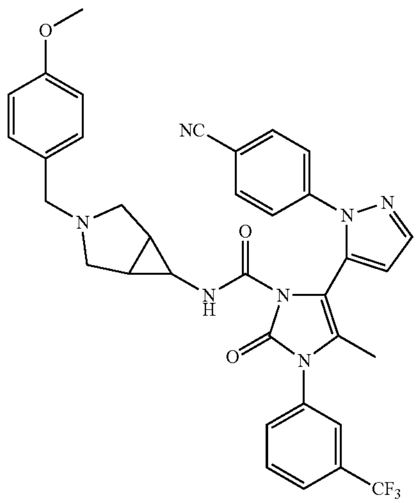 [SMILES: COc1ccc(CN2CC3C(C2)C3NC(=O)n2c(-c3ccnn3-c3ccc(C#N)cc3)c(C)n(-c3cccc(C(F)(F)F)c3)c2=O)cc1] | 3-(4-Methoxy-benzyl)-3-aza-bicyclo[3.1.0]hex-6-ylamine | ¹H NMR (400 MHz, CDCl₃): δ 8.38 (1H, d, J = 3 Hz), 7.80 (1H, d, J = 1.77 Hz), 7.76-7.64 (4H, m), 7.62-7.57 (3H, m), 7.49 (1H, dm, J = 7.9 Hz), 7.13-7.07 (2H, m), 6.82-6.76 (2H, m), 6.54 (1H, d, J = 1.77 Hz), 3.78 (3H, s), 3.50-3.39 (2H, m), 2.97 (2H, dd, J = 8.9 and 2.94 Hz), 2.92 (1H, m), 2.34-2.26 (2H, m), 1.83 (3H, s), 1.47-1.41 (1H, m), 1.30-1.24 (1H, m). | Rt = 3.92 min, m/z = 654.3 [M + H]+ |
| 8 | 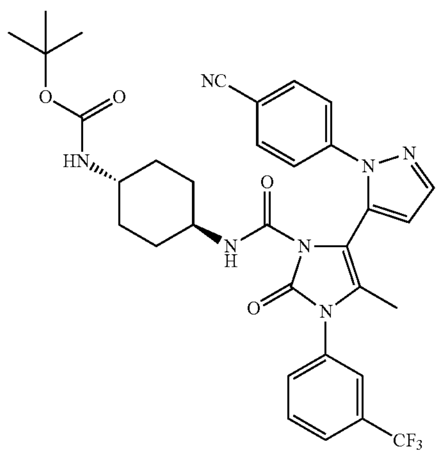 [SMILES: Cc1c(-c2ccnn2-c2ccc(C#N)cc2)n(C(=O)N[C@H]2CC[C@H](NC(=O)OC(C)(C)C)CC2)c(=O)n1-c1cccc(C(F)(F)F)c1] | (Trans-4-amino-cyclohexyl)-carbamic acid tert-butyl ester | ¹H NMR (400 MHz, CDCl₃): δ 8.36 (1H, d, J = 7.5 Hz), 7.80 (1H, d, J = 1.7 Hz), 7.78-7.66 (4H, m), 7.62-7.58 (3H, m), 7.55-7.50 (1H, m), 6.55 (1H, d, J = 1.8 Hz), 4.32-4.32 (1H, bs), 3.48-3.36 (2H, m), 1.98-1.90 (3H, m), 1.87 (3H, s), 1.82-1.73 (1H, m), 1.41 (9H, s), 1.30-1.07 (4H, m). | Rt = 5.52 min, m/z = 650.3 [M + H]+, 672.3 [M + Na]+ |
| 9 | 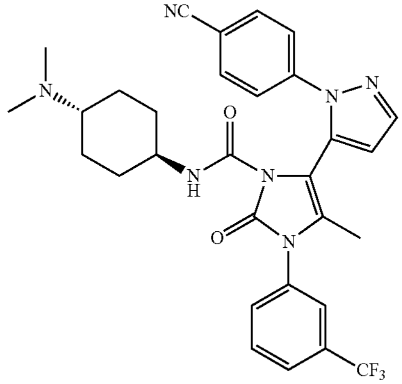 [SMILES: Cc1c(-c2ccnn2-c2ccc(C#N)cc2)n(C(=O)N[C@H]2CC[C@H](N(C)C)CC2)c(=O)n1-c1cccc(C(F)(F)F)c1] | N,N-Dimethyl-trans-cyclohexane-1,4-diamine | ¹H NMR (400 MHz, CDCl₃): δ 8.30 (1H, d, J = 7.5 Hz), 7.81 (1H, d, J = 1.8 Hz), 7.78-7.66 (4H, m), 7.64-7.57 (3H, m), 7.52 (1H, dm, J = 7.8 Hz), 6.55 (1H, d, J = 1.8 Hz), 3.46-3.35 (1H, m), 2.24 (6H, s), 2.14-2.04 (1H, m), 2.00-1.94 (1H, m), 1.91-1.75 (3H, m), 1.89 (3H, s), 1.31-0.99 (4H, m). | Rt = 3.80 min, m/z = 578.3 [M + H]+ |

-continued

| Ex | Structure | Amine | 1H NMR | LC-MS Method 3 |
|---|---|---|---|---|
| 10 | 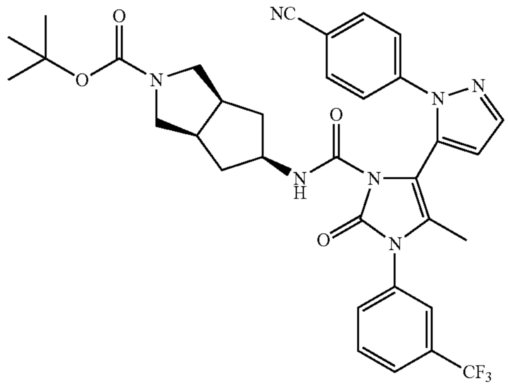 [SMILES: Cc1c(-c2ccnn2-c2ccc(C#N)cc2)n(C(=O)N[C@@H]2C[C@@H]3CN(C(=O)OC(C)(C)C)C[C@@H]3C2)c(=O)n1-c1cccc(C(F)(F)F)c1] | (3aS,5R,6aR)-5-Amino-hexahydro-cyclopenta[c]pyrrole-2-carboxylic acid tert-butyl ester | $^1$H NMR (400 MHz, CDCl$_3$): δ 8.52 (1H, d, J = 7.3 Hz), 7.81 (1H, d, J = 1.8 Hz), 7.78-7.65 (4H, m), 7.63-7.57 (3H, m), 7.55-7.49 (1H, m), 6.55 (1H, d, J = 1.8 Hz), 4.02-3.85 (1H, m), 3.47-3.36 (2H, m), 3.21-3.21 (2H, m), 2.60-2.47 (2H, m), 2.32-2.20 (2H, m), 2.20-2.10 (1H, m), 1.88 (3H, s), 1.43 (9H, s), 1.30-1.10 (2H, m). | Rt = 5.66 min, m/z = 662.5 [M + H]+, m/z 684.4 [M + Na]+ |
| 11 | 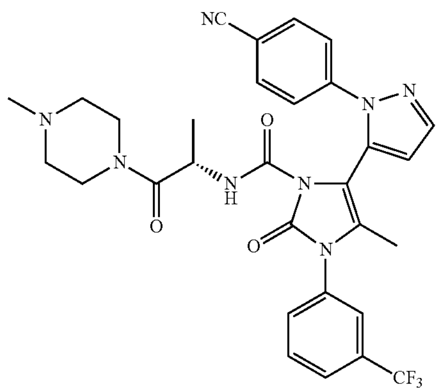 [SMILES: Cc1c(-c2ccnn2-c2ccc(C#N)cc2)n(C(=O)N[C@@H](C)C(=O)N2CCN(C)CC2)c(=O)n1-c1cccc(C(F)(F)F)c1] | (S)-2-Amino-1-(4-methyl-piperazin-1-yl)-propan-1-one | $^1$H NMR (400 MHz, d6-DMSO): δ 9.04 (0.6H, d, J = 6.6 Hz)*, 8.84 (0.4H, d, J = 7.2 Hz)*, 8.07-8.00 (1H, m), 7.97-7.78 (6H, m), 7.66 (2H, m), 6.67-6.62 (1H, m)*, 4.46 (0.6H, quintet, J = 6.6 Hz)*, 4.38 (0.4H, quintet, J = 6.8 Hz)*, 3.54-3.30 (4H, m), 2.31-2.16 (4H, s), 2.19 (1.2H, s)*, 2.14 (1.8H, s)*, 1.92 (1.8H, s)*, 1.88 (1.2H, s)*, 1.09 (1.2H, d, J = 6.7 Hz)*, 0.83 (1.8H, d, J = 6.7 Hz)*. | Rt = 3.71 min, m/z = 607.4 [M]+ |
| 12 | 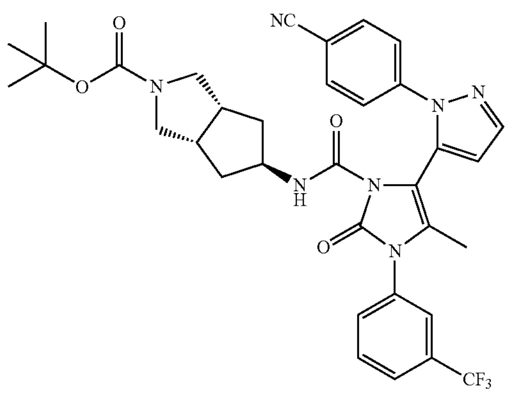 [SMILES: Cc1c(-c2ccnn2-c2ccc(C#N)cc2)n(C(=O)N[C@H]2C[C@@H]3CN(C(=O)OC(C)(C)C)C[C@@H]3C2)c(=O)n1-c1cccc(C(F)(F)F)c1] | (3aR,5S,6aS)-5-Amino-hexahydro-cyclopenta-[c]pyrrole-2-carboxylic acid tert-butyl ester | $^1$H NMR (400 MHz, CDCl$_3$): δ 8.44 (1H, d, J = 6.8 Hz), 7.81 (1H, d, J = 1.8 Hz), 7.77 (1H, dm, J = 8.2 Hz), 7.74-7.66 (3H, m), 7.62 (1H, m), 7.61-7.56 (2H, m), 7.53 (1H, dm, J = 7.8 Hz), 6.56 (1H, d, J = 1.8 Hz), 4.11 (1H, ddd, J = 13.0, 13.0, 6.9 Hz), 3.58-3.37 (2H, m), 3.20-2.97 (2H, m), 2.77-2.62 (2H, m), 1.89 (3H, s), 1.83-1.65 (3H, m), 1.58-1.48 (1H, m), 1.43 (9H, s). | Rt = 5.68 min, m/z = 662.4 [M + H]+, 684.4 [M + Na]+ |
| 13 | 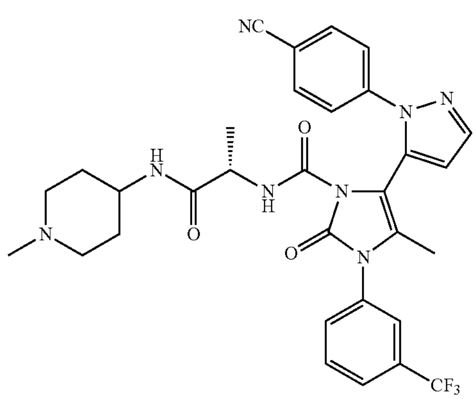 [SMILES: Cc1c(-c2ccnn2-c2ccc(C#N)cc2)n(C(=O)N[C@@H](C)C(=O)NC2CCN(C)CC2)c(=O)n1-c1cccc(C(F)(F)F)c1] | (S)-2-Amino-N-(1-methyl-piperidin-4-yl)-propion-amide | $^1$H NMR (400 MHz, d6-DMSO): δ 8.83 (0.6H, d, J = 6.8 Hz)*, 8.80 (0.4H, d, J = 7.2 Hz)*, 8.04 (1H, m), 7.98-7.79 (7H, m), 7.69-7.62 (2H, m), 6.66-6.62 (1H, m), 3.99-3.90 (1H, m), 3.50-3.35 (1H, m), 2.79-2.61 (2H, m)*, 2.20-2.09 (3H, m)*, 2.03-1.88 (2H, m), 1.90 (2H, s), 1.87 (1H, s)*, 1.71-1.59 (2H, m), 1.42-1.27 (2H, m), 1.11 (1H, d, J = 6.7 Hz)*, 0.88-0.83 (2H, d, J = 6.7 Hz)*. | Rt = 3.68 min, m/z = 621.3 [M + H]+ |

| Ex | Structure | Amine | 1H NMR | LC-MS Method 3 |
|---|---|---|---|---|
| 14 | 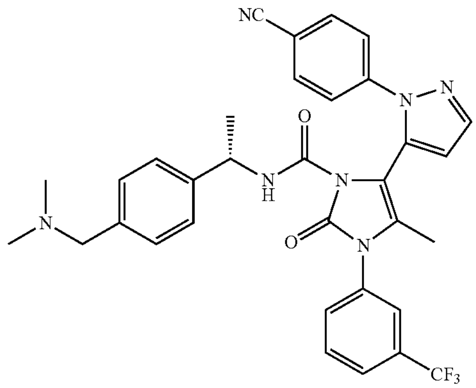 [SMILES: Cc1c(-c2ccnn2-c2ccc(C#N)cc2)n(C(=O)N[C@@H](C)c2ccc(CN(C)C)cc2)c(=O)n1-c1cccc(C(F)(F)F)c1] | (S)-1-(4-Dimethylaminomethyl-phenyl)-ethylamine | $^1$H NMR (400 MHz, d6-DMSO): δ 8.71 (0.5H, d, J = 7.5 Hz)*, 8.65 (0.5H, d, J = 7.7 Hz)*, 8.03 (1H, m), 7.94 (1H, d, J = 8.2 Hz), 7.92-7.74 (5H, m), 7.68 (1H, d, J = 8.3 Hz), 7.57 (1H, d, J = 8.4 Hz), 7.21-7.15 (3H, m), 6.95 (1H, d, J = 7.9 Hz), 6.63 (1H, d, J = 6.1 Hz), 4.65-4.50 (1H, m), 3.38 (2H, m), 2.14 (3H, s), 2.09 (3H, s), 1.91 (3H, s), 1.32 (1.6H, d, J = 6.8 Hz)*, 1.13 (1.4H, d, J = 6.7 Hz)*. | Rt = 3.96 min, m/z = 614.3 [M + H]+ |
| 15 | 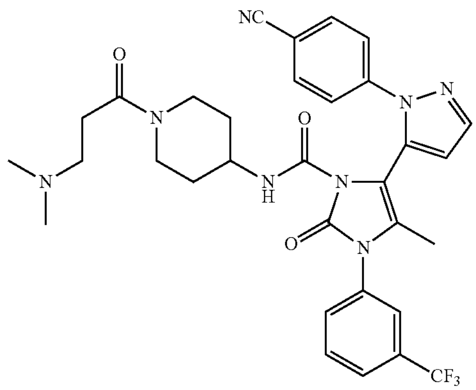 [SMILES: Cc1c(-c2ccnn2-c2ccc(C#N)cc2)n(C(=O)NC2CCN(C(=O)CCN(C)C)CC2)c(=O)n1-c1cccc(C(F)(F)F)c1] | 1-(4-Amino-piperidin-1-yl)-3-dimethyl-amino-propan-1-one | $^1$H NMR (400 MHz, d6-DMSO): δ 8.33 (1H, d, J = 7.1 Hz), 8.02 (1H, m), 7.96-7.83 (5H, m), 7.82 (1H, t, J = 8.0 Hz), 7.69-7.62 (2H, m), 6.64 (1H, d, J = 1.8 Hz), 3.99-3.86 (1H, m), 3.71-3.43 (2H, m), 3.15-3.01 (1H, m), 2.87-2.69 (1H, m), 2.41 (4H, s), 2.12 (6H, s), 1.90 (3H, s), 1.77-1.57 (1H, m), 1.50-0.89 (3H, m). | Rt = 3.74 min, m/z = 635.4 [M + H]+ |
| 16 | 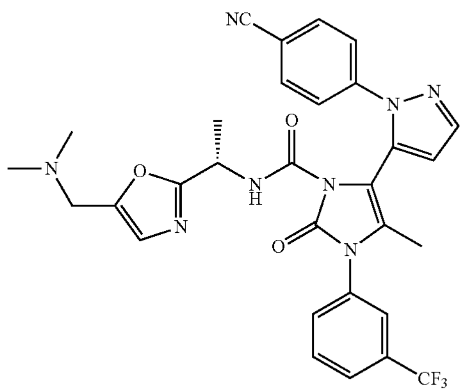 [SMILES: Cc1c(-c2ccnn2-c2ccc(C#N)cc2)n(C(=O)N[C@@H](C)c2ncc(CN(C)C)o2)c(=O)n1-c1cccc(C(F)(F)F)c1] | Intermed. D | $^1$H NMR (400 MHz, d6-DMSO): δ 8.99-8.94 (1H, m), 8.04 (1H, s), 7.96-7.80 (6H, m), 7.70-7.60 (2H, m), 6.91 (1H, apparent d J = 7.3 Hz), 6.64 (1H, s), 4.72 (1H, quintet J = 7.1 Hz), 3.41 (2H, apparent d J = 9.1 Hz), 2.12 and 2.09 (6H, 2xs)*, 1.90 and 1.87 (3H, 2xs)*, 1.33 and 1.16 (3H, 2xd J = 6.7 Hz)*. | Rt = 3.70 min, m/z = 605.4 [M + H]+ |
| 17 | 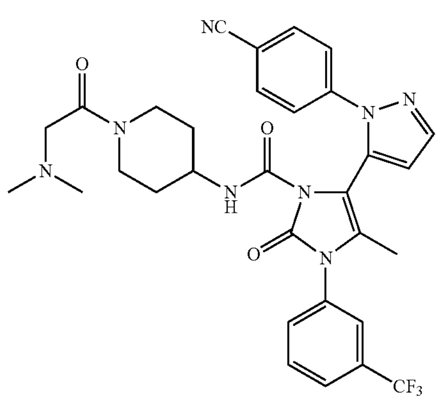 | 1-(4-Amino-piperidin-1-yl)-2-dimethyl-amino-ethanone | $^1$H NMR (400 MHz, d6-DMSO): δ 10.32 (0.3H, s)*, 8.30 (0.7H, d, J = 7.1 Hz)*, 7.95-7.78 (6H, m), 7.74-7.62 (3H, m), 6.68 (0.3H, d J = 1.8 Hz)*, 6.61 (0.7H, d J = 1.8 Hz)*, 3.90-3.74 (2H, m), 3.58-3.50 (1H, m), 3.08-3.0 (peaks obscured by water), 2.18 and 2.17 (6H, 2s)*, 1.86 (2H, s)*, 1.70 (1H, s)*, 1.69-1.40 (2H, m), 1.30-1.10 (1H, m). | Rt = 3.70 min, m/z = 621.3 [M + H]+ |

| Ex | Structure | Amine | 1H NMR | LC-MS Method 3 |
|---|---|---|---|---|
| 18 | 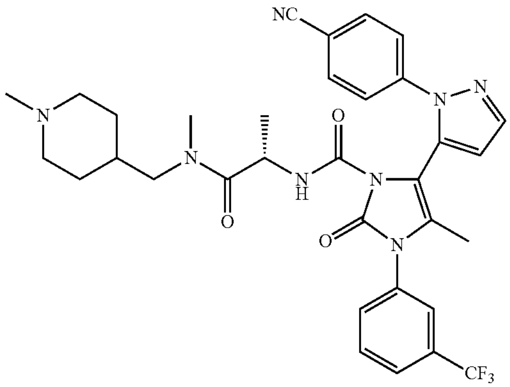 [SMILES: Cc1c(-c2ccnn2-c2ccc(C#N)cc2)n(C(=O)N[C@@H](C)C(=O)N(C)CC2CCN(C)CC2)c(=O)n1-c1cccc(C(F)(F)F)c1] | (S)-2-Amino-N-methyl-N-(1-methyl-piperidin-4-ylmethyl)-propion-amide | ¹H NMR (400 MHz, d6-DMSO at 80° C.): δ 8.86 (1H, br s), 7.92 (1H, s), 7.88-7.78 (6H, m), 7.65 (2H, d J = 8.8 Hz), 6.61 (1H, d J = 1.7 Hz), 4.45 (1H, quintet J = 6.7 Hz), 3.22 (1H,br s), 3.10-3.00 (1H, peaks partially obscured by water), 2.92-2.76 (3H, m), 2.74-2.62 (2H, m), 2.12 (3H, br s), 1.88-1.74 (5H, m), 1.56-1.38 (3H, m), 1.22-0.88 (5H, m) | Rt = 3.74 min, m/z = 649.5 [M + H]+ |
| 19 | 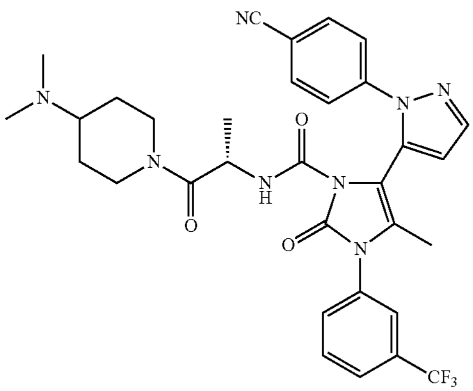 [SMILES: Cc1c(-c2ccnn2-c2ccc(C#N)cc2)n(C(=O)N[C@@H](C)C(=O)N2CCC(N(C)C)CC2)c(=O)n1-c1cccc(C(F)(F)F)c1] | (S)-2-Amino-1-(4-dimethyl-amino-piperidin-1-yl)-propan-1-one | ¹H NMR (400 MHz, d6-DMSO): δ 9.10-8.80 (1H, 4xd)*, 8.05-8.00 (1H, m), 7.95-7.75 (6H, m), 7.72-7.62 (2H, m), 6.66-6.62 (1H, m), 4.52-4.36 (1H, m), 4.32-4.16 (1H, m), 3.76-3.60 (1H, m), 3.05-2.80 (1H, m), 2.70-2.55 (1H, m), 2.35-2.21 (1H, m), 2.20-2.16 (6H, m), 1.95-1.84 (3H, m), 1.76-1.64 (2.4H, m)*, 1.35-1.05 (4H, m), 0.87-0.78 (1.6H, m)*. | Rt = 3.70 min, m/z- 635.4 [M]+ |
| 20 | 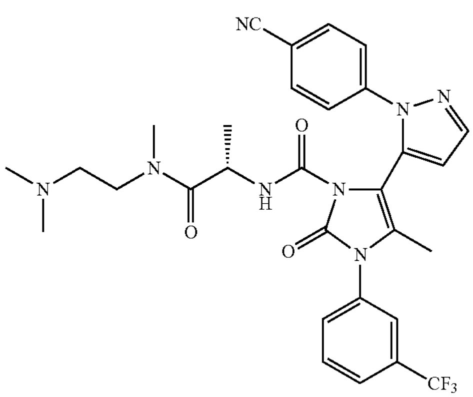 [SMILES: Cc1c(-c2ccnn2-c2ccc(C#N)cc2)n(C(=O)N[C@@H](C)C(=O)N(C)CCN(C)C)c(=O)n1-c1cccc(C(F)(F)F)c1] | (S)-2-Amino-N-(2-dimethyl-amino-ethyl)-N-methyl-propion-amide | ¹H NMR (400 MHz, d6-DMSO): δ 8.85 (1H, br s), 7.94-7.90 (1H, m), 7.89-7.77 (5H, m), 7.75-7.61 (3H, m), 6.61 (1H, d J = 1.8 Hz), 4.50-4.40 (1H, m), 3.50-3.20 (2H, m), 2.87 (3H, br s), 2.32 (2H, t J = 6.6 Hz), 2.12 (6H, s) 1.85 (3H, br s), 1.20-0.85 (3H, br m). | Rt = 3.67 min, m/z = 609.4 [M + H]+ |
| 21 | 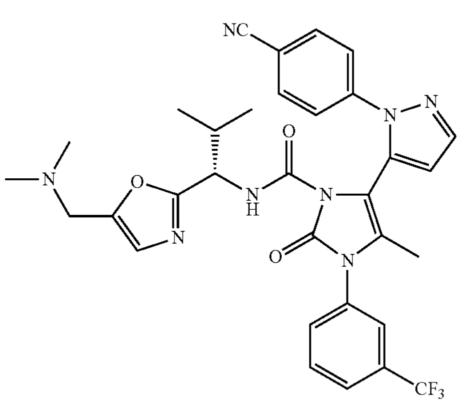 [SMILES: Cc1c(-c2ccnn2-c2ccc(C#N)cc2)n(C(=O)N[C@H](c2ncc(CN(C)C)o2)C(C)C)c(=O)n1-c1cccc(C(F)(F)F)c1] | Intermed. E | ¹H NMR (400 MHz, d6-DMSO): δ 9.09 (d, 0.6H, J = 8.75 Hz)*, 8.95 (d, 0.4H, J = 8.44 Hz)*, 8.07 (s, 1H), 7.96-7.74 (m, 5H), 7.66 (d, 1H, J = 8.65 Hz), 7.58 (d, 1H, J = 8.55 Hz), 6.92 (s, 1H), 6.67-6.61 (m, 1H), 4.54-4.44 (m, 1H), 3.50-3.39 (m, 2H), 2.15-2.05 (m, 6H), 1.97-1.81 (m, 4H), 0.76 (d, 2H, apparent dd, J = 6.71), 0.62 (d, 2H, J = 6.76 Hz), 0.55 (d, 2H, J = 6.72 Hz). | Rt = 3.89 min, m/z = 633.4 [M + H]+ |

-continued

| Ex | Structure | Amine | 1H NMR | LC-MS Method 3 |
|----|-----------|-------|--------|----------------|
| 22 | 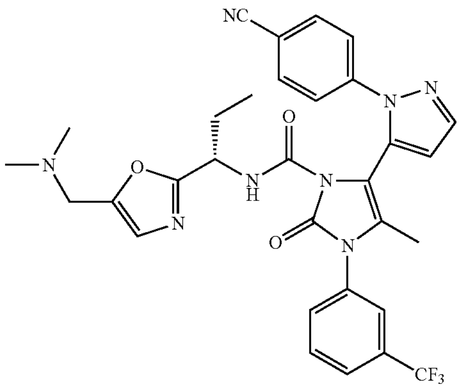 [SMILES: CC[C@H](NC(=O)n1c(-c2ccnn2-c2ccc(C#N)cc2)c(C)n(-c2cccc(C(F)(F)F)c2)c1=O)c1ncc(CN(C)C)o1] | Intermed. F | ¹H NMR (400 MHz, d6-DMSO): δ 9.01 (d, 0.6H, J = 7.74 Hz)*, 8.94 (d, 0.4H, J = 7.72 Hz)*, 8.06 (s, 1H), 7.97-7.78 (m, 5H), 7.67 (d, 1H, J = 8.58 Hz), 7.61 (d, 1H, J = 8.47 Hz), 6.92 (s, 1H), 6.65 (d, 1H, J = 1.75 Hz), 4.65-4.56 (m, 1H), 3.48-3.38 (m, 2H), 2.15-2.04 (m, 6H), 1.96-1.84 (m, 3H), 1.83-1.63 (m, 1H), 1.63-1.44 (m, 1H), 0.72 (t, 1H, J = 7.17 Hz), 0.52 (t, 2H, J = 7.26 Hz). | Rt = 3.78 min, m/z = 619.3 [M + H]+ |
| 23 | 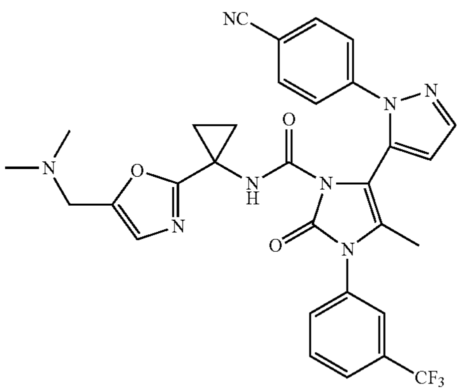 [SMILES: Cc1c(-c2ccnn2-c2ccc(C#N)cc2)n(C(=O)NC2(c3ncc(CN(C)C)o3)CC2)c(=O)n1-c1cccc(C(F)(F)F)c1] | Intermed. G | ¹H NMR (400 MHz, d6-DMSO): δ 9.09 (s, 1H), 8.04 (s, 1H), 7.95-7.82 (m, 6H), 7.64 (d, 2H, J = 8.83 Hz), 6.80 (s, 1H), 6.64 (d, 1H, J = 1.76), 3.32 (s, 2H), 2.07 (s, 6H), 1.89 (s, 3H), 1.32-1.21 (m, 2H), 1.20-1.09 (m, 1H), 0.77-0.65 (m, 1H). | Rt = 3.66 min, m/z = 617.3 [M + H]+ |
| 24 | 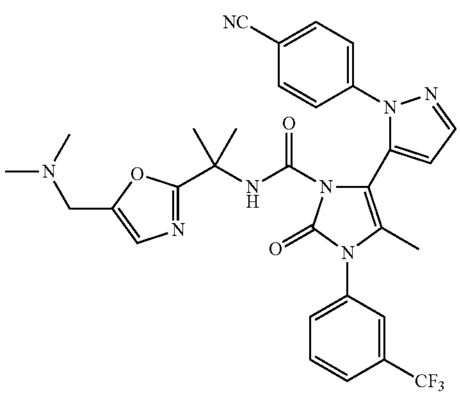 [SMILES: Cc1c(-c2ccnn2-c2ccc(C#N)cc2)n(C(=O)NC(C)(C)c2ncc(CN(C)C)o2)c(=O)n1-c1cccc(C(F)(F)F)c1] | Intermed. H | ¹H NMR (400 MHz, d6-DMSO): δ 9.12 (s, 1H), 8.06 (br s, 1H), 7.94-7.80 (m, 6H), 7.61 (d, 2H, J = 8.32 Hz), 6.83 (s, 1H), 6.60 (d, 1H, J = 1.75 Hz), 3.37 (s, 2H), 2.06 (s, 6H), 1.90 (s, 3H), 1.35 (d, 6H, J = 7.56 Hz). | Rt = 3.74 min, m/z = 619.3 [M + H]+ |
| 25 | 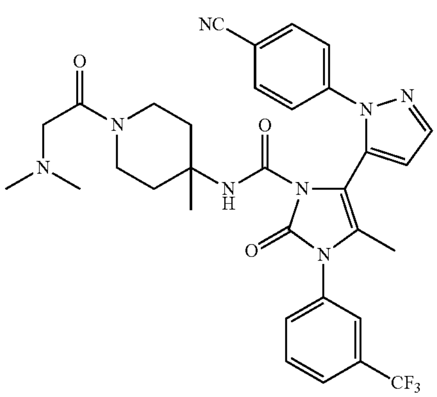 [SMILES: Cc1c(-c2ccnn2-c2ccc(C#N)cc2)n(C(=O)NC2(C)CCN(C(=O)CN(C)C)CC2)c(=O)n1-c1cccc(C(F)(F)F)c1] | Intermed. M | ¹H NMR (400 MHz, d6-DMSO): δ 8.47 (d, 1H, J = 23.78 Hz), 8.04 (s, 1H), 7.96-7.79 (m, 5H), 7.64 (d, 2H, J = 8.58 Hz), 6.64 (d, 1H, J = 1.69 Hz), 5.76 (s, 1H), 3.88 (dd, 1H, J = 42.07, 13.06 Hz), 3.75-3.55 (m, 1H), 3.31-3.25 (m, 1H), 3.16-2.87 (m, 2H), 2.65 (q, 1H, J = 13.37 Hz), 2.13 (d, 6H, J = 13.29 Hz), 1.95 (s, 3H), 1.83-1.66 (m, 1H), 1.66-1.53 (m, 1H), 1.42-1.13 (m, 2H), 1.01 (s, 3H). | Rt = 3.79 min, m/z = 635.3 [M + H]+ |

-continued

| Ex | Structure | Amine | 1H NMR | LC-MS Method 3 |
|----|-----------|-------|--------|----------------|
| 26 | 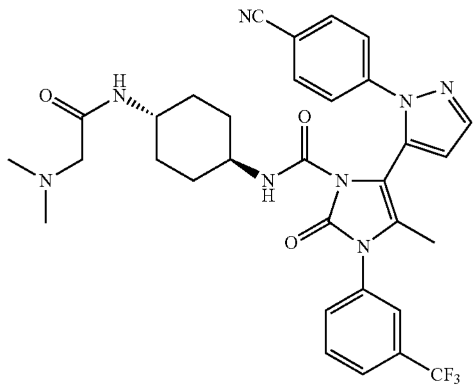 [SMILES: Cc1c(-c2ccnn2-c2ccc(C#N)cc2)n(C(=O)N[C@H]2CC[C@H](NC(=O)CN(C)C)CC2)c(=O)n1-c1cccc(C(F)(F)F)c1] | N-(Trans-4-amino-cyclohexyl)-2-dimethyl-amino-acetamide | $^1$H NMR (400 MHz, d6-DMSO): δ 8.20 (1H, d, J = 7.48 Hz), 8.01 (1H, s), 7.94-7.78 (6H, m), 7.66 (2H, d, J = 8.78 Hz), 7.45 (1H, d, J = 8.37 Hz), 6.63 (1H, d, J = 1.75 Hz), 3.59-3.42 (1H, m), 3.23-3.08 (1H, m), 2.79 (2H, s), 2.16 (6H, s), 1.88 (3H, s), 1.77-1.56 (3H, m), 1.46-1.34 (1H, m), 1.33-1.13 (3H, m), 1.11-0.96 (1H, m). | Rt = 3.72 min, m/z = 635.3 [M + H]+ |
| 27 | 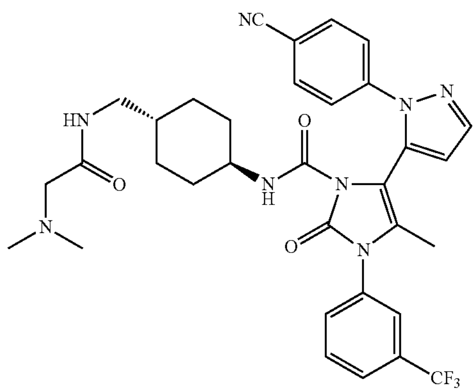 [SMILES: Cc1c(-c2ccnn2-c2ccc(C#N)cc2)n(C(=O)N[C@H]2CC[C@H](CNC(=O)CN(C)C)CC2)c(=O)n1-c1cccc(C(F)(F)F)c1] | Intermed. N | $^1$H NMR (400 MHz, d6-DMSO): δ 8.17 (1H, d, J = 7.51 Hz), 8.01 (1H, s), 7.93-7.78 (6H, m), 7.70-7.62 (3H, m), 6.63 (1H, d, J = 1.76 Hz), 3.17-3.06 (1H, m), 2.89 (2H, t, J = 6.38 Hz), 2.81 (2H, s), 2.17 (6H, s), 1.89 (3H, s), 1.75-1.65 (1H, m), 1.58 (2H, br s), 1.46-1.26 (2H, m), 1.15-1.00 (1H, m), 0.95-0.76 (3H, m). | Rt = 3.85 min, m/z- 649.4 [M + H]+ |
| 28 | 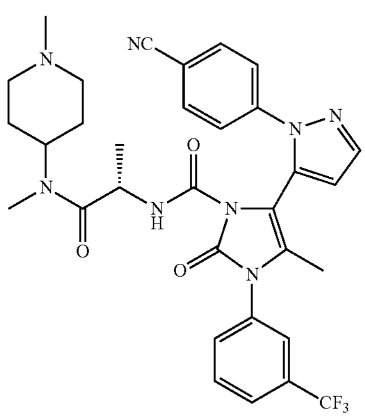 [SMILES: Cc1c(-c2ccnn2-c2ccc(C#N)cc2)n(C(=O)N[C@@H](C)C(=O)N(C)C2CCN(C)CC2)c(=O)n1-c1cccc(C(F)(F)F)c1] | (S)-2-Amino-N-methyl-N-(1-methyl-piperidin-4-yl)-propion-amide | $^1$H NMR (400 MHz, d6-DMSO): δ 9.08 (0.2H, d, J = 6.64 Hz)*, 9.03 (0.3H, d, J = 6.66 Hz)*, 8.90 (0.2H, d, J = 7.41 Hz)*, 8.82 (0.3H, d, J = 7.37 Hz)*, 8.03 (1H, s), 7.97-7.79 (7H, m), 7.71-7.60 (2H, m), 6.63 (1H, s), 4.50-4.31 (1H, m), 4.15-4.02 (1H, m), 3.31 (3H, s), 2.87-2.62 (5H, m), 2.19-2.08 (3H, m), 2.00-1.44 (8H, m), 1.42-1.21 (2H, m), 1.16-1.05 (1.5H, m)*, 0.82 (1.5H, d, J = 6.62 Hz)*. | Rt = 3.64 min, m/z = 635.3 [M + H]+ |

Example 29. (Trans-4-{[5-[2-(4-cyano-phenyl)-2H-pyrazol-3-yl]-4-methyl-2-oxo-3-(3-trifluoromethyl-phenyl)-2,3-dihydro-imidazole-1-carbonyl]-amino}-cyclohexylmethyl)-trimethyl-ammonium benzene sulfonate

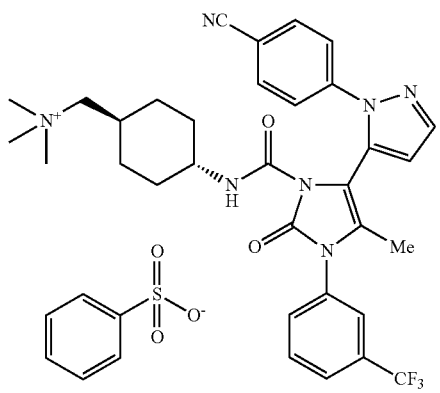 [SMILES: Cc1c(-c2ccnn2-c2ccc(C#N)cc2)n(C(=O)N[C@H]2CC[C@H](C[N+](C)(C)C)CC2)c(=O)n1-c1cccc(C(F)(F)F)c1 ; O=S(=O)([O-])c1ccccc1]

A solution of Example 1 (120 mg, 0.2 mmol) in THF (0.25 mL) was treated with methyl benzenesulfonate (38 mg, 30 uL, 0.22 mmol). The mixture was stirred for 3 days at ambient temperature. The resultant white mass was diluted with diethyl ether (4 mL) and stirred for 30 min. The solid was recovered by filtration and freeze-dried from acetonitrile/water to afford the title compound (150 mg, 0.19 mmol, 95%).

LCMS (Method 3): Rt=3.90 min, m/z 606.4 [M]+

$^1$H NMR (400 MHz, CDCl$_3$): δ 8.32 (1H, d, J=7.4 Hz), 7.87-7.82 (2H, m), 7.81 (1H, d, J=1.8 Hz), 7.78-7.74 (1H, m), 7.74-7.67 (3H, m), 7.63 (1H, m), 7.61-7.56 (2H, m), 7.54 (1H, dm, J=7.8 Hz), 7.37-7.29 (3H, m), 6.55 (1H, d, J=1.8 Hz), 3.39-3.20 (3H, m), 3.30 (9H, s), 1.95-1.69 (5H, m), 1.89 (3H, s), 1.27-1.06 (4H, m).

Example 30. Benzyl-(trans-4-{[5-[2-(4-cyano-phenyl)-2H-pyrazol-3-yl]-4-methyl-2-oxo-3-(3-trifluoromethyl-phenyl)-2,3-dihydro-imidazole-1-carbonyl]-amino}-cyclohexylmethyl)-dimethyl-ammonium bromide

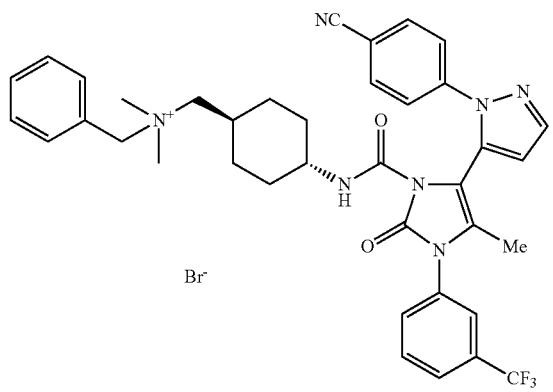 [SMILES: Cc1c(-c2ccnn2-c2ccc(C#N)cc2)n(C(=O)N[C@H]2CC[C@H](C[N+](C)(C)Cc3ccccc3)CC2)c(=O)n1-c1cccc(C(F)(F)F)c1 ; [Br-]]

A solution of Example 1 (120 mg, 0.2 mmol) in THF (0.25 mL) was treated with benzyl bromide (38 mg, 27 uL, 0.22 mmol). The mixture was stirred for 3 days at ambient temperature then diluted with diethyl ether (3 mL) causing a white solid to form. The mixture was stirred for 30 min. then the solid was recovered by filtration. It was freeze-dried from acetonitrile/water to afford the title compound (140 mg, 0.18 mmol, 90%).

LCMS (Method 3): Rt=4.25 min, m/z 682.5 [M]+

$^1$H NMR (400 MHz, CDCl$_3$): δ 8.34 (1H, d, J=7.3 Hz), 7.81 (1H, d, J=1.8 Hz), 7.78-7.67 (4H, m), 7.67-7.56 (5H, m), 7.54 (1H, dm, J=8.1 Hz), 7.50-7.38 (3H, m), 6.55 (1H, d, J=1.8 Hz), 5.10-5.00 (2H, m), 3.62-3.55 (1H, m), 3.46-3.30 (2H, m), 3.27 (3H, s), 3.24 (3H, s), 2.07-1.83 (4H, m), 1.89 (3H, s), 1.79-1.69 (1H, m), 1.34-1.14 (4H, m).

Example 31. (Trans-4-{[5-[2-(4-cyano-phenyl)-2H-pyrazol-3-yl]-4-methyl-2-oxo-3-(3-trifluoromethyl-phenyl)-2,3-dihydro-imidazole-1-carbonyl]-amino}-cyclohexylmethyl)-ethyl-dimethyl-ammonium benzene sulfonate

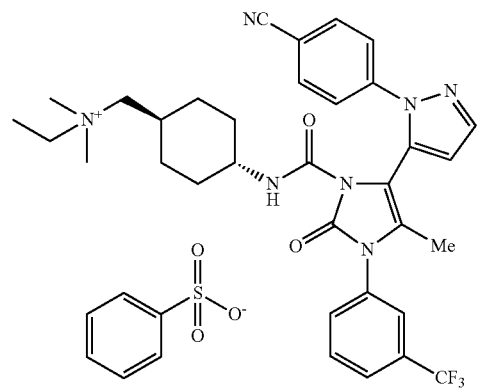 [SMILES: CC[N+](C)(C)C[C@H]1CC[C@H](NC(=O)n2c(-c3ccnn3-c3ccc(C#N)cc3)c(C)n(-c3cccc(C(F)(F)F)c3)c2=O)CC1 ; O=S(=O)([O-])c1ccccc1]

A solution of Example 1 (120 mg, 0.2 mmol) in THF (0.25 mL) was treated with ethyl benzenesulfonate (38 mg, 30 uL, 0.22 mmol). The mixture was stirred for 3 days at ambient temperature then at 50° C. for a further 3 days giving a thick white mass. The mixture was then cooled to ambient temperature and triturated with diethyl ether (3 mL). The residue was freeze-dried from acetonitrile/water to afford the title compound; (140 mg, 0.18 mmol, 90%).

LCMS (Method 3): Rt=3.93 min, m/z 620.4 [M]+

$^1$H NMR (400 MHz, CDCl$_3$): δ 8.32 (1H, d, J=7.3 Hz), 7.88-7.83 (2H, m), 7.81 (1H, d, J=1.8 Hz), 7.78-7.66 (4H, m), 7.64-7.56 (3H, m), 7.56-7.51 (1H, m), 7.36-7.30 (3H, m), 6.55 (1H, d, J=1.8 Hz), 3.60-3.51 (2H, m), 3.42-3.14 (4H, m), 3.22 (3H, s), 3.21 (3H, s), 1.95-1.69 (4H, m), 1.89 (3H, s), 1.32 (3H, t, J=7.0 Hz), 1.28-1.02 (4H, m).

The following compounds were prepared by analogous procedures to that used in Examples 1, 29, 30 and 31. In the table below where rotameric signals have been identified in the NMR spectrum these have been labelled by *.

| Ex. | Structure | Amine | Quat. Method | 1H NMR | LC-MS Method 3 |
|---|---|---|---|---|---|
| 32 | 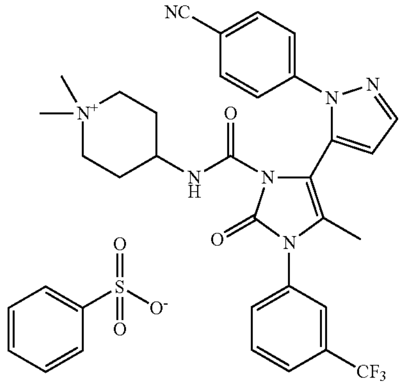 [SMILES: O=S(=O)([O-])c1ccccc1 ; Cc1c(-c2ccnn2-c2ccc(C#N)cc2)n(C(=O)NC2CC[N+](C)(C)CC2)c(=O)n1-c1cccc(C(F)(F)F)c1] | 1-Methyl-piperidin-4-ylamine | Ex 29 | $^1$H NMR (400 MHz, d6-DMSO): δ 8.36 (1H, d, J = 7.7 Hz), 8.01 (1H, m), 7.94-7.80 (6H, m), 7.70-7.63 (2H, m), 7.61-7.56 (2H, m), 7.35-7.25 (3H, m), 6.65 (1H, d, J = 1.76 Hz), 3.54 (1H, m), 3.38-3.23 (4H, m), 3.04 (6H, s), 1.97-1.83 (1H, m), 1.92 (3H, s), 1.82-1.64 (2H, m), 1.54-1.43 (1H, m). | Rt = 3.55 min, no [M]+ observed, m/z = 408.2 [M-side-chain]- |
| 33 | 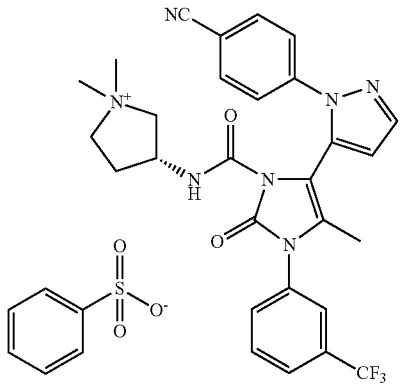 [SMILES: O=S(=O)([O-])c1ccccc1 ; Cc1c(-c2ccnn2-c2ccc(C#N)cc2)n(C(=O)N[C@@H]2CC[N+](C)(C)C2)c(=O)n1-c1cccc(C(F)(F)F)c1] | (R)-1-Methyl-pyrrolidin-3-ylamine | Ex 29 | $^1$H NMR (400 MHz, CDCl$_3$): δ 9.03-8.93 (1H, m)*, 7.88-7.81 (2H, m), 7.79 (1H, bs), 7.76-7.69 (3H, m), 7.68-7.57 (4H, m), 7.53 (1H, tm, J = 7 Hz), 7.34-7.26 (3H, m), 6.61-6.53 (1H, m)*,4.64-4.51 (1H, m), 4.01-3.83 (2H, m), 3.82-3.61 (2H, m), 3.34 (3H, s), 3.25 (3H, s), 2.62-2.48 (1H, m), 2.16-2.04 (1H, m),1.84-1.75 (3H, m)*. | Rt = 3.53 min, m/z = 550.2 [M]+ |
| 34 | 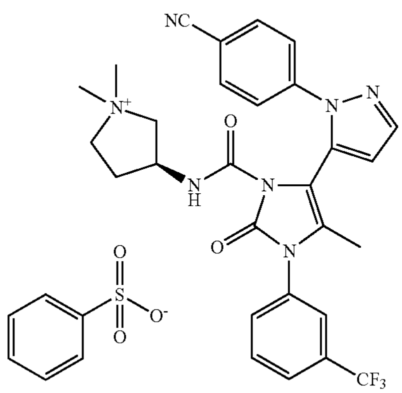 [SMILES: O=S(=O)([O-])c1ccccc1 ; Cc1c(-c2ccnn2-c2ccc(C#N)cc2)n(C(=O)N[C@H]2CC[N+](C)(C)C2)c(=O)n1-c1cccc(C(F)(F)F)c1] | (S)-1-Methyl-pyrrolidin-3-ylamine | Ex 29 | $^1$H NMR (400 MHz, CDCl$_3$): δ 9.03-8.93 (1H, m)*, 7.88-7.81 (2H, m), 7.79 (1H, bs), 7.76-7.69 (3H, m), 7.68-7.57 (4H, m), 7.53 (1H, tm, J = 7 Hz), 7.34-7.26 (3H, m), 6.61-6.53 (1H, m)*, 4.64-4.51 (1H, m), 4.01-3.83 (2H, m), 3.82-3.61 (2H, m), 3.34 (3H, s), 3.25 (3H, s), 2.62-2.48 (1H, m), 2.16-2.04 (1H, m), 1.84-1.75 (3H, m)*. | Rt = 3.5 3 min, m/z = 550.3 [M]+ |
| 35 | 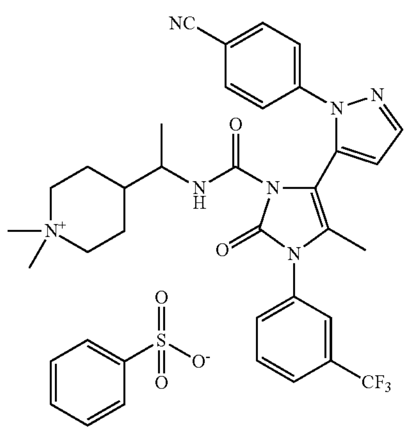 [SMILES: Cc1c(-c2ccnn2-c2ccc(C#N)cc2)n(C(=O)NC(C)C2CC[N+](C)(C)CC2)c(=O)n1-c1cccc(C(F)(F)F)c1 ; O=S(=O)([O-])c1ccccc1] | 1-(1-Methyl-piperidin-4-yl)-ethylamine | Ex 29 | $^1$H NMR (400 MHz, d6-DMSO): δ 8.35-8.28 (0.5H, m)*, 8.15-8.08 (0.5H, m)*, 8.02 (1H, m), 7.98-7.88 (3H, m), 7.88-7.80 (3H, m), 7.69-7.63 (2H, m), 7.61-7.56 (2H, m), 7.34-4.26 (3H, m), 6.64 (1H, d, J = 1.75 Hz), 3.48-3.29 (2H, m), 3.23-3.12 (2H, m), 3.12-2.88 (6H, m), 1.99-1.89 (3H, m), 1.72-1.55 (2H, m), 1.55-1.35 (3H, m), 1.29-1.19 (1H, m), 0.99 (1.5H, d, J = 6 Hz)*, 0.78 (1.5H, d, J = 6 Hz)*. | Rt = 3.73 min, m/z = 592.3 [M]+ |

-continued

| Ex. | Structure | Amine | Quat. Method | 1H NMR | LC-MS Method 3 |
|---|---|---|---|---|---|
| 36 | 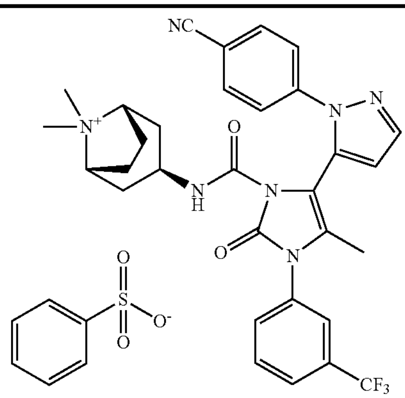 | (1S,3R,5R)-8-Methyl-8-aza-bicyclo[3.2.1]oct-3-ylamine | Ex 29 | $^1$H NMR (400 MHz, CDCl$_3$): δ 9.10 (1H, d, J = 6 Hz), 7.87-7.80 (3H, m), 7.79-7.66 (4H, m), 7.64-7.53 (4H, m), 7.35-7.29 (3H, m), 6.57 (1H, d, J = 1.76 Hz), 4.14 (1H, m), 4.00 (1H, m), 3.92-3.83 (1H, m), 3.32 (3H, s), 3.24 (3H, s), 2.68-2.49 (2H, m), 2.45-2.33 (2H, m), 2.24-2.03 (2H, m), 1.91 (3H, s), 1.84-1.76 (1H, m), 1.64-1.56 (1H, m). | Rt = 3.86 min, m/z = 590.3 [M]+ |
| 37 | 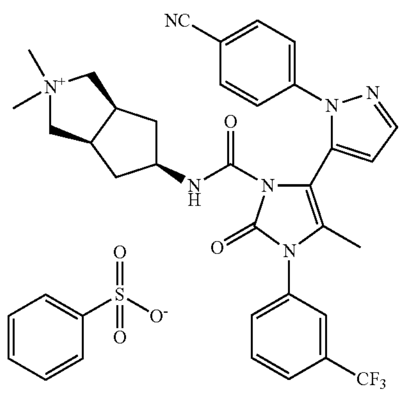 [SMILES: O=S(=O)([O-])c1ccccc1 ; Cc1c(-c2ccnn2-c2ccc(C#N)cc2)n(C(=O)N[C@@H]2C[C@@H]3C[N+](C)(C)C[C@@H]3C2)c(=O)n1-c1cccc(C(F)(F)F)c1] | (3aS,5R,6aR)-2-Methyl-octa-hydrocyclo-penta-[c]pyrrol-5-ylamine | Ex 29 | $^1$H NMR (400 MHz, CDCl$_3$): δ 8.63 (1H, d, J = 6.8 Hz), 7.89-7.82 (2H, m), 7.80 (1H, d, J = 1.8 Hz), 7.78-7.71 (3H, m), 7.69-7.53 (5H, m), 7.30-7.27 (3H, m), 6.57 (1H, d, J = 1.8 Hz), 4.09-3.99 (1H, m), 3.98-3.89 (2H, m), 3.55-3.45 (2H, m), 3.44 (3H, s), 3.17 (3H, s), 3.04-2.90 (2H, m), 2.17-1.98 (2H, m), 1.86 (3H, s), 1.67-1.55 (2H, m). | Rt = 3.75 min, m/z = 590.4 [M]+ |
| 38 | 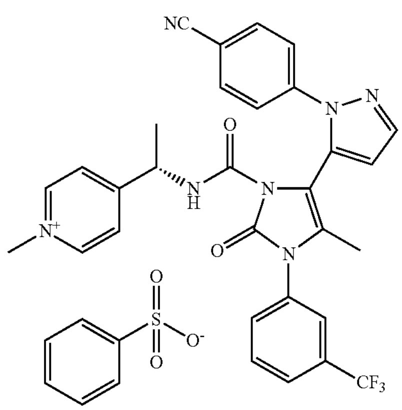 [SMILES: Cc1c(-c2ccnn2-c2ccc(C#N)cc2)n(C(=O)N[C@@H](C)c2cc[n+](C)cc2)c(=O)n1-c1cccc(C(F)(F)F)c1 ; O=S(=O)([O-])c1ccccc1] | See Ex 5 | Ex 29 | $^1$H NMR (400 MHz, d6-DMSO): δ 9.01-8.95 (0.5H, m)*, 8.92-8.81 (2.5H, m)*, 8.05-7.77 (9H, m), 7.71-7.64 (1H, m), 7.61-7.58 (2H, m), 7.58-7.51 (1H, m), 7.35-7.25 (3H, m), 6.66-6.62 (0.5H, bs)*, 6.66-6.59 (0.5H, bs)*, 4.87-4.76 (1H, m), 4.35 (1.5H, s)*, 4.25 (1.5H, s)*, 1.91 (3H, s), 1.37 (1.5H, d, J = 6.4 Hz)*, 1.31 (1.5H, d, J = 6.4 Hz)*. | Rt = 3.77 min, m/z = 572.2 [M]+ |
| 39 | 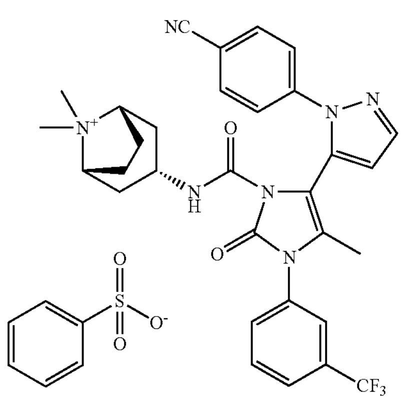 [SMILES: O=S(=O)([O-])c1ccccc1 ; Cc1c(-c2ccnn2-c2ccc(C#N)cc2)n(C(=O)N[C@@H]2C[C@H]3CC[C@@H](C2)[N+]3(C)C)c(=O)n1-c1cccc(C(F)(F)F)c1] | (1S,3S,5R)-8-Methyl-8-aza-bicyclo[3.2.1]oct-3-ylamine | Ex 29 | $^1$H NMR (400 MHz, CDCl$_3$): δ 8.71 (1H, d, J = 7.5 Hz), 7.89-7.83 (2H, m), 7.82 (1H, d, J = 1.8 Hz), 7.77-7.71 (3H, m), 7.70-7.59 (4H, m), 7.57 (1H, dm, J = 7.8 Hz), 7.35-7.29 (3H, m), 6.56 (1H, d, J = 1.8 Hz), 4.18 (1H, bs), 4.03 (1H, bs), 3.99-3.85 (1H, m), 3.46 (3H, s), 3.23 (3H, s), 2.40-2.29 (2H, m), 2.29-2.18 (2H, m), 1.99-1.88 (2H, m), 1.83 (3H, s), 1.83-1.74 (2H, | Rt = 3.81 min, m/z = 590.3 [M]+ |

-continued

| Ex. | Structure | Amine | Quat. Method | 1H NMR | LC-MS Method 3 |
|---|---|---|---|---|---|
| 40 | 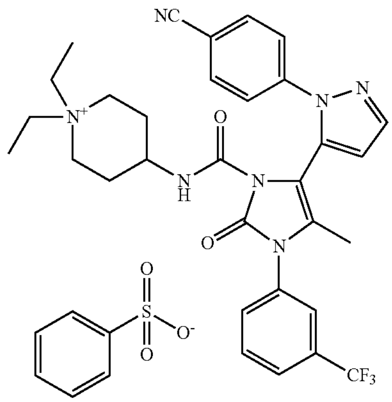 [SMILES: CC[N+]1(CC)CCC(NC(=O)n2c(-c3ccnn3-c3ccc(C#N)cc3)c(C)n(-c3cccc(C(F)(F)F)c3)c2=O)CC1 ; O=S(=O)([O-])c1ccccc1] | 1-Ethyl-piperidin-4-ylamine | Ex 31 | ¹H NMR (400 MHz, CDCl₃): δ 8.72 (1H, d, J = 6.7 Hz), 7.91-7.83 (2H, m), 7.80 (1H, d, J = 1.8 Hz), 7.79-7.74 (2H, m), 7.74-7.69 (1H, m), 7.69-7.58 (5H, m), 7.33-7.27 (3H, m), 6.59 (1H, d, J = 1.8 Hz), 3.92-3.83 (1H, m), 3.63-3.52 (2H, m), 3.53-3.34 (6H, m), 2.02-1.88 (3H, m), 1.86 (3H, s), 1.83-1.77 (1H, m), 1.27-1.19 (6H, m). | Rt = 3.80 min, m/z = 592.3 [M]+ |
| 41 | 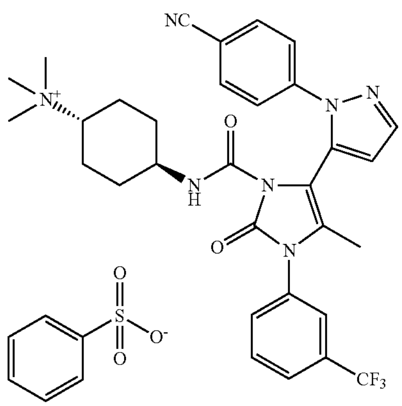 [SMILES: Cc1c(-c2ccnn2-c2ccc(C#N)cc2)n(C(=O)N[C@H]2CC[C@H]([N+](C)(C)C)CC2)c(=O)n1-c1cccc(C(F)(F)F)c1 ; O=S(=O)([O-])c1ccccc1] | See Ex 9 | Ex 29 | ¹H NMR (400 MHz, CDCl₃): δ 8.37 (1H, d, J = 7.3 Hz), 7.88-7.82 (2H, m), 7.81 (1H, d, J = 1.7 Hz), 7.78-7.66 (4H, m), 7.63-7.57 (3H, m), 7.57-7.52 (1H, m), 7.36-7.28 (3H, m), 6.55 (1H, d, J = 1.7 Hz), 3.68-3.52 (1H, m), 3.45-3.30 (1H, m), 3.19 (9H, s), 2.26-2.11 (2H, m), 2.08-1.98 (1H, m), 1.87 (3H, s), 1.86-1.82 (1H, m), 1.49-1.17 (4H, m). | Rt = 3.82 min, m/z = 592.4 [M]+ |
| 42 | 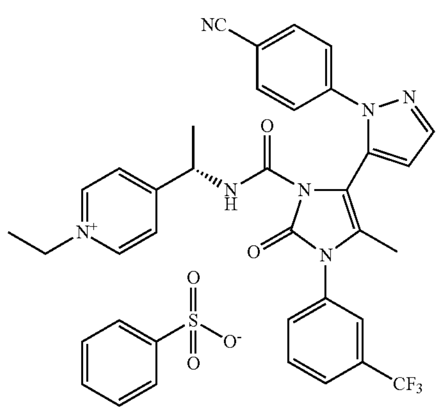 [SMILES: CC[n+]1ccc([C@H](C)NC(=O)n2c(-c3ccnn3-c3ccc(C#N)cc3)c(C)n(-c3cccc(C(F)(F)F)c3)c2=O)cc1 ; O=S(=O)([O-])c1ccccc1] | See Ex 5 | Ex 31 | ¹H NMR (400 MHz, CDCl₃): δ 9.27 (0.4H, d, J = 6.7 Hz)*, 9.25-9.19 (0.6H, m)*, 9.08-9.00 (2H, m), 7.92-7.82 (3H, m), 7.81-7.52 (10H, m), 7.34-7.29 (3H, m), 6.69 (0.4H, d, J = 1.7 Hz)*, 6.66 (0.2H, d, J = 1.7 Hz)*, 6.56 (0.4H, d, J = 1.7 Hz)*, 4.99-4.60 (3H, m), 1.87-1.84 (3H, m)*, 1.61 (1.3H, t, J = 7.3 Hz)*; 1.55-1.48 (1.7H, m)*, 1.48-1.40 (3H, m). | Rt = 3.86 min, m/z = 586.3 [M]+ |

-continued

| Ex. | Structure | Amine | Quat. Method | 1H NMR | LC-MS Method 3 |
|---|---|---|---|---|---|
| 43 | 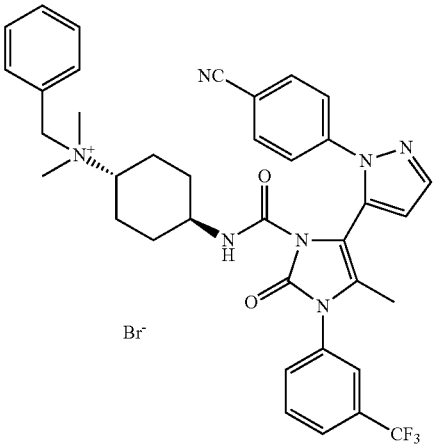 [SMILES: Cc1c(-c2ccnn2-c2ccc(C#N)cc2)n(C(=O)N[C@H]2CC[C@H]([N+](C)(C)Cc3ccccc3)CC2)c(=O)n1-c1cccc(C(F)(F)F)c1 ; [Br-]] | See Ex 9 | Ex 30 | $^1$H NMR (400 MHz, CDCl$_3$): δ 8.45 (1H, d, J = 7.3 Hz), 7.81 (1H, d, J = 1.77 Hz), 7.78-7.67 (4H, m), 7.64-7.53 (6H, m), 7.50-7.40 (3H, m), 6.57 (1H, d, J = 1.77 Hz), 5.00-4.89 (2H, m), 3.85 (1H, tm, J = 12 Hz), 3.54-3.44 (1H, m), 3.16 (3H, s), 3.14 (3H, s), 2.46-2.28 (2H, m), 2.21-2.11 (1H, m), 2.04-1.93 (1H, m), 1.88 (3H, s), 1.74-1.62 (2H, m), 1.45-1.19 (2H, m). | Rt = 4.17 min, m/z = 668.4 [M]+ |
| 44 | 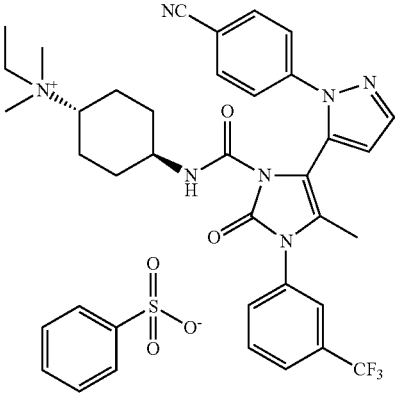 [SMILES: CC[N+](C)(C)[C@H]1CC[C@H](NC(=O)n2c(-c3ccnn3-c3ccc(C#N)cc3)c(C)n(-c3cccc(C(F)(F)F)c3)c2=O)CC1 ; O=S(=O)([O-])c1ccccc1] | See Ex 9 | Ex 31 | $^1$H NMR (400 MHz, CDCl$_3$): δ 8.40 (1H, d, J = 7.3 Hz), 7.88-7.84 (2H, m), 7.81 (1H, d, J = 1.8 Hz), 7.78-7.67 (4H, m), 7.63-7.57 (3H, m), 7.55 (1H, dm, J = 7.6 Hz), 7.36-7.28 (3H, m), 6.56 (1H, d, J = 1.8 Hz), 3.57-3.32 (4H, m), 3.12 (3H, s), 3.10 (3H, s), 2.24-2.01 (3H, m), 1.96-1.84 (1H, m), 1.88 (3H, s), 1.58-1.19 (4H, m), 1.33 (3H, t, J = 6.8 Hz). | Rt = 3.86 min, m/z = 606.4 [M]+ |
| 45 | 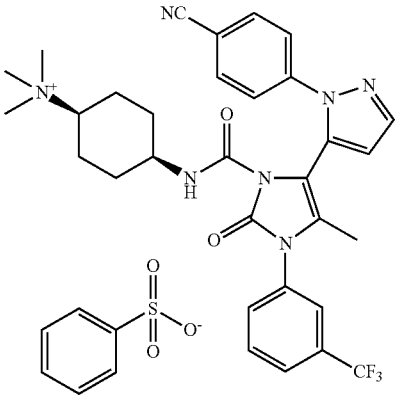 [SMILES: Cc1c(-c2ccnn2-c2ccc(C#N)cc2)n(C(=O)N[C@H]2CC[C@@H]([N+](C)(C)C)CC2)c(=O)n1-c1cccc(C(F)(F)F)c1 ; O=S(=O)([O-])c1ccccc1] | N,N-Dimethyl-cis-cyclo-hexane-1,4-diamine | Ex 29 | $^1$H NMR (400 MHz, CDCl$_3$): δ 8.61 (1H, d, J = 6.5 Hz), 7.86-7.82 (2H, m), 7.81 (1H, d, J = 1.8 Hz), 7.78-7.73 (3H, m), 7.68 (1H, tm, J = 7.8 Hz), 7.64-7.55 (4H, m), 7.33-7.28 (3H, m), 6.56 (1H, d, J = 1.8 Hz), 3.82 (1H, tm, J = 11.6 Hz), 3.76-3.69 (1H, m), 3.22-3.20 (9H, s), 2.13-1.98 (2H, m), 1.94 (3H, s), 1.93-1.84 (1H, m), 1.69-1.44 (2H, m), 1.52-1.39 (1H, m), 1.36-1.19 (2H, m). | Rt = 3.70 min, m/z = 592.4 [M]+ |

-continued

| Ex. | Structure | Amine | Quat. Method | 1H NMR | LC-MS Method 3 |
|---|---|---|---|---|---|
| 46 | 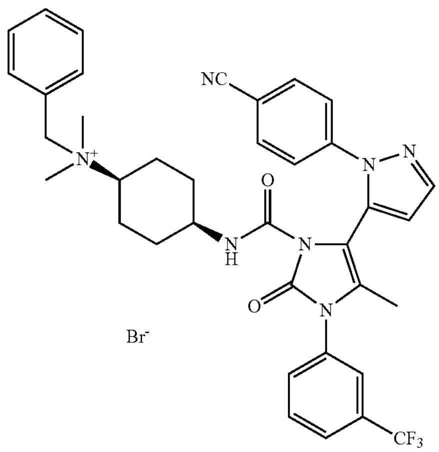 [SMILES: Cc1c(-c2ccnn2-c2ccc(C#N)cc2)n(C(=O)N[C@H]2CC[C@@H]([N+](C)(C)Cc3ccccc3)CC2)c(=O)n1-c1cccc(C(F)(F)F)c1 ; [Br-]] | N,N-Dimethyl-cis-cyclo-hexane-1,4-diamine | Ex 30 | ¹H NMR (400 MHz, CDCl₃): δ 8.66 (1H, d, J = 6.2 Hz), 7.83 (1H, d, J = 1.77 Hz), 7.81-7.75 (3H, m), 7.72 (1H, tm, J = 7.5 Hz), 7.67-7.58 (6H, m), 7.49-7.42 (3H, m), 6.59 (1H, d, J = 1.77 Hz), 4.86 (2H, s), 4.34-4.22 (1H, m), 3.83-3.77 (1H, m), 3.13 (3H, s), 3.10 (3H, s), 2.35-2.24 (1H, m), 2.21-2.11 (1H, m), 2.04-1.92 (1H, m), 1.98 (3H, s), 1.88-1.77 (1H, m), 1.76-1.56 (3H, m), 1.51-1.39 (1H, m). | Rt = 4.10 min, m/z = 668.5 [M]+ |
| 47 | 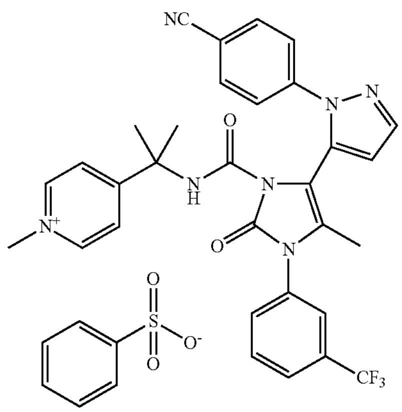 [SMILES: Cc1c(-c2ccnn2-c2ccc(C#N)cc2)n(C(=O)NC(C)(C)c2cc[n+](C)cc2)c(=O)n1-c1cccc(C(F)(F)F)c1 ; O=S(=O)([O-])c1ccccc1] | 1-Methyl-1-pyridin-4-yl-ethylamine | Ex 29 | ¹H NMR (400 MHz, CDCl₃): δ 9.35 (1H, s), 8.88 (2H, d, J = 6.7 Hz), 7.89-7.82 (2H, m), 7.82-7.70 (5H, m), 7.70-7.64 (2H, m), 7.63 (1H, d, J = 1.75 Hz), 7.61-7.56 (1H, m), 7.55-7.49 (2H, m), 7.33-7.29 (3H, m), 6.56 (1H, d, J = 1.75 Hz), 4.28 (3H, s), 1.91 (3H, s), 1.46 (3H, s), 1.42 (3H, s). | Rt = 3.88 min, m/z = 586.4 [M]+ |
| 48 | 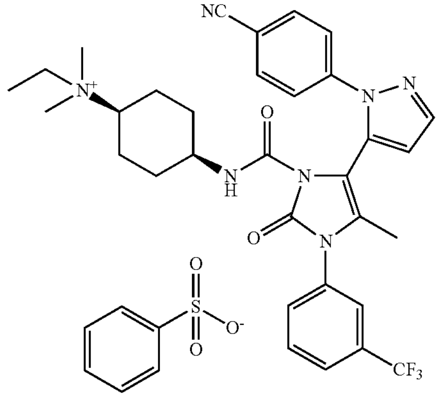 [SMILES: CC[N+](C)(C)[C@H]1CC[C@@H](NC(=O)n2c(-c3ccnn3-c3ccc(C#N)cc3)c(C)n(-c3cccc(C(F)(F)F)c3)c2=O)CC1 ; O=S(=O)([O-])c1ccccc1] | N,N-Dimethyl-cis-cyclo-hexane-1,4-diamine | Ex 31 | ¹H NMR (400 MHz, CDCl₃): δ 8.61 (1H, d, J = 6.3 Hz), 7.88-7.83 (2H, m), 7.82 (1H, d, J = 1.76 Hz), 7.79-7.73 (3H, m), 7.68 (1H, tm, J = 7.8 Hz), 7.65-7.57 (4H, m), 7.33-7.28 (3H, m), 6.57 (1H, d, J = 1.76 Hz), 3.79-3.64 (2H, m), 3.48 (2H, q, J = 7 Hz), 3.13 (3H, s), 3.10 (3H, s), 2.12-1.87 (4H, m), 1.95 (3H, s), 1.76-1.50 (3H, m), 1.44-1.30 (1H, m), 1.36 (3H, t, J = 7 Hz). | Rt = 3.76 min, m/z = 606.4 [M]+ |

-continued

| Ex. | Structure | Amine | Quat. Method | 1H NMR | LC-MS Method 3 |
|---|---|---|---|---|---|
| 49 | 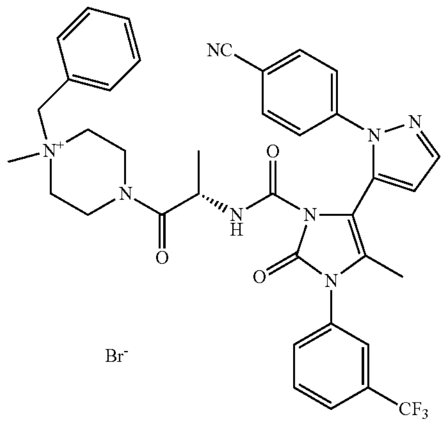 [SMILES: Cc1c(-c2ccnn2-c2ccc(C#N)cc2)n(C(=O)N[C@@H](C)C(=O)N2CC[N+](C)(Cc3ccccc3)CC2)c(=O)n1-c1cccc(C(F)(F)F)c1 ; [Br-]] | See Ex 11 | Ex 30 | ¹H NMR (400 MHz, d6-DMSO): δ 9.12-8.90 (1H, m)*, 8.09-7.98 (1H, m)*, 7.97-7.81 (6H, m), 7.73-7.63 (2H, m), 7.60-7.46 (5H, m), 6.67-6.64 (1H, m), 4.72-4.46 (3H, m), 4.23-4.05 (1H, m), 4.03-3.89 (1H, m), 3.78-3.62 (1H, m), 3.61-3.29 (5H, m), 3.06-2.95 (3H, m), 1.98-1.82 (3H, m), 1.22-1.11 (1H, m)*, 0.95-0.80 (2H, m)*. | Rt = 4.03 min, m/z = 697.5 [M]+ |
| 50 | 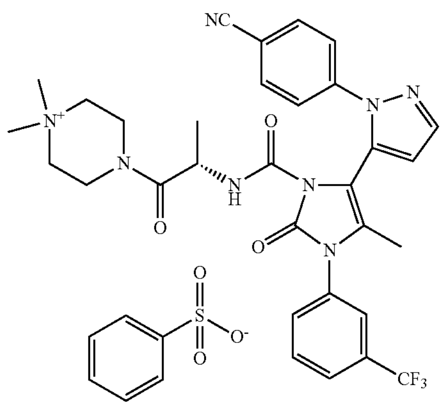 [SMILES: Cc1c(-c2ccnn2-c2ccc(C#N)cc2)n(C(=O)N[C@@H](C)C(=O)N2CC[N+](C)(C)CC2)c(=O)n1-c1cccc(C(F)(F)F)c1 ; O=S(=O)([O-])c1ccccc1] | See Ex 11 | Ex 29 | ¹H NMR (400 MHz, d6-DMSO): δ 9.05 (0.6H, d, J = 6.5 Hz)*, 8.96 (0.4H, d, J = 6.9 Hz)*, 8.07-8.00 (1H, m)*, 7.97-7.79 (6H, m), 7.72-7.65 (2H, m), 7.62-7.56 (2H, m), 7.35-7.26 (3H, m), 6.66-6.64 (1H, m)*, 4.59-4.48 (1H, m), 3.88-3.64 (4H, m), 3.45-3.27 (4H, m), 3.20-3.06 (6H, m)*, 1.94 (1.9H, s)*, 1.86 (1.1H, s)*, 1.14 (1H, d, J = 7.2 Hz)*, 0.86 (2H, d, J = 6.7 Hz)*. | Rt = 3.72 min, m/z = 621.4 [M]+ |
| 51 | 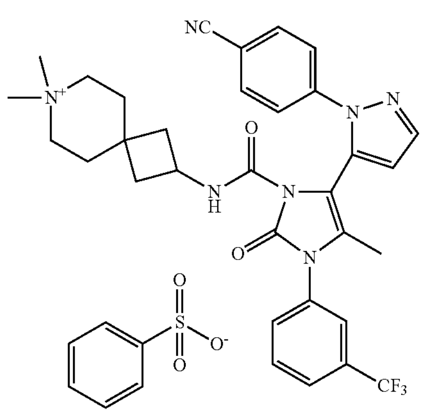 [SMILES: Cc1c(-c2ccnn2-c2ccc(C#N)cc2)n(C(=O)NC2CC3(CC[N+](C)(C)CC3)C2)c(=O)n1-c1cccc(C(F)(F)F)c1 ; O=S(=O)([O-])c1ccccc1] | 7-Methyl-7-aza-spiro[3.5]-non-2-ylamine | Ex 29 | ¹H NMR (400 MHz, d6-DMSO): δ 8.42 (1H, d, J = 7.4 Hz), 8.00 (1H, s), 7.95-7.79 (6H, m), 7.69-7.63 (2H, m), 7.61-7.56 (2H, m), 7.33-7.28 (3H, m), 6.64 (1H, d, J = 1.8 Hz), 3.88 (1H, tdt, J = 7.8, 7.8, 7.9 Hz), 3.27-3.12 (4H, m), 3.02 (6H, s), 2.18-1.97 (2H, m), 1.90 (3H, s), 1.85-1.64 (5H, m), 1.50-1.42 (1H, m). | Rt = 3.85 min, m/z = 604.4 [M]+ |

| Ex. | Structure | Amine | Quat. Method | 1H NMR | LC-MS Method 3 |
|---|---|---|---|---|---|
| 52 | 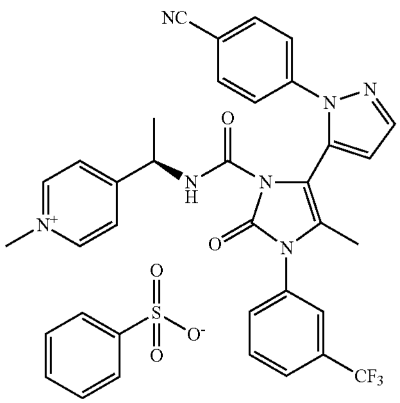 [SMILES: Cc1c(-c2ccnn2-c2ccc(C#N)cc2)n(C(=O)N[C@H](C)c2cc[n+](C)cc2)c(=O)n1-c1cccc(C(F)(F)F)c1 ; O=S(=O)([O-])c1ccccc1] | See Ex 6 | Ex 29 | ¹H NMR (400 MHz, CDCl₃): δ 9.26 (0.4H, d, J = 6.9 Hz)*, 9.22 (0.6H, d, 3=6.0 Hz)*, 8.94 (1H, d, J = 6.4 Hz)*, 8.91 (1H, d, J = 6.2 Hz)*, 7.89-7.78 (3H, m), 7.78-7.68 (4H, m), 7.68-7.61 (3H, m), 7.61-7.51 (3H, m), 7.34-7.28 (3H, m), 6.68 (0.5H, d, J = 1.7 Hz)*, 6.61 (0.1H, d, J = 1.7 Hz)*, 6.55 (0.4H, d, J = 1.7 Hz)*, 4.91 (0.4H, td, J = 14.0, 7.0 Hz)*, 4.82 (0.6H, td, J = 13.8, 6.9 Hz)*, 4.45 (1.2H, s)*, 4.35 (0.3H, s)*, 4.33 (1.5H, s)*, 1.87-1.83 (3H, m), 1.44-1.39 (3H, m). | Rt = 3.76 min, m/z = 572.3 [M]+ |
| 53 | 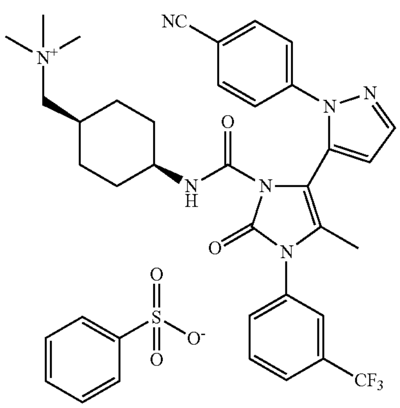 [SMILES: Cc1c(-c2ccnn2-c2ccc(C#N)cc2)n(C(=O)N[C@H]2CC[C@@H](C[N+](C)(C)C)CC2)c(=O)n1-c1cccc(C(F)(F)F)c1 ; O=S(=O)([O-])c1ccccc1] | 4-Dimethyl-aminomethyl-cis-cyclohexyl-amine | Ex 29 | ¹H NMR (400 MHz, CDCl₃): δ 8.52 (1H, d, 3=6.5 Hz), 7.89-7.82 (2H, m), 7.81 (1H, d, J = 1.8 Hz), 7.78-7.72 (3H, m), 7.68 (1H, t, J = 8.0 Hz), 7.64 (1H, m), 7.62-7.56 (3H, m), 7.34-7.27 (3H, m), 6.56 (1H, d, J = 1.8 Hz), 3.69-3.62 (1H, m), 3.39 (1H, dd, J = 13.4, 3.6 Hz), 3.30 (9H, s), 3.21 (1H, dd, J = 13.4, 4.8 Hz), 1.94 (3H, s), 1.94-1.84 (1H, m), 1.70-1.52 (4H, m), 1.45-1.20 (3H, m), 1.13-1.04 (1H, m). | Rt = 3.83 min, mix = 606.4 [M]+ |
| 54 | 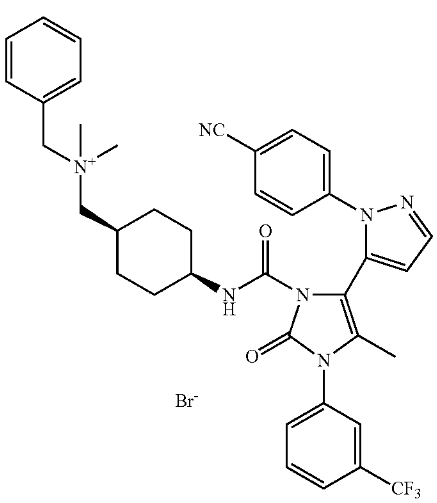 [SMILES: Cc1c(-c2ccnn2-c2ccc(C#N)cc2)n(C(=O)N[C@H]2CC[C@@H](C[N+](C)(C)Cc3ccccc3)CC2)c(=O)n1-c1cccc(C(F)(F)F)c1 ; [Br-]] | 4-Dimethyl-aminomethyl-cis-cyclohexyl-amine | Ex 30 | ¹H NMR (400 MHz, CDCl₃): δ 8.53 (1H, d, J = 6.3 Hz), 7.81 (1H, d, J = 1.8 Hz), 7.79-7.72 (3H, m), 7.71 (1H, t, J = 7.8 Hz), 7.67-7.58 (6H, m), 7.51-7.39 (3H, m), 6.57 (1H, d, J = 1.8 Hz), 5.06-4.95 (2H, m), 3.77-3.68 (1H, m), 3.68-3.60 (1H, m), 3.34-3.25 (1H, m), 3.28 (3H, s), 3.27 (3H, s), 2.29-2.18 (1H, m), 1.96 (3H, s), 1.82-1.64 (4H, m), 1.62-1.52 (1H, m), 1.50-1.41 (1H, m), 1.41-1.27 (1H, m), 1.18-1.05 (1H, m). | Rt = 4.21 min, m/z = 682.4 [M]+ |

-continued

| Ex. | Structure | Amine | Quat. Method | 1H NMR | LC-MS Method 3 |
|---|---|---|---|---|---|
| 55 | 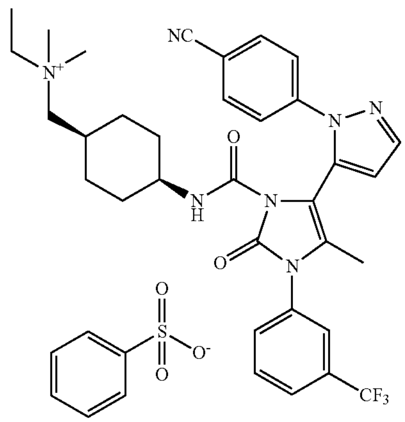 [SMILES: CC[N+](C)(C)C[C@H]1CC[C@@H](NC(=O)n2c(-c3ccnn3-c3ccc(C#N)cc3)c(C)n(-c3cccc(C(F)(F)F)c3)c2=O)CC1 ; O=S(=O)([O-])c1ccccc1] | 4-Dimethyl-aminomethyl-cis-cyclohexyl-amine | Ex 31 | $^1$H NMR (400 MHz, CDCl$_3$): δ 8.53 (1H, d, J = 6.4 Hz), 7.89-7.83 (2H, m), 7.81 (1H, d, J = 1.8 Hz), 7.78-7.71 (3H, m), 7.69 (1H, tm, J = 7.8 Hz), 7.64 (1H, m), 7.62-7.56 (3H, m), 7.34-7.28 (3H, m), 6.56 (1H, d, J = 1.8 Hz), 3.72-3.64 (1H, m), 3.63-3.51 (2H, m), 3.32 (1H, dd, J = 13.6, 3.7 Hz), 3.23 (3H, s), 3.21 (3H, s), 3.16 (1H, dd, J = 13.6, 4.9 Hz), 2.01-1.89 (1H, m), 1.96 (3H, s), 1.74-1.54 (3H, m), 1.52-1.20 (4H, m), 1.33 (3H, t, J = 7.2 Hz), 1.13-1.04 (1H, m). | Rt = 3.88 min, m/z = 620.4 [M]+ |
| 56 | 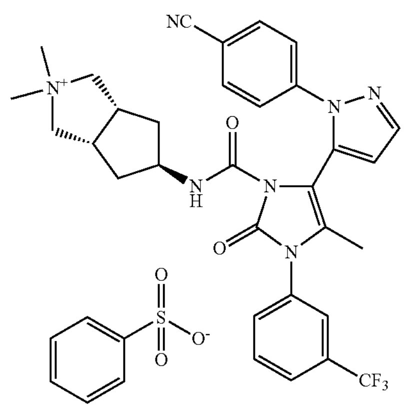 [SMILES: Cc1c(-c2ccnn2-c2ccc(C#N)cc2)n(C(=O)N[C@H]2C[C@@H]3C[N+](C)(C)C[C@@H]3C2)c(=O)n1-c1cccc(C(F)(F)F)c1 ; O=S(=O)([O-])c1ccccc1] | (3aR,5S,6aS)-2-Methyl-octahydro-cyclopenta-[c]pyrrol-5-ylamine | Ex 29 | $^1$H NMR (400 MHz, CDCl$_3$): δ 8.55 (1H, d, J = 6.5 Hz), 7.87-7.82 (2H, m), 7.81 (1H, d, J = 1.8 Hz), 7.77 (1H, dm, J = 7.8 Hz), 7.74-7.66 (3H, m), 7.61 (1H, m), 7.60-7.56 (2H, m), 7.53 (1H, dm, J = 8.4 Hz), 7.36-7.29 (3H, m), 6.56 (1H, d, J = 1.8 Hz), 4.21-4.13 (1H, m), 4.08-3.99 (1H, m), 3.98-3.90 (1H, m), 3.42 (3H, s), 3.20 (3H, s), 3.16-2.95 (4H, m), 1.88 (3H, s), 1.88-1.83 (1H, m), 1.83-1.75 (1H, m), 1.70-1.60 (1H, m), 1.58-1.46 (1H, m). | Rt = 3.76 min, m/z = 590.4 [M]+ |
| 57 | 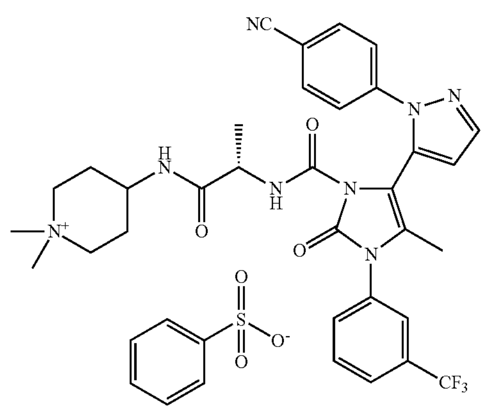 [SMILES: Cc1c(-c2ccnn2-c2ccc(C#N)cc2)n(C(=O)N[C@@H](C)C(=O)NC2CC[N+](C)(C)CC2)c(=O)n1-c1cccc(C(F)(F)F)c1 ; O=S(=O)([O-])c1ccccc1] | See Ex 13 | Ex 29 | $^1$H NMR (400 MHz, d6-DMSO): δ 8.82 (1H, d, J = 6.9 Hz), 8.12-7.99 (2H, m), 7.96-7.79 (6H, m), 7.69-7.63 (2H, m), 7.61-7.58 (2H, m), 7.32-7.29 (3H, m), 6.65 (1H, d, J = 1.7 Hz), 4.02-3.89 (1H, m), 3.80-3.67 (1H, m), 3.37-3.29 (4H, m), 3.14-2.98 (6H, 4 x s)*, 1.99-1.83 (5H, s)*, 1.81-1.66 (2H, m), 1.16 (1H, d, J = 6.7 Hz)*, 0.94-0.84 (2H, m)*. | Rt = 3.64 min, m/z = 635.3 [M]+ |

-continued

| Ex. | Structure | Amine | Quat. Method | 1H NMR | LC-MS Method 3 |
|---|---|---|---|---|---|
| 58 | 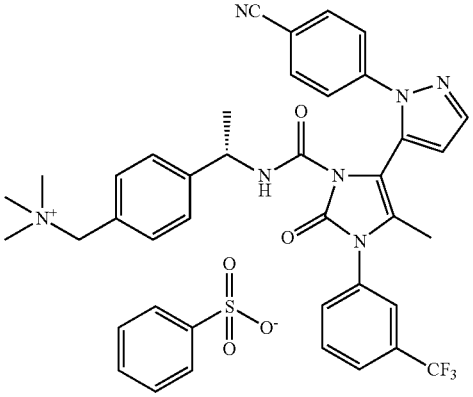 [SMILES: Cc1c(-c2ccnn2-c2ccc(C#N)cc2)n(C(=O)N[C@@H](C)c2ccc(C[N+](C)(C)C)cc2)c(=O)n1-c1cccc(C(F)(F)F)c1 ; O=S(=O)([O-])c1ccccc1] | See Ex 14 | Ex 29 | ¹H NMR (400 MHz, d6-DMSO): δ 8.76 (0.5H, d, J = 7.2 Hz)*, 8.69 (0.5H, d, J = 7.6 Hz)*, 8.03 (1H, m), 7.99-7.78 (6H, m), 7.68 (1H, d, J = 8.4 Hz), 7.64-7.55 (3H, m), 7.47-7.29 (6H, m), 7.19 (1H, d, J = 7.7 Hz), 6.69-6.60 (1H, m), 4.74-4.58 (1H, m), 4.57-4.40 (2H, m), 3.02 (4.5H, s)*, 2.97 (4.5H, s)*, 1.95-1.89 (3H, m), 1.35 (1.5H, d, J = 7.0 Hz)*, 1.17 (1.5H, d, J = 6.9 Hz)*. | Rt = 3.95 min, m/z = 628.4 [M]+ |
| 59 | 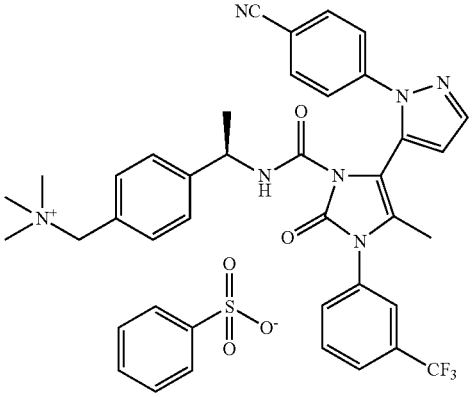 [SMILES: Cc1c(-c2ccnn2-c2ccc(C#N)cc2)n(C(=O)N[C@H](C)c2ccc(C[N+](C)(C)C)cc2)c(=O)n1-c1cccc(C(F)(F)F)c1 ; O=S(=O)([O-])c1ccccc1] | (R)-1-(4-Dimethyl-aminomethyl-phenyl)-ethyl amine | Ex 29 | ¹H NMR (400 MHz, d6-DMSO): δ 8.75 (0.5H, d, J = 7.2 Hz)*, 8.69 (0.5H, d, J = 7.7 Hz)*, 8.03 (1H, m), 7.99-7.78 (6H, m), 7.68 (1H, d, J = 8.4 Hz), 7.62-7.58 (3H, m), 7.48-7.41 (2H, m), 7.41-7.35 (1H, m), 7.34-7.26 (3H, m), 7.22-7.15 (1H, m), 6.68-6.60 (1H, m), 4.73-4.58 (1H, m), 4.56-4.41 (2H, m), 3.05-2.95 (9H, m)*, 1.96-1.89 (3H, m), 1.35 (1.5H, d, J = 6.7 Hz)*, 1.17 (1.5H, d, J = 6.6 Hz)*. | Rt = 3.95 min, m/z = 628.4 [M]+ |
| 60 | 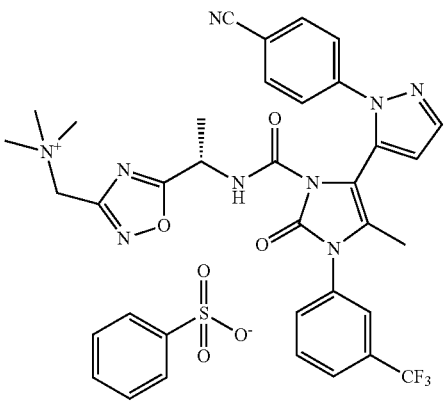 [SMILES: Cc1c(-c2ccnn2-c2ccc(C#N)cc2)n(C(=O)N[C@@H](C)c2nc(C[N+](C)(C)C)no2)c(=O)n1-c1cccc(C(F)(F)F)c1 ; O=S(=O)([O-])c1ccccc1] | Intermed. B | Ex 29 | ¹H NMR (400 MHz, d6-DMSO): δ 9.08 (1H, d, J = 7.1 Hz), 8.05 (1H, m), 7.96-7.83 (6H, m), 7.69-7.62 (2H, m), 7.61-7.57 (2H, m), 7.35-7.26 (3H, m), 6.66-6.62 (1H, m), 5.04-4.95 (1H, m), 4.81-4.75 (2H, m)*, 3.19-3.10 (9H, m)*, 1.93 (1.5H, s)*, 1.92 (1.5H, s)*, 1.39-1.33 (3H, m). | Rt = 3.84 min, m/z = 620.4 [M]+ |

-continued

| Ex. | Structure | Amine | Quat. Method | 1H NMR | LC-MS Method 3 |
|---|---|---|---|---|---|
| 61 | 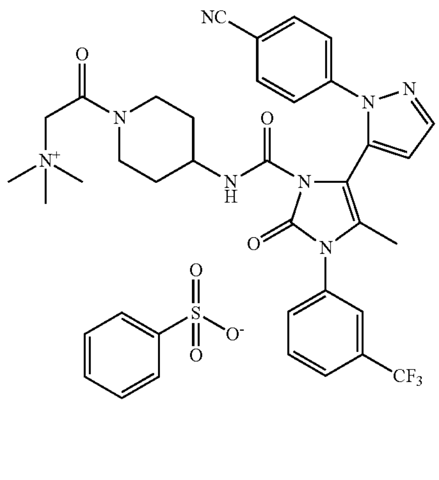 [SMILES: Cc1c(-c2ccnn2-c2ccc(C#N)cc2)n(C(=O)NC2CCN(C(=O)C[N+](C)(C)C)CC2)c(=O)n1-c1cccc(C(F)(F)F)c1 ; O=S(=O)([O-])c1ccccc1] | See Ex 17 | Ex 29 | ¹H NMR (400 MHz, d6-DMSO): δ 8.38-8.33 (1H, m), 8.01 (1H, s), 7.94-7.80 (6H, m), 7.70-7.65 (2H, m), 7.61-7.57 (2H, m), 7.33-7.27 (3H, m), 6.65 (1H, d, J = 1.8 Hz), 4.41 (2H, s), 4.05-3.91 (1H, m), 3.59-3.46 (2H, m), 3.21 (9H, s), 3.13-3.03 (1H, m), 2.90-2.82 (1H, m), 1.91 (3H, s), 1.77-1.67 (1H, m), 1.55-1.20 (3H, m). | Rt = 3.77 min, m/z = 635.4 [M]+ |
| 62 | 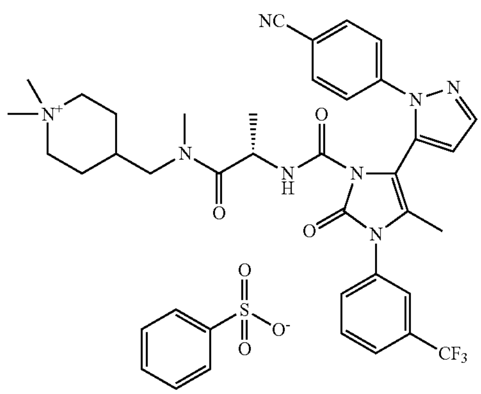 [SMILES: Cc1c(-c2ccnn2-c2ccc(C#N)cc2)n(C(=O)N[C@@H](C)C(=O)N(C)CC2CC[N+](C)(C)CC2)c(=O)n1-c1cccc(C(F)(F)F)c1 ; O=S(=O)([O-])c1ccccc1] | See Ex 18 | Ex 29 | ¹H NMR (400 MHz, d6-DMSO): δ 8.89 (1H, br s), 7.92 (1H, s), 7.90-7.78 (6H, m), 7.67-7.59 (4H, m), 7.30-7.21 (3H, m), 6.61 (1H, d J = 1.7 Hz), 4.47 (1H, br S), 3.44-3.14 (6H, m), 3.10-3.00 (6H 2xs signals partially obscured by water), 2.95-2.75 (3H, br m), 2.00-1.80 (4H, br m), 1.75-1.45 (4H, br m), 1.25-0.85 (3H, br m). | Rt = 3.74 min, m/z = 663.4 [M]+ |
| 63 | 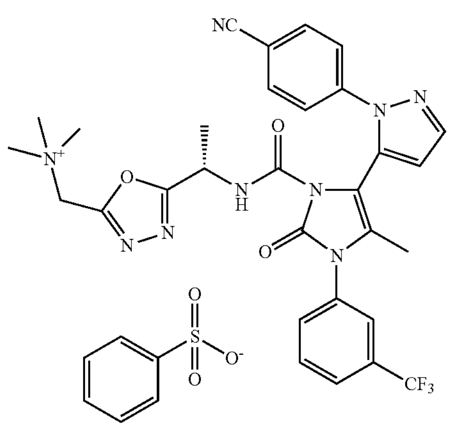 [SMILES: Cc1c(-c2ccnn2-c2ccc(C#N)cc2)n(C(=O)N[C@@H](C)c2nnc(C[N+](C)(C)C)o2)c(=O)n1-c1cccc(C(F)(F)F)c1 ; O=S(=O)([O-])c1ccccc1] | Intermed. C | Ex 29 | ¹H NMR (400 MHz, d6-DMSO): δ 9.10 (0.45H, d J = 7.0 Hz), 9.00 (0.55H, d J = 7.4 Hz), 8.02 (1H, s), 8.00-7.75 (6H, m), 7.72-7.64 (2H, m), 7.61-7.57 (2H, m), 7.34-7.26 (3H, m), 6.67-6.62 (1H, m), 5.04-4.90 (3H, m), 3.19-3.15 (9H, m), 1.93-1.88 (3H, m), 1.39-1.28 (3H, m). | Rt = 3.54 min, mix = 620.4 [M]+ |

-continued

| Ex. | Structure | Amine | Quat. Method | 1H NMR | LC-MS Method 3 |
|---|---|---|---|---|---|
| 64 | 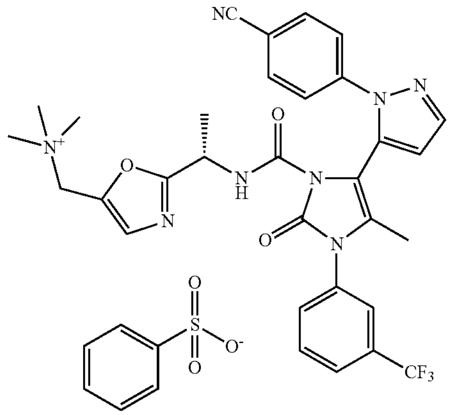 [SMILES: Cc1c(-c2ccnn2-c2ccc(C#N)cc2)n(C(=O)N[C@@H](C)c2ncc(C[N+](C)(C)C)o2)c(=O)n1-c1cccc(C(F)(F)F)c1 ; O=S(=O)([O-])c1ccccc1] | See Ex 16 | Ex 29 | ¹H NMR (400 MHz, d6-DMSO): δ 9.07-8.97 (1H, m), 8.02 (1H, s), 7.96-7.80 (6H, m), 7.70-7.56 (4H, m), 7.39 (1H, s), 7.34-7.28 (3H, m), 6.65 (1H, s), 4.84-4.72 (1H, m), 4.68 and 4.65 (2H, 2xs)*, 3.01 (9H,br s), 1.92 and 1.89 (3H, 2xs)*, 1.35 and 1.20 (3H, 2xd J = 6.8 Hz)*. | Rt = 3.74 min, m/z = 619.4 [M]+ |
| 65 | 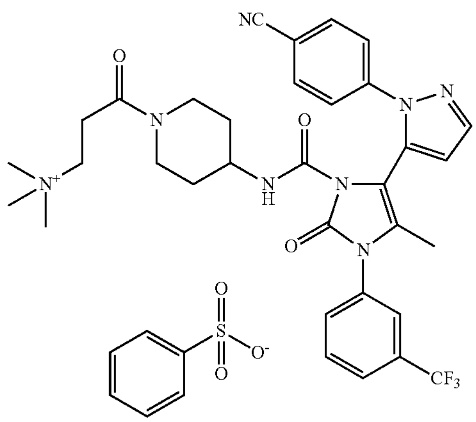 [SMILES: Cc1c(-c2ccnn2-c2ccc(C#N)cc2)n(C(=O)NC2CCN(C(=O)CC[N+](C)(C)C)CC2)c(=O)n1-c1cccc(C(F)(F)F)c1 ; O=S(=O)([O-])c1ccccc1] | See Ex 15 | Ex 29 | ¹H NMR (400 MHz, d6-DMSO): δ 8.40-8.31 (1H, m), 8.02 (1H, s), 7.95-7.88 (3H, m), 7.88-7.78 (3H, m), 7.71-7.63 (2H, m), 7.61-7.55 (2H, m), 7.35-7.25 (3H, m), 6.65 (1H, d J = 1.7 Hz), 4.00-3.88 (1H, m), 3.75-3.60 (1H, m), 3.56-3.45 (3H, m), 3.17-3.00 (10H, overlapping s and m), 2.90-2.75 (3H, m), 1.91 (3H, s), 1.74-1.64 (1H, m), 1.52-1.334 (2H, m), 1.28-1.14 (1.3H, m)*, 1.04-0.90 (0.7H, m)*. | Rt = 3.72 min, m/z = 649.5 [M]+ |
| 66 | 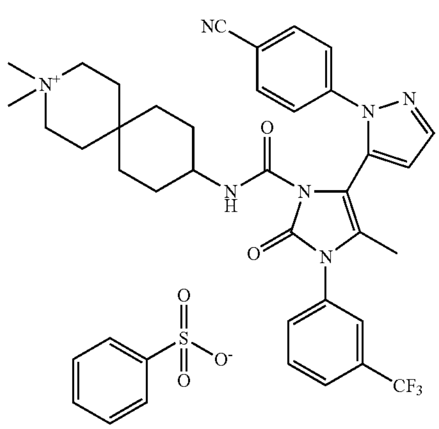 [SMILES: Cc1c(-c2ccnn2-c2ccc(C#N)cc2)n(C(=O)NC2CCC3(CC2)CC[N+](C)(C)CC3)c(=O)n1-c1cccc(C(F)(F)F)c1 ; O=S(=O)([O-])c1ccccc1] | 3-Methyl-3-aza-spiro-[5.5]undec-9-yl amine | Ex 29 | ¹H NMR (400 MHz, d6-DMSO): δ 8.40-8.31 (1H, m), 8.02 (1H, s), 7.95-7.88 (3H, m), 7.88-7.78 (3H, m), 7.71-7.63 (2H, m), 7.61-7.55 (2H, m), 7.35-7.25 (3H, m), 6.65 (1H, d J = 1.7 Hz), 4.00-3.88 (1H, m), 3.75-3.60 (1H, m), 3.56-3.45 (3H, m), 3.17-3.00 (10H, overlapping s and m), 2.90-2.75 (3H, m), 1.91 (3H, s), 1.74-1.64 (1H, m), 1.52-1.334 (2H, m), 1.28-1.14 (1.3H, m)*, 1.04-0.90 (0.7H, m)*. | Rt = 3.87 min, m/z = 632.4 [M]+ |

-continued

| Ex. | Structure | Amine | Quat. Method | 1H NMR | LC-MS Method 3 |
|---|---|---|---|---|---|
| 67 | 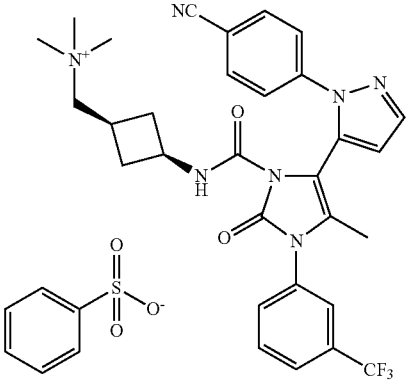 [SMILES: O=S(=O)([O-])c1ccccc1 ; Cc1c(-c2ccnn2-c2ccc(C#N)cc2)n(C(=O)N[C@H]2C[C@@H](C[N+](C)(C)C)C2)c(=O)n1-c1cccc(C(F)(F)F)c1] | Cis-3-dimethyl-aminomethyl-cyclobutyl-amine | Ex 29 | $^1$H NMR (400 MHz, d6-DMSO): δ 8.41 (1H, d J = 7.7 Hz), 8.00 (1H, s), 7.93-7.80 (6H, m), 7.66 (2H, d J = 8.8 Hz), 7.61-7.57 (2H, m), 7.34-7.26 (3H, m), 6.64 (1H, d J = 1.8 Hz), 3.86-3.74 (1H, m), 3.36-3.28 (signal partially obscured by water, assumed 2H), 2.98 (9H, s), 2.44-2.20 (3H, m), 1.90 (3H, s), 1.78-1.66 (1H, m), 1.63-1.51 (1H, m). | Rt = 3.71 min, m/z = 578.3 [M]+ |
| 68 | 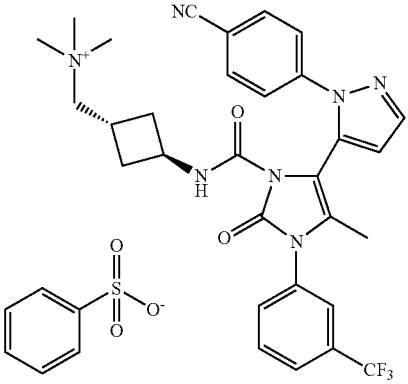 [SMILES: O=S(=O)([O-])c1ccccc1 ; Cc1c(-c2ccnn2-c2ccc(C#N)cc2)n(C(=O)N[C@H]2C[C@H](C[N+](C)(C)C)C2)c(=O)n1-c1cccc(C(F)(F)F)c1] | Trans-3-dimethyl-aminomethyl-cyclobutyl-amine | Ex 29 | $^1$H NMR (400 MHz, d6-DMSO): δ 8.54 (1H, d J = 6.5 Hz), 8.01 (1H, s), 7.94-7.80 (6H, m), 7.67 (2H, d J = 8.9 Hz), 7.61-7.57 (2H, m), 7.34-7.28 (3H, m), 6.64 (1H, d J = 1.8 Hz), 3.94-3.83 (1H, m), 3.40 (2H, d J = 6.8 Hz), 2.97 (9H, s), 2.81-2.70 (1H, m), 2.13-2.04 (2H, m), 2.03-1.94 (1H, m), 1.93-1.80 (4H, overlapping m and s). | Rt = 3.73 min, m/z = 578.3 [M]+ |
| 69 | 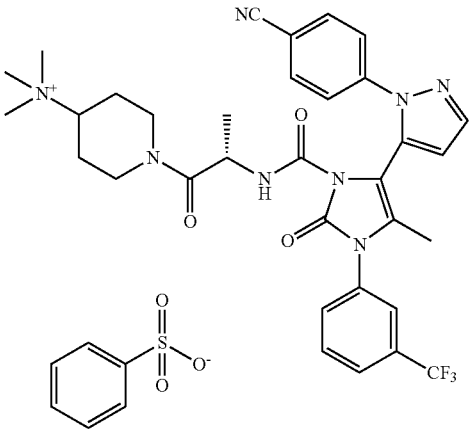 [SMILES: Cc1c(-c2ccnn2-c2ccc(C#N)cc2)n(C(=O)N[C@@H](C)C(=O)N2CCC([N+](C)(C)C)CC2)c(=O)n1-c1cccc(C(F)(F)F)c1 ; O=S(=O)([O-])c1ccccc1] | See Ex 19 | Ex 29 | $^1$H NMR (400 MHz, d6-DMSO): δ 9.0-8.96 (0.8H, m)*, 8.83 (0.2H, d J = 7.1 Hz)*, 8.06-8.00 (1H, m), 7.96-7.80 (6H, m), 7.71-7.63 (2H, m), 7.62-7.56 (2H, m), 7.35-7.26 (3H, m), 7.64 (1H, br s), 4.56-4.38 (2H, m), 4.02-3.86 (1H, m), 3.62-3.48 (1.4H, m)*, 3.06-2.92 (9H, m), 2.60-2.52 (peak partially obscured by solvent, 0.6H)*, 2.20-2.00 (2H, m), 1.96-1.84 (3H, m), 1.68-1.36 (2.4H, m)*, 1.24-1.10 (2H, m), 0.88-0.80 (1.6H, m)*. | Rt = 3.70 min, m/z = 649.4 [M]+ |

-continued

| Ex. | Structure | Amine | Quat. Method | 1H NMR | LC-MS Method 3 |
|---|---|---|---|---|---|
| 70 | (structure shown with Br⁻ counterion) | See Ex 19 | Ex 30 | ¹H NMR (400 MHz, d6-DMSO): δ 9.08-8.98 (0.8H, m)*, 8.85 (0.2H, d, J = 6.9 Hz)*, 8.50 (1H, s), 8.06-8.00 (1H, m), 7.98-7.76 (6H, m), 7.72-7.62 (2H, m), 7.60-7.46 (5H, m), 6.67-6.63 (1H, m), 4.60-4.40 (4H, m), 4.02-3.90 (1.4H, m)*, 3.68-2.95 (0.6H peaks partially obscured by water)*, 2.91-2.77 (6H, m), 2.65-2.45 (1H, m, partially obscured by solvent), 2.40-2.15 (2H, m), 1.98-1.84 (3H, m), 1.84-1.55 (2H, m), 1.18-1.10 (1.2H, m)*, 0.91-0.81 (1.8H, m)*. | Rt = 4.01 min, m/z = 725.4 [M]+ |
| 71 | (structure shown with benzenesulfonate counterion) | See Ex 20 | Ex 29 | ¹H NMR (400 MHz, d6-DMSO): δ 8.99 (0.6H, d J = 6.6 Hz)*, 8.88 (0.4H, d J = 7.1 Hz)*, 8.05-8.00 (1H, m), 7.95-7.80 (6H, m), 7.71-7.64 (2H, m), 7.61-7.56 (2H, m), 7.34-7.26 (3H, m), 6.66-6.62 (1H, m), 4.49-4.38 (1H, m), 3.86-3.50 (2H, m), 3.44-3.36 (2H, signal partially obscured by water), 3.10-3.02 (9H, 2xs)*, 3.00-2.94 (3H, 2xs)*,1.93 (1.8H, s)*, 1.86 (1.2H, s)*,1.18-1.10 (1.2H, m)*, 0.92-0.84 (1.8H, m)*. | Rt = 3.78 min, m/z = 623.4 [M]+ |
| 72 | (structure shown with Cl⁻ counterion) | See Ex 9 | Ex 30 (using 3-Chloromethyl-[1,2,4]-oxadiazole) | ¹H NMR (400 MHz, d6-DMSO): δ 9.89 (1H, s), 8.21 (1H, d J = 7.4 Hz), 8.01 (1H, s), 7.93-7.80 (6H, m), 7.67 (2H, d J = 8.9 Hz), 6.64 (1H, d J = 1.8 Hz), 4.89 (2H, s), 3.34-3.20 (2H, signals partially obscured by water), 3.07 (6H, s), 2.20-2.10 (2H, m), 1.92-1.80 (4H, m), 1.70-1.50 (3H, m), 1.28-1.00 (2H, m) | Rt = 3.84 min, m/z = 660.4 [M]+ |

| Ex. | Structure | Amine | Quat. Method | 1H NMR | LC-MS Method 3 |
|---|---|---|---|---|---|
| 73 | 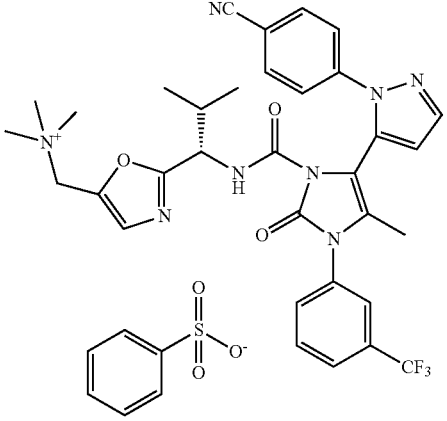 [SMILES: Cc1c(-c2ccnn2-c2ccc(C#N)cc2)n(C(=O)N[C@H](c2ncc(C[N+](C)(C)C)o2)C(C)C)c(=O)n1-c1cccc(C(F)(F)F)c1 ; O=S(=O)([O-])c1ccccc1] | See Ex 21 | Ex 29 | ¹H NMR (400 MHz, d6-DMSO): δ 9.15 (d, 0.6H, J = 8.50 Hz)*, 9.04 (d, 0.4H, J = 8.50 Hz)*, 8.06 (s, 1H), 7.97-7.77 (m, 6H), 7.67 (d, 1H, J = 8.65 Hz), 7.62-7.55 (m, 3H), 7.45-7.40 (m, 1H), 7.35-7.25 (m, 3H), 6.67-6.61 (m, 1H), 4.77-4.62 (m, 1H), 4.62-4.52 (m, 2H), 3.07 (s, 9H), 1.99-1.87 (m, 3H), 0.81 (q, 2H, J = 3.24 Hz), 0.66 (d, 1.5H, J = 6.76 Hz)*, 0.59 (d, 1.5H, J = 6.73 Hz)*. | Rt = 3.90 min, m/z = 647.4 [M]+ |
| 74 | 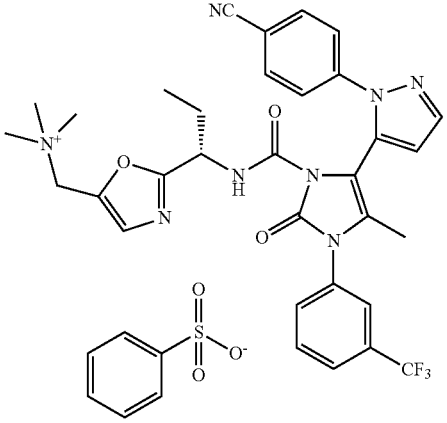 [SMILES: CC[C@H](NC(=O)n1c(-c2ccnn2-c2ccc(C#N)cc2)c(C)n(-c2cccc(C(F)(F)F)c2)c1=O)c1ncc(C[N+](C)(C)C)o1 ; O=S(=O)([O-])c1ccccc1] | See Ex 22 | Ex 29 | ¹H NMR (400 MHz, d6-DMSO): δ 9.06-8.98 (m, 1H), 8.04 (s, 1H), 7.96-7.81 (m, 6H), 7.67 (d, 1H, J = 8.95 Hz), 7.64-7.56 (m, 3H), 7.41 (s, 1H), 7.34-7.26 (m, 3H), 6.64 (d, 1H, J = 1.71 Hz), 4.75-4.59 (m, 3H), 3.07-2.94 (m, 9H), 1.99-1.86 (m, 3H), 1.86-1.52 (m, 2H), 0.75 (t, 1H, J = 7.27 Hz), 0.57 (t, 2H, J = 7.27 Hz). | Rt = 3.80 min, m/z = 633.4 [M]+ |
| 75 | 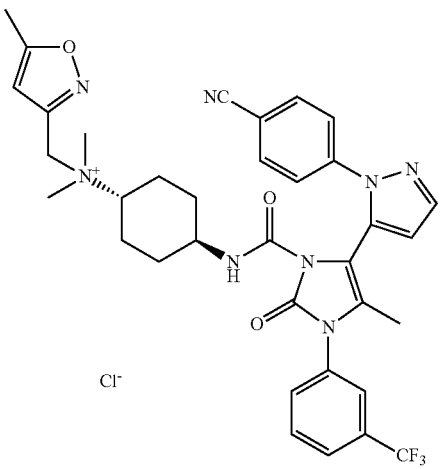 [SMILES: Cc1cc(C[N+](C)(C)[C@H]2CC[C@H](NC(=O)n3c(-c4ccnn4-c4ccc(C#N)cc4)c(C)n(-c4cccc(C(F)(F)F)c4)c3=O)CC2)no1 ; [Cl-]] | See Ex 9 | Ex 30 (using 3-Chloromethyl-5-methyl-isoxazole) | ¹H NMR (400 MHz, d6-DMSO): δ 8.21 (1H, d J = 7.4 Hz), 8.01 (1H, s), 7.93-7.88 (3H, m), 7.88-7.80 (3H, m), 7.67 (2H, d J = 8.8 Hz), 6.64 (1H, d J = 1.8 Hz), 6.51 (1H, d J = 0.8 Hz), 4.63 (2H, s), 3.36-3.15 (1H signal part obscured by water), 2.99 (6H, s), 2.48 (3H, s signal part obscured by solvent), 2.22-2.10 (2H, m), 1.96-1.80 (4H, m), 1.75-1.50 (3H, m), 1.32-1.02 (3H, m). | Rt = 3.96 min, m/z = 673.4 [M]+ |

-continued

| Ex. | Structure | Amine | Quat. Method | 1H NMR | LC-MS Method 3 |
|---|---|---|---|---|---|
| 76 | 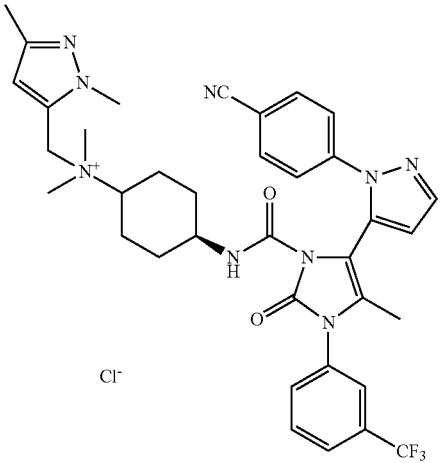 | See Ex 9 | Ex 30 (using 5-Chloromethyl-1,3-dimethyl-1H-pyrazole) | $^1$H NMR (400 MHz, d6-DMSO): δ 8.32 (1H, d J = 7.5 Hz), 8.02 (1H, s), 7.94-7.89 (3H, m), 7.88-7.80 (3H, m), 7.68 (2H, d J = 8.8 Hz), 6.65 (1H, d J = 1.7 Hz), 6.31 (1H, s), 4.58 (2H, s), 3.82 (3H, s), 3.50-3.20 (1H signal part obscured by water), 2.86 (6H, s), 2.24-2.12 (5H, m), 2.02-1.82 (4H, m), 1.74-1.52 (4H, m), 1.36-1.20 (1H, m), 1.18-1.06 (1H, m). | Rt = 3.87 min, m/z = 686.5 [M]+ |
| 77 | 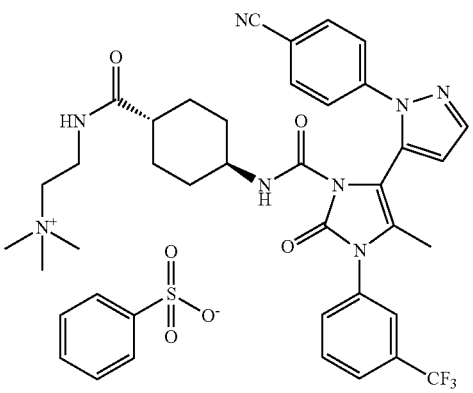 [SMILES: Cc1c(-c2ccnn2-c2ccc(C#N)cc2)n(C(=O)N[C@H]2CC[C@H](C(=O)NCC[N+](C)(C)C)CC2)c(=O)n1-c1cccc(C(F)(F)F)c1 ; O=S(=O)([O-])c1ccccc1] | Intermed. J | Ex 29 | $^1$H NMR (400 MHz, d6-DMSO): δ 8.19 (1H, d J = 7.4 Hz), 8.06 (1H, t J = 5.5 Hz), 8.01 (1H, s), 7.90-7.79 (6H, m), 7.66 (2H, d J = 8.8 Hz), 7.61-7.57 (2H, m), 7.34-7.27 (3H, m), 6.64 (1H, d J = 1.7 Hz), 3.47-3.40 (2H, m), 3.35-3.25 (2H, signal obscured by water), 3.20-3.10 (1H, m), 3.06 (9H, s), 2.08-1.98 (1H, m), 1.90 (3H, s), 1.78-1.64 (3H, m), 1.50-1.40 (1H, m), 1.39-1.10 (3H, m), 1.01-0.90 (1H, m). | Rt = 3.76 min, m/z = 663.4 [M]+ |
| 78 | 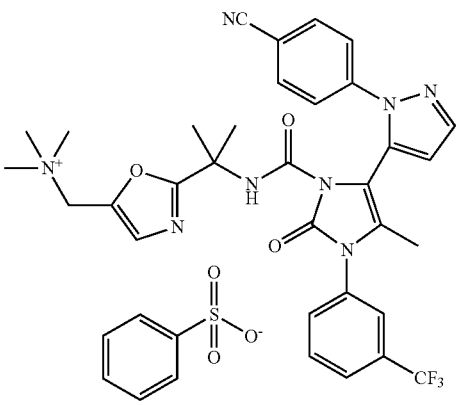 [SMILES: Cc1c(-c2ccnn2-c2ccc(C#N)cc2)n(C(=O)NC(C)(C)c2ncc(C[N+](C)(C)C)o2)c(=O)n1-c1cccc(C(F)(F)F)c1 ; O=S(=O)([O-])c1ccccc1] | See Ex 24 | Ex 29 | $^1$H NMR (400 MHz, d6-DMSO): δ 9.10 (s, 1H), 8.03 (s, 1H), 7.96-7.80 (m, 6H), 7.63-7.55 (m, 4H), 7.36-7.25 (m, 4H), 6.59 (d, 2H, J = 1.75 Hz), 4.63 (s, 2H), 2.95 (s, 9H), 1.91 (s, 3H), 1.40 (d, 6H) | Rt = 3.76 min, m/z = 633.4 [M]+ |

| Ex. | Structure | Amine | Quat. Method | 1H NMR | LC-MS Method 3 |
|---|---|---|---|---|---|
| 79 | 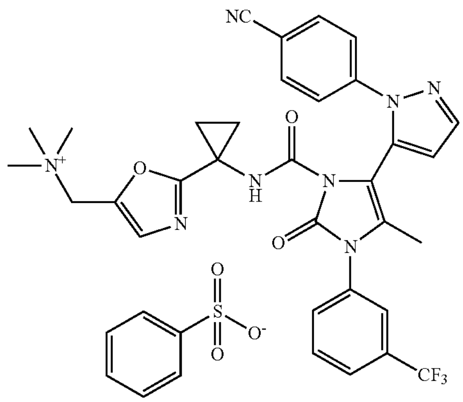 [SMILES: Cc1c(-c2ccnn2-c2ccc(C#N)cc2)n(C(=O)NC2(c3ncc(C[N+](C)(C)C)o3)CC2)c(=O)n1-c1cccc(C(F)(F)F)c1 ; O=S(=O)([O-])c1ccccc1] | See Ex 23 | Ex 29 | ¹H NMR (400 MHz, d6-DMSO): δ 9.11 (s, 1H), 8.03 (s, 1H), 7.95-7.83 (m, 6H), 7.65 (d, 2H, J = 8.85 Hz), 7.61-7.56 (m, 2H), 7.34-7.27 (m, 4H), 6.64 (d, 1H, J = 1.76), 4.59 (s, 2H), 2.97 (s, 9H), 1.91 (s, 3H), 1.38 (s, 2H), 1.32-1.18 (m, 1H), 0.82-0.67 (m, 1H). | Rt = 3.69 min, m/z = 631.3 [M]+ |
| 80 | 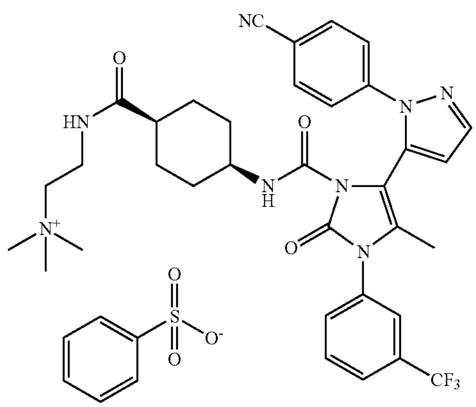 [SMILES: Cc1c(-c2ccnn2-c2ccc(C#N)cc2)n(C(=O)N[C@H]2CC[C@@H](C(=O)NCC[N+](C)(C)C)CC2)c(=O)n1-c1cccc(C(F)(F)F)c1 ; O=S(=O)([O-])c1ccccc1] | Intermed. K | Ex 29 | ¹H NMR (400 MHz, d6-DMSO): δ 8.52 (1H, d J = 7.1 Hz), 8.10-8.04 (2H, m), 7.94-7.80 (6H, m), 7.65 (2H, d J = 8.8 Hz), 7.61-7.57 (2H, m), 7.34-7.26 (3H, m), 6.64 (1H, d J = 1.8 Hz), 3.57-3.50 (1H, m), 3.48-3.40 (2H, m), 3.36-3.28 (1H, signal obscured by water), 3.07 (9H, s), 2.16-2.08 (2H, m), 1.94 (3H, s), 1.56-1.10 (8H, m). Aliphatic signals are broad overlapped and partially obscured by the water signal. | Rt = 3.67 min, m/z = 663.4 [M]+ |
| 81 | 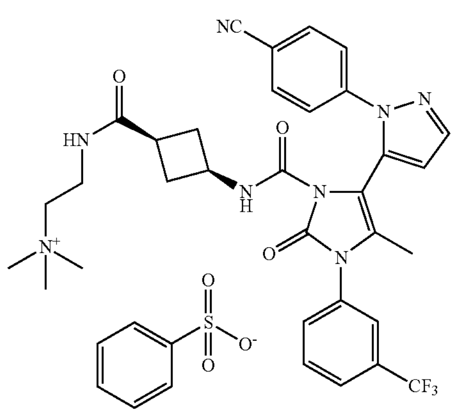 [SMILES: Cc1c(-c2ccnn2-c2ccc(C#N)cc2)n(C(=O)N[C@H]2C[C@@H](C(=O)NCC[N+](C)(C)C)C2)c(=O)n1-c1cccc(C(F)(F)F)c1 ; O=S(=O)([O-])c1ccccc1] | Intermed. P | Ex 29 | ¹H NMR (400 MHz, DMSO d6): δ 8.43 (1H, d J = 7.7 Hz), 8.08 (1H, t J = 5.7 Hz), 8.01 (1H, s), 7.92-7.80 (6H, m), 7.65 (2H, d J = 8.9 Hz), 7.61-7.57 (3H, m), 7.34-7.28 (5H, m) (bezylate ~1.6 eq), 6.64 (1H, d J = 1.8 Hz), 3.89-3.77 (1H, m), 3.49-3.41 (2H, m), 3.36-3.28 (peak obscured by water signal), 3.06 (9H, s), 2.65-2.55 (1H, m), 2.32-2.10 (2H, m), 1.98-1.85 (4H, m), 1.84-1.74 (1H, m). | Rt = 3.60 min, m/z = 635.4 [M]+ |

-continued

| Ex. | Structure | Amine | Quat. Method | 1H NMR | LC-MS Method 3 |
|---|---|---|---|---|---|
| 82 | 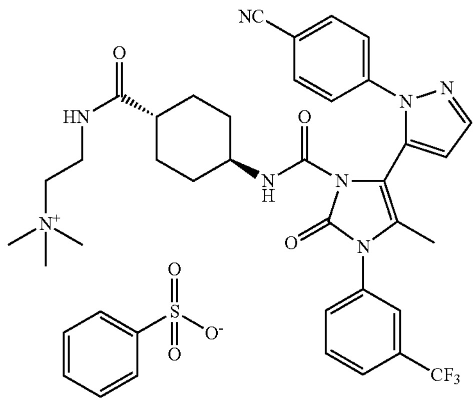 [SMILES: Cc1c(-c2ccnn2-c2ccc(C#N)cc2)n(C(=O)N[C@H]2CC[C@H](C(=O)NCC[N+](C)(C)C)CC2)c(=O)n1-c1cccc(C(F)(F)F)c1 ; O=S(=O)([O-])c1ccccc1] | Intermed. Q | Ex 29 | ¹H NMR (400 MHz, DMSO d6): δ 8.23 (1H, d J = 7.4 Hz), 8.02 (1H, s), 7.94-7.78 (6H, m), 7.67 (2H, d J = 8.4 Hz), 7.62-7.56 (2H, m), 7.34-7.26 (3H, m), 6.64 (1H, d J = 1.8 Hz), 4.42 (2H, br s), 3.65-3.60 (2H, m), 3.25-3.15 (1H, m), 3.10 (9H, s), 2.32-2.23 (1H, m), 1.92-1.80 (5H, m), 1.78-1.70 (1H, m), 1.50-1.14 (4H, m), 1.06-0.93 (1H, m). | Rt = 3.94 min, m/z = 664.4 [M]+ |
| 83 | 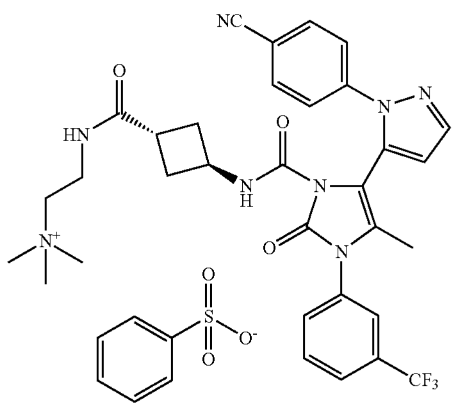 [SMILES: Cc1c(-c2ccnn2-c2ccc(C#N)cc2)n(C(=O)N[C@H]2C[C@H](C(=O)NCC[N+](C)(C)C)C2)c(=O)n1-c1cccc(C(F)(F)F)c1 ; O=S(=O)([O-])c1ccccc1] | Intermed. O | Ex 29 | ¹H NMR (400 MHz, DMSO d6): δ 8.45 (1H, d J = 7.6 Hz), 8.08 (1H, t J = 5.7 Hz), 8.00 (1H, s), 7.93-7.80 (6H, m), 7.65 (2H, d J = 8.8 Hz), 7.61-7.57 (2H, m), 7.34-7.26 (3H, m), 6.64 (1H, d J = 1.8 Hz), 4.12-4.00 (1H, m), 3.49-3.42 (2H, m), 3.35-3.30 (2H, signal obscured by water), 3.07 (9H, s), 2.83-2.74 (1H, m), 2.26-2.04 (3H, m), 1.96-1.86 (4H, m). | Rt = 3.66 min, m/z = 635.4 [M]+ |
| 84 | 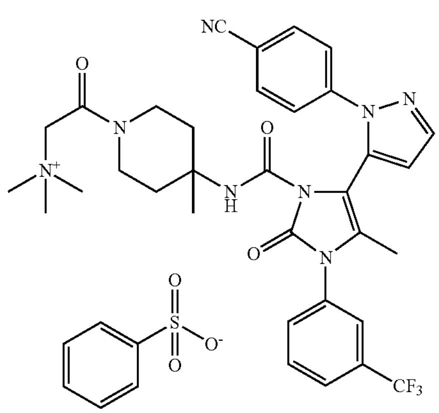 [SMILES: Cc1c(-c2ccnn2-c2ccc(C#N)cc2)n(C(=O)NC2(C)CCN(C(=O)C[N+](C)(C)C)CC2)c(=O)n1-c1cccc(C(F)(F)F)c1 ; O=S(=O)([O-])c1ccccc1] | See Ex 25 | Ex 29 | 1H H NMR (400 MHz, d6-DMSO): δ 8.43 (s, 1H), 8.03 (s, 1H), 7.96-7.80 (m, 6H), 7.65 (d, 2H, J = 7.84 Hz), 7.61-7.56 (m, 2H), 7.34-7.25 (m, 3H), 6.64 (d, 1H, J = 1.72 Hz), 4.44-4.25 (m, 2H), 3.91 (br s, 1H), 3.37 (br s, 1H), 3.20 (s, 9H), 3.06-2.92 (m, 1H), 2.88-2.68 (m, 1H), 1.95 (s, 3H), 1.86 (d, 1H, J = 13.33 Hz), 1.66 (t, 1H, J = 14.32 Hz), 1.49-1.19 (m, 2H), 1.00 (s, 3H). | Rt = 3.86 min, m/z = 649.4 [M]+ |

-continued

| Ex. | Structure | Amine | Quat. Method | 1H NMR | LC-MS Method 3 |
|---|---|---|---|---|---|
| 85 | 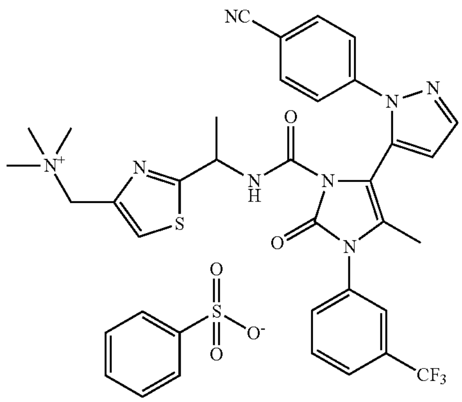 [SMILES: Cc1c(-c2ccnn2-c2ccc(C#N)cc2)n(C(=O)NC(C)c2nc(C[N+](C)(C)C)cs2)c(=O)n1-c1cccc(C(F)(F)F)c1 ; O=S(=O)([O-])c1ccccc1] | Intermed. I | Ex 29 | ¹H NMR (400 MHz, d6-DMSO): δ 9.11 and 9.05 (1H, 2 x d, J = 7.1 Hz)*, 8.08-8.01 (1H, m), 7.97-7.80 (6H, m), 7,72-7.61 (3H, m), 7.61-7.56 (2H, m), 7.35-7.26 (3H, m), 6.65 (1H, s), 4.99-4.88 (1H, m), 4.58 and 4.56 (2H, 2 x s)*, 3.02 and 3.04 (9H, 2 x s)*, 1.94 and 1.92 (3H, 2 x s)*, 1.45 and 1.29, 2 x d, J = 7 Hz)*. | Rt = 3.79 min, m/z = 635.3 [M]+ |
| 86 | 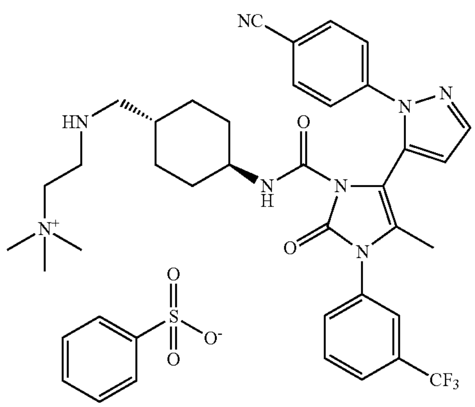 [SMILES: Cc1c(-c2ccnn2-c2ccc(C#N)cc2)n(C(=O)N[C@H]2CC[C@H](CNCC[N+](C)(C)C)CC2)c(=O)n1-c1cccc(C(F)(F)F)c1 ; O=S(=O)([O-])c1ccccc1] | See Ex 27 | Ex 29 | ¹H NMR (400 MHz, d6-DMSO): δ 8.50-8.36 (0.5H, m)*, 8.18 (0.5H, d, J = 7.52 Hz)*, 8.03-7.96 (1H, m), 7.94-7.72 (7H, m), 7.72-7.63 (2H, m), 7.63-7.54 (2H, m), 7.36-7.25 (3H, m), 6.72 (0.4H, d, J = 1.80 Hz)*, 6.63 (0.6 Hz, d, J = 1.75 Hz)*, 4.08-4.03 (2H, m), 3.63-3.56 (1H, m), 3.21-3.17 (9H, m), 3.03-2.90 (2H, m), 2.04-1.95 (0.6H, m)*, 1.90 (L4H, s)*, 1.81-1.55 (4H, m), 1.47-1.20 (2H, m), 1.03-0.79 (2H, m). | Rt = 3.85 min, m/z = 663.5 [M]+ |
| 87 | 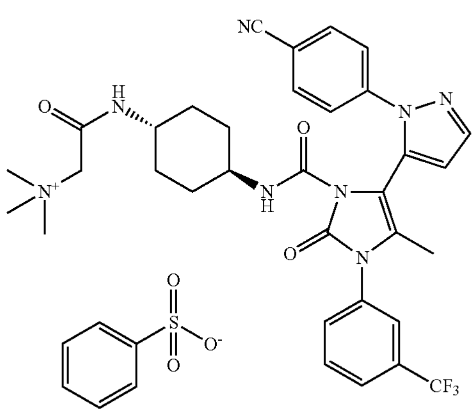 [SMILES: Cc1c(-c2ccnn2-c2ccc(C#N)cc2)n(C(=O)N[C@H]2CC[C@H](NC(=O)C[N+](C)(C)C)CC2)c(=O)n1-c1cccc(C(F)(F)F)c1 ; O=S(=O)([O-])c1ccccc1] | See Ex 26 | Ex 29 | ¹H NMR (400 MHz, d6-DMSO): δ 8.38 (1H, d, J = 7.60 Hz), 8.23 (1H, d, J = 7.42 Hz), 8.01 (1H, s), 7.94-7.78 (6H, m), 7.66 (2H, d, J = 8.82 Hz), 7.62-7.56 (2H, m), 7.34-7.26 (3H, m), 6.64 (1H, d, J = 1.75 Hz), 4.00 (2H, s), 3.58-3.46 (1H, m), 3.18 (10H, s), 1.89 (3H, s), 1.79-1.66 (3H, m), 1.46-1.37 (1H, m), 1.33-0.96 (4H, m). | Rt = 3.84 min, m/z = 649.3 [M]+ |

-continued

| Ex. | Structure | Amine | Quat. Method | 1H NMR | LC-MS Method 3 |
|---|---|---|---|---|---|
| 88 | 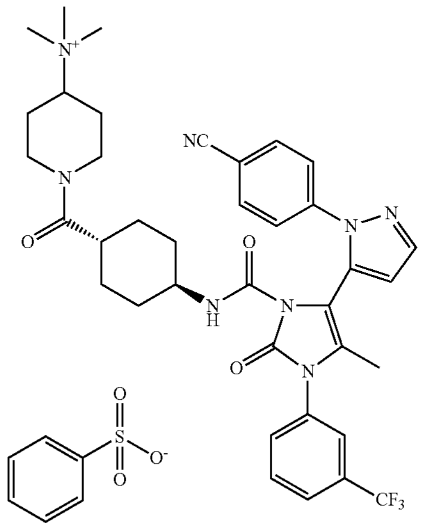 [SMILES: O=S(=O)([O-])c1ccccc1 ; Cc1c(-c2ccnn2-c2ccc(C#N)cc2)n(C(=O)N[C@H]2CC[C@H](C(=O)N3CCC([N+](C)(C)C)CC3)CC2)c(=O)n1-c1cccc(C(F)(F)F)c1] | Intermed. R | Ex 29 | ¹H NMR (400 MHz, CDCl₃) δ 8.32 (1H, d, J = 7.0 Hz), 7.88-7.78 (3H, m), 7.78-7.66 (4H, m), 7.64-7.56 (3H, m), 7.56-7.49 (1H, m), 7.39-7.31 (3H, m), 6.65 (1H, d, J = 1.5 Hz), 4.81-4.67 (1H, m), 4.31-4.09 (1H, m), 3.99-3.88 (1H, m), 3.50-3.37 (1H, m), 3.35-3.09(10H, m), 2.66-2.51 (1H, m), 2.46-2.27(2H, m), 2.23-2.10(1H, m), 2.03-1.94 (1H, m), 1.93-1.85 (3H, m), 1.85-1.36 (7H, m), 1.22-0.95 (2H, m). | Rt = 3.80 min, m/z = 703 [M]+ |
| 89 | 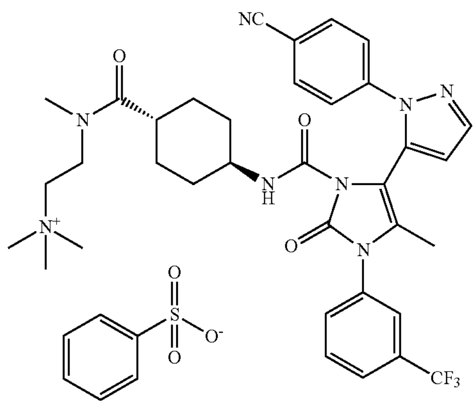 [SMILES: Cc1c(-c2ccnn2-c2ccc(C#N)cc2)n(C(=O)N[C@H]2CC[C@H](C(=O)N(C)CC[N+](C)(C)C)CC2)c(=O)n1-c1cccc(C(F)(F)F)c1 ; O=S(=O)([O-])c1ccccc1] | Intermed. L | Ex 29 | ¹H NMR (400 MHz, CDCl₃) δ 8.35 (1H, d, J = 7.6 Hz), 7.89-7.84 (2H, m), 7.81 (1H, d, J = 1.8 Hz), 7.78-7.66 (4H, m), 7.64-7.56 (3H, m), 7.54-7.51 (1H, m), 7.39-7.32 (3H, m), 6.56 (1H, d, J = 1.6 Hz), 3.89-3.71 (4H, m), 3.52-3.39 (1H, m), 3.34 (9H, s), 3.13 (3H, s), 2.38 (1H, tt, J = 11.7, 6.4 Hz), 2.04-1.96 (1H, m), 1.91-1.79 (4H, m), 1.75-1.66 (2H, m), 1.52-1.39 (2H, m), 1.26-1.01 (2H, m). | Rt = 3.85 min, m/z = 677 [M]+ |
| 90 | 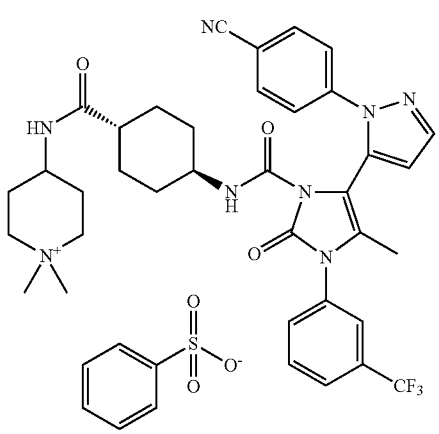 [SMILES: Cc1c(-c2ccnn2-c2ccc(C#N)cc2)n(C(=O)N[C@H]2CC[C@H](C(=O)NC3CC[N+](C)(C)CC3)CC2)c(=O)n1-c1cccc(C(F)(F)F)c1 ; O=S(=O)([O-])c1ccccc1] | Intermed. S | Ex 29 | ¹H NMR (400 MHz, CDCl₃) δ 8.15 (1H, d, J = 7.7 Hz), 8.10 (1H, d, J = 8.1 Hz), 7.88-7.82 (2H, m), 7.80 (1H, d, J = 1.9 Hz), 7.77-7.66 (3H, m), 7.65-7.62 (1H, m), 7.62-7.52 (3H, m), 7.40-7.35 (3H, m), 6.54 (1H, d, J = 1.9 Hz), 4.21-4.11 (1H, m), 4.05-3.93 (2H, m), 3.51 (3H, m), 3.37-3.24 (3H, m), 3.19-3.11 (3H, s), 2.23-2.09 (2H, m), 2.04-1.90 (3H, m), 1.89-1.83 (3H, m), 1.81-1.72 (1H, m), 1.70-1.53 (4H, m), 1.42-1.28 (2H, m), 0.87-0.63 (2H, m). | Rt = 3.79 min, m/z = 689 [M]+ |

| Ex. | Structure | Amine | Quat. Method | 1H NMR | LC-MS Method 3 |
|---|---|---|---|---|---|
| 91 | 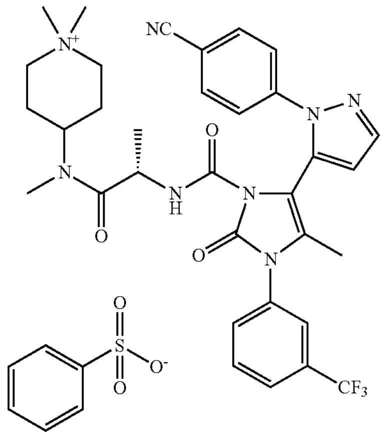 [SMILES: O=S(=O)([O-])c1ccccc1 ; Cc1c(-c2ccnn2-c2ccc(C#N)cc2)n(C(=O)N[C@@H](C)C(=O)N(C)C2CC[N+](C)(C)CC2)c(=O)n1-c1cccc(C(F)(F)F)c1] | See Ex 28 | Ex 29 | $^1$H NMR (400 MHz, d6-DMSO): δ 9.01 (1H, td, J = 6.47, 56.69 Hz), 8.03 (1H, d, J = 7.69 Hz), 7.97-7.78 (6H, m), 7.72-7.63 (2H, m), 7.61-7.56 (2H, m), 7.35-7.26 (3H, m), 6.67-6.62 (2H, m), 4.58-4.26 (2H, m), 3.56-3.36 (4H, m), 3.19-3.01 (6H, m), 2.84 (2H, d, J = 9.09 Hz), 2.76 (1H, d, J = 14.75 Hz), 2.27-1.99 (2H, m), 1.94 (2H, d, J = 7.62 Hz), 1.88 (1H, d, J = 5.27 Hz), 1.67-1.44 (2H, m), 1.12 (1.5H, d, J = 6.63 Hz)*, 0.83 (1.5H, t, J = 6.84 Hz)*. | Rt = 3.65 min, m/z = 649.3 [M]+ |

Example 92. {2-[(4-{[5-[2-(4-Cyano-phenyl)-2H-pyrazol-3-yl]-4-methyl-2-oxo-3-(3-trifluoromethyl-phenyl)-2,3-dihydro-imidazole-1-carbonyl]-amino}-piperidine-1-carbonyl)-amino]-ethyl}-trimethyl-ammonium benzene sulfonate

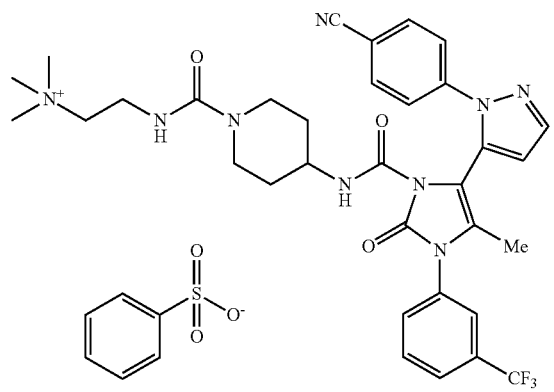 [SMILES: Cc1c(-c2ccnn2-c2ccc(C#N)cc2)n(C(=O)NC2CCN(C(=O)NCC[N+](C)(C)C)CC2)c(=O)n1-c1cccc(C(F)(F)F)c1 ; O=S(=O)([O-])c1ccccc1]

Intermediate 92A. 4-{[5-[2-(4-Cyano-phenyl)-2H-pyrazol-3-yl]-4-methyl-2-oxo-3-(3-trifluoromethyl-phenyl)-2,3-dihydro-imidazole-1-carbonyl]-amino}-piperidine-1-carboxylic acid tert-butyl ester

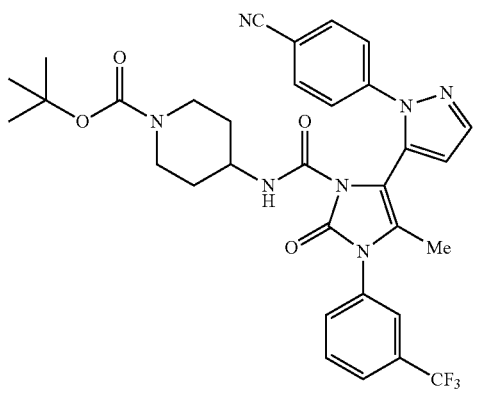 [SMILES: Cc1c(-c2ccnn2-c2ccc(C#N)cc2)n(C(=O)NC2CCN(C(=O)OC(C)(C)C)CC2)c(=O)n1-c1cccc(C(F)(F)F)c1]

Intermediate 92A was synthesized from 4-amino-1-BOC-piperidine by the method of Example 1 in a yield of 85%

LCMS (Method U2) Rt=2.03 min., m/z=658.4 [M+Na]+

Intermediate 92B. 5-[2-(4-Cyano-phenyl)-2H-pyrazol-3-yl]-4-methyl-2-oxo-3-(3-trifluoromethyl-phenyl)-2,3-dihydro-imidazole-1-carboxylic acid piperidin-4-ylamide

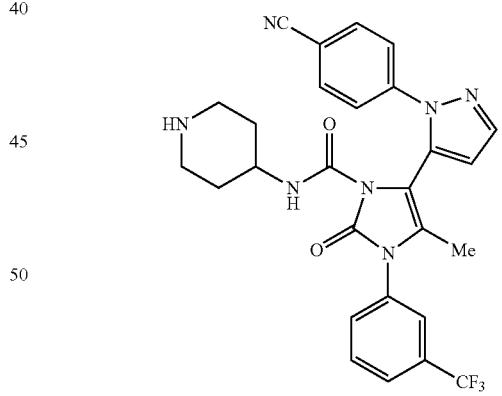

Intermediate 92A (525 mg, 0.83 mmol) was stirred in DCM (6 mL) with TFA (1.5 mL) and water (50 mg) for 1.5 h. The mixture was diluted with more DCM and washed with aqueous NaHCO$_3$ solution. The aqueous phase was extracted with more DCM and the combined organics dried over Na$_2$SO$_4$ and evaporated to give Intermediate 92B as a pale yellow foam (466 mg).

LCMS (Method U2) Rt=1.30 min., m/z=536.3 [M+H]+

107

Intermediate 92C. 4-{[5-[2-(4-Cyano-phenyl)-2H-pyrazol-3-yl]-4-methyl-2-oxo-3-(3-trifluoromethyl-phenyl)-2,3-dihydro-imidazole-1-carbonyl]amino}-piperidine-1-carboxylic acid (2-dimethylamino-ethyl)-amide

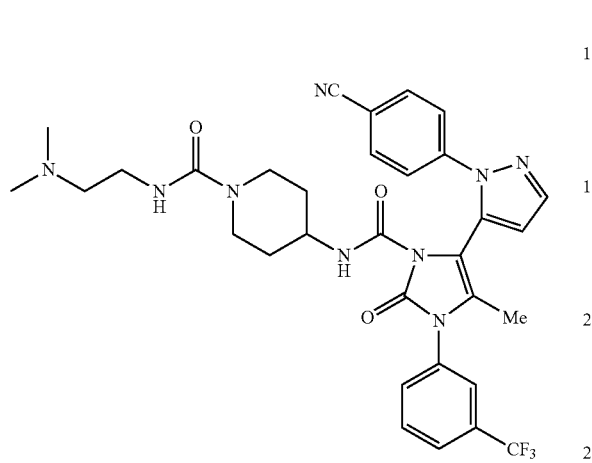

1,1'-Carbonyldiimidazole (73.5 mg, 0.45 mmol) was stirred in dry THF (1.5 mL) as N,N-dimethylethylenediamine (35 mg, 0.40 mmol) was added. After stirring for 10 min., a solution of Intermediate 92B (175 mg, 0.33 mmol) in dry THF (1.5 mL) was added. The mixture was stirred for 5 h and the solvent evaporated and the concentrate was partitioned between EtOAc and water. The organic phase was washed with water and with brine, dried (Na$_2$SO$_4$) and evaporated. Purified by SPE on silica (5 g) eluting with 5% MeOH in DCM with additional 2M methanolic ammonia (1%, 2%, 3% and 4%) added stepwise to afford Intermediate 92C (121 mg, 57%).

LCMS (Method 7) Rt=2.41 min., m/z=650.1 [M+H]+

{2-[(4-{[5-[2-(4-Cyano-phenyl)-2H-pyrazol-3-yl]-4-methyl-2-oxo-3-(3-trifluoromethyl-phenyl)-2,3-dihydro-imidazole-1-carbonyl]-amino}-piperidine-1-carbonyl)-amino]-ethyl}-trimethyl-ammonium benzene sulfonate The title compound was prepared from Intermediate 92C using the method in Example 29.

$^1$H NMR (400 MHz, d6-DMSO): δ 8.30 (1H, d, J=7.0 Hz), 8.01 (1H, br s), 7.93-7.88 (3H, m), 7.88-7.79 (3H, m), 7.69-7.64 (2H, m), 7.61-7.56 (2H, m), 7.35-7.26 (3H, m), 6.82 (1H, t, J=5.8 Hz), 6.64 (1H, d, J=1.8 Hz), 3.63 (2H, br t, J=15 Hz), 3.48-3.36 (3H, m), 3.35-3.29 (2H, m, partially obscured by water), 3.07 (9H, s), 2.82 (2H, br t, J=11.4 Hz), 1.91 (3H, s), 1.67-1.56 (1H, m), 1.42-1.32 (1H, m), 1.28-1.15 (1H, m), 1.07-0.93 (1H, m).

LCMS (Method 3) Rt=3.74 min, m/z=665.3 [M]+

108

Example 93. [2-(4-{[5-[2-(4-Cyano-phenyl)-2H-pyrazol-3-yl]-4-methyl-2-oxo-3-(3-trifluoromethyl-phenyl)-2,3-dihydro-imidazole-1-carbonyl]-amino}-piperidine-1-carbonyloxy)-ethyl]-trimethyl-ammonium benzene sulfonate

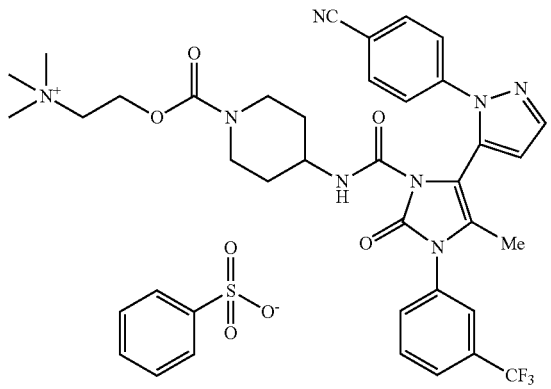 [SMILES: Cc1c(-c2ccnn2-c2ccc(C#N)cc2)n(C(=O)NC2CCN(C(=O)OCC[N+](C)(C)C)CC2)c(=O)n1-c1cccc(C(F)(F)F)c1 ; O=S(=O)([O-])c1ccccc1]

Intermediate 93A. 4-{[5-[2-(4-Cyano-phenyl)-2H-pyrazol-3-yl]-4-methyl-2-oxo-3-(3-trifluoromethyl-phenyl)-2,3-dihydro-imidazole-1-carbonyl]-amino}-piperidine-1-carboxylic acid 2-dimethylamino-ethyl ester

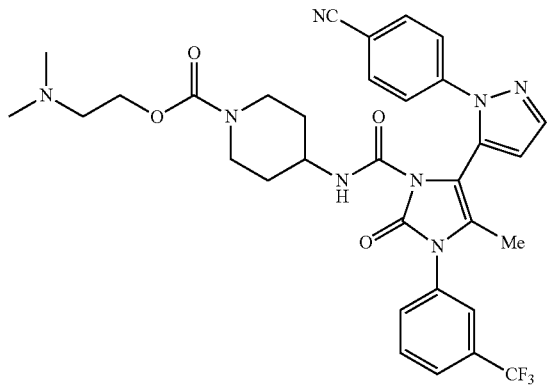 [SMILES: Cc1c(-c2ccnn2-c2ccc(C#N)cc2)n(C(=O)NC2CCN(C(=O)OCCN(C)C)CC2)c(=O)n1-c1cccc(C(F)(F)F)c1]

Intermediate 93A was synthesized by a similar procedure to Intermediate 92C, using N,N-dimethylethanolamine. The mixture of 1,1'-carbonyldiimidazole (21 mg, 0.13 mmol) and N,N-dimethylethanolamine (10 mg, 0.11 mmol) was stirred for 1 h prior to addition of Intermediate 92B (50 mg, 0.093 mmol). Purification by silica SPE (5 g) eluting with 5% and 10% MeOH in DCM afforded Intermediate 93A (25 mg, 42%).

LCMS (Method U2) Rt=1.38 min., m/z=651.4 [M+H]+

[2-(4-{[5-[2-(4-Cyano-phenyl)-2H-pyrazol-3-yl]-4-methyl-2-oxo-3-(3-trifluoromethyl-phenyl)-2,3-dihydro-imidazole-1-carbonyl]-amino}-piperidine-1-carbonyloxy)-ethyl]-trimethyl-ammonium benzene sulfonate The title compound was prepared from Intermediate 93A using the method in Example 29.

¹H NMR (400 MHz, d6-DMSO): δ 8.33 (1H, d, J=7.1 Hz), 8.02 (1H, s), 7.95-7.88 (3H, m), 7.88-7.80 (3H, m), 7.66 (2H, m), 7.62-7.59 (2H, m), 7.35-7.26 (3H, m), 6.64 (1H, d, J=1.6 Hz), 4.41 (2H, s), 3.74-3.56 (4H, m), 3.53-3.41 (1H, m), 3.10 (9H, s), 2.96 (2H, br s), 1.92 (3H, s), 1.74-1.58 (1H, m), 1.46-1.19 (2H, m), 1.13-0.97 (1H, m).

LCMS (Method 3) Rt=3.71 min, m/z=664.3 [M]+

Example 94. [2-(4-{[1-(4-Cyano-phenyl)-5'-methyl-2'-oxo-1'-(3-trifluoromethyl-phenyl)-1',2'-dihydro-1H-[2,4']biimidazolyl-3'-carbonyl]-amino}-piperidin-1-yl)-2-oxo-ethyl]-trimethyl-ammonium benzene sulfonate

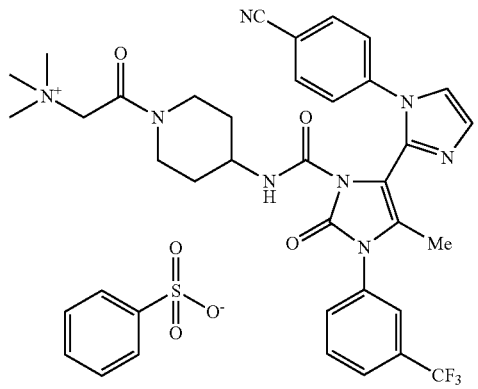 [SMILES: Cc1c(-c2nccn2-c2ccc(C#N)cc2)n(C(=O)NC2CCN(C(=O)C[N+](C)(C)C)CC2)c(=O)n1-c1cccc(C(F)(F)F)c1 ; O=S(=O)([O-])c1ccccc1]

Intermediate 94A.
4-(2-Bromo-imidazol-1-yl)-benzonitrile

4-Imidazol-1-yl-benzonitrile (5.0 g, 29.6 mmol) was dissolved in dioxane and N-bromosuccinimide (5.26 g, 29.6 mmol) was added. The solution was heated at 60° C. for 2 h. The solution was decanted from a gummy residue and evaporated to give a yellow solid. This was triturated with EtOAc to give a cream solid which was further purified by chromatography using EtOAc as eluant to afford Intermediate 11 (0.79 g) as a pale yellow solid.

LCMS (Method 1) Rt=2.44 min., m/z 248 and 250 (Br isotopes)

Intermediate 94B. 4-[2'-Ethoxy-5'-methyl-1'-(3-trifluoromethyl-phenyl)-1'H-[2,4']biimidazolyl-1-yl]-benzonitrile

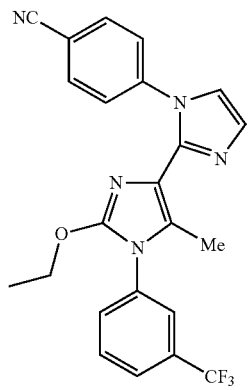 [SMILES: CCOc1nc(-c2nccn2-c2ccc(C#N)cc2)c(C)n1-c1cccc(C(F)(F)F)c1]

2-Dicyclohexylphosphino-2',4',6'-triisopropylbiphenyl (19 mg, 0.04 mmol), (2-dicyclohexylphosphino-2',4',6'-triisopropyl-1,1'-biphenyl)palladium(II) dichloride (15.7 mg, 0.02 mmol), tetrahydroxydiboron (270 mg, 3 mmol) and potassium acetate (294 mg, 3 mmol) were mixed in a nitrogen filled vial. A solution of 4-bromo-2-ethoxy-5-methyl-1-[3-(trifluoromethyl)phenyl]-1H-imidazole (Intermediate A4, 349 mg, 1 mmol) in IMS (10 ml) was added and the solution heated at 80° C. for 2 h. A solution of K₂CO₃ (1.8M, 1.66 ml) was added followed by a suspension of 4-(2-bromo-imidazol-1-yl)-benzonitrile (Intermediate 94A, 248 mg, 1 mmol) in THF. Heating was continued overnight at 80° C. After cooling, the mixture was filtered through celite, washing with EtOAc, and evaporated to dryness. The residue was extracted into EtOAc, decanted, dried over Na₂SO₄ filtered and evaporated. Purification was performed by silica gel chromatography eluting with 20% to 100% EtOAc-cyclohexane. The third eluted component was the title compound (91 mg, 21%).

LCMS (Method 2) Rt=2.73 min., m/z 438.3

Intermediate 94C. 4-[5'-Methyl-2'-oxo-1'-(3-trifluoromethyl-phenyl)-2',3'-dihydro-1'H-[2,4']biimidazolyl-1-yl]-benzonitrile

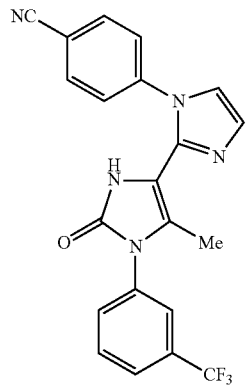 [SMILES: Cc1c(-c2nccn2-c2ccc(C#N)cc2)[nH]c(=O)n1-c1cccc(C(F)(F)F)c1]

4-[2'-Ethoxy-5'-methyl-1'-(3-trifluoromethyl-phenyl)-1'H-[2,4']biimidazolyl-1-yl]-benzonitrile (Intermediate 94B, 170 mg, 0.39 mmol), acetone (5 ml) and 1M HCl (3 ml) were heated together at 60° C. for 3.5 h. Concentrated HCl (0.5 ml) was added and heating continued overnight. The mixture was cooled and most of the acetone removed by evaporation. The solution was basified with aqueous NaHCO$_3$ and the white solid title compound filtered off and dried at 50° C. Yield 150 mg (94%).

LCMS (Method 3): Rt=3.61 min, m/z 410.1 [M+H]+

$^1$H NMR (400 MHz, d6-DMSO): δ 10.47 (1H, s), 8.05-7.99 (2H, m), 7.79-7.73 (3H, m), 7.72 (1H, d, J=1.4 Hz), 7.68-7.63 (1H, m), 7.63-7.58 (2H, m), 7.28 (1H, d, J=1.4 Hz), 1.70 (3H, s).

Intermediate 94D. 1-(4-Cyano-phenyl)-5'-methyl-2'-oxo-1'-(3-trifluoromethyl-phenyl)-1',2'-dihydro-1H-[2,4']biimidazolyl-3'-carboxylic acid [1-(2-dimethyl-amino-acetyl)-piperidin-4-yl]-amide

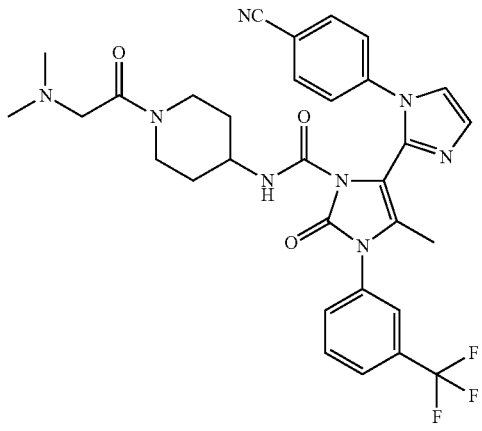 [SMILES: Cc1c(-c2nccn2-c2ccc(C#N)cc2)n(C(=O)NC2CCN(C(=O)CN(C)C)CC2)c(=O)n1-c1cccc(C(F)(F)F)c1]

To intermediate 94C (50 mg, 0.122 mmol) in DCM (2 mL) was added triethylamine (25 mg, 0.244 mmol) and 4-nitrophenyl chloroformate (30 mg, 0.146 mmol). The mixture was stirred for 1 h at room temperature. 1-(4-Amino-piperidin-1-yl)-2-dimethyl-amino-ethanone (45 mg, 0.244 mmol) in DCM (0.5 ml) was added and the mixture was stirred for 3 h. The mixture was partitioned between DCM and 10% K$_2$CO$_3$ solution, the aqueous extracted a further ×2 with DCM and the combined extracts dried (MgSO$_4$) and evaporated.

LCMS (Method U2) Rt=0.99 min, m/z=621 [M+H]+. The product was used without purification for the next step.

[2-(4-{[1-(4-Cyano-phenyl)-5'-methyl-2'-oxo-1'-(3-trifluoromethyl-phenyl)-1',2'-dihydro-1H-[2,4']biimidazolyl-3'-carbonyl]-amino}-piperidin-1-yl)-2-oxo-ethyl]-trimethyl-ammonium benzene sulfonate The crude Intermediate 94D (0.12 mmol) was stirred with methyl benzenesulphonate (23 mg, 0.13 mmol) in THF (0.5 mL) at 20° C. overnight. The product was purified by HPLC (C18, 0% to 50% acetonitrile/water containing 0.1% formic acid. The appropriate fractions were freeze dried to give the title compound (34 mg, 35%). $^1$H NMR (400 MHz, d6-DMSO): δ 8.49 (1H, s), 8.25 (1H, d, J=7.25 Hz), 7.98 (1H, s), 7.96 (2H, d, J=8.75 Hz), 7.91-7.86 (1H, m), 7.86-7.77 (2H, m), 7.72 (1H, d, J=1.42 Hz), 7.61-7.57 (1H, m), 7.55 (2H, d, J=8.72 Hz), 7.21 (1H, d, J=1.41 Hz), 4.43 (2H, s), 4.07-3.94 (1H, m), 3.65-3.45 (2H, m), 3.21 (9H, s), 3.15-3.00 (2H, m), 2.94-2.82 (1H, m), 1.90 (3H, s), 1.65 (2H, br s), 1.44-1.03 (3H, m).

LCMS (Method 3) Rt=3.16 min, m/z=635.3 [M]+.

Biological Assay

Compounds of this invention were tested for potency in a human neutrophil elastase (FINE) enzyme activity assay.

HNE Enzyme Assay

Assays were performed in 96-well plates in a total assay volume of 100 μL. The final concentration of elastase enzyme (human leukocyte elastase, Sigma E8140) was 0.00072 U/mL. The peptide substrate (MeOSuc-Ala-Ala-Pro-Val-AMC, Calbiochem #324740) was used at a final concentration of 100 μM. The final concentration of DMSO was 1% in the assay buffer (0.05M Tris.HCl, 0.1 M NaCl, 0.1M CaCl$_2$, 0.0005% brij-35, pH 7.5). The enzymatic reaction was started by addition of the enzyme and incubated at 25° C. for 30 minutes. After incubation, the reaction was stopped by addition of soybean trypsin inhibitor (Sigma T9003) at a final concentration of 50 μg/well. Fluorescence was measured using a Molecular Devices fluorescence plate reader using 380 nm excitation and 460 nm emission wavelengths.

A concentration response to each compound was performed and the effect of compound in each experiment was expressed as a percentage inhibition of the control enzyme fluorescence. Dose response curves were plotted and compound potency (IC$_{50}$) was determined. Compounds were tested in at least two separate experiments. IC$_{50}$ values for tested Examples, representative of the invention, are shown in Table:

TABLE

| Example | HNE inhibition |
| --- | --- |
| 1, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 34, 35, 36, 37, 38, 39, 40, 41, 42, 43, 44, 47, 49, 50, 51, 56, 57, 58, 59, 60, 61, 62, 63, 64, 65, 66, 67, 68, 69, 70, 71, 72, 73, 74, 75, 76, 77, 78, 79, 82, 83, 84, 85, 86, 87, 88, 89, 90, 91, 92, 93, 94 | ++++ |
| 2, 33, 45, 46, 48, 52, 53, 54, 55, 59, 80 | +++ |

In the table above, FINE enzyme inhibition (IC$_{50}$ values) are indicated as follows:
1-10 nM '+1+++';
<1 nM '++++'.

LPS/fMLP Model

Male Sprague-Dawley rats were lightly anaesthetised and given vehicle (for example 0.2% Tween 80 in saline for wet formulation studies or lactose for dry powder studies) or compound, i.t., at the desired pre-dose time (prior to fMLP administration e.g. 1 h, 12 h or 24 h)

Four hours prior to fMLP administration, animals were lightly anaesthetized and given LPS (for example 0.5 ml/kg of 20 μg/ml PBS solution) by the i.t. route. Thirty to forty minutes prior to fMLP-administration, animals were terminally anaesthetised with urethane. Animals were placed on a heat mat and anaesthesia was maintained until animals were killed and subjected to BAL.

Four hours after LPS-challenge, rats were given fMLP (for example 0.5 ml/kg of 0.6 mg/ml PBS solution) by the i.t. route.

Animals were killed one hour after fMLP-administration, the trachea cannulated and BALF collected. An elastase activity assay was performed to determine the level of elastase present in the BALF.

HNE Model

Male Sprague-Dawley rats were lightly anaesthetized and given vehicle (for example 0.2% Tween 80 in saline for wet formulation studies or lactose for dry powder studies) or compound, i.t.

Thirty to forty minutes prior to HNE-administration, animals were terminally anaesthetised with urethane. Animals were placed on a heat mat and anaesthesia was maintained until animals were killed for BAL.

Three hours after compound/vehicle administration, animals were given PBS as control or FINE (for example 0.1 ml of a 1000U/ml solution in PBS) by the i.t. route.

Animals were killed one hour after iHNE-administration, the trachea cannulated and BALF collected. Red blood cells accumulation in BALF was assessed spectrophotometrically, as a measure of BALF hemoglobin content.

Where a numerical limit or range is stated herein, the endpoints are included. Also, all values and subranges within a numerical limit or range are specifically included as if explicitly written out.

As used herein the words "a" and "an" and the like carry the meaning of "one or more."

Obviously, numerous modifications and variations of the present invention are possible in light of the above teachings. It is therefore to be understood that, within the scope of the appended claims, the invention may be practiced otherwise than as specifically described herein.

All patents and other references mentioned above are incorporated in full herein by this reference, the same as if set forth at length.

The invention claimed is:

1. A compound of formula (I):

(I)

wherein
A is:

X is:

$R_1$ is one of the following groups:

n is an integer from 1 to 4;
m is 0 or an integer from 1 to 4;
t is 0 or an integer from 1 to 4;
y is an integer from 1 to 4;
w is an integer from 1 to 4;
z is 0 or 1;
l is 0 or 1;
$R_2$ is —H or linear or branched —$(C_1$-$C_4)$alkyl;
$R_3$ is linear or branched —$(C_1$-$C_4)$alkyl or $R_2$ and $R_3$ may form together a cycloalkyl;
$R_4$ is -arylene-$(C_1$-$C_4)$alkylene-$NR_dR_e$, -arylene-$(C_1$-$C_4)$alkylene-$N^+R_aR_bR_c$, -heteroarylene-$(C_1$-$C_4)$alkylene-$NR_dR_e$, -heteroarylene-$(C_1$-$C_4)$alkylene-$N^+R_aR_bR_c$ and heteroaryl, wherein any of such arylene-$(C_1$-$C_4)$alkylene-$NR_dR_e$, -arylene-$(C_1$-$C_4)$alkylene-$N^+R_aR_bR_c$, -heteroarylene-$(C_1$-$C_4)$alkylene-$NR_dR_e$, -heteroarylene-$(C_1$-$C_4)$alkylene-$N^+R_aR_bR_c$ and heteroaryl may be optionally substituted by one or more —$(C_1$-$C_4)$alkyl or $R_4$ is one of the following groups:

$R_5$ is aryl-$(C_1$-$C_4)$alkylenoxy-, linear or branched $(C_1$-$C_4)$alkyl-OC(O)—NH—, —$(CH_2)_t$—$NR_dR_e$, —$(CH_2)_t$—$N^+R_aR_bR_c$, —C(O)—N($R_{10}$)$(C_1$-$C_4)$alkylene-$NR_dR_e$, —C(O)N($R_{10}$)$(C_1$-$C_4)$alkylene-$N^+R_aR_bR_c$, —C(O)O$(C_1$-$C_4)$alkylene-$NR_dR_e$, —C(O)O$(C_1$-$C_4)$alkylene-$N^+$ $R_aR_bR_c$, —(CH$_2$)$_t$NHC(O)—(C$_1$-C$_4$)alkylene-NR$_d$R$_e$, —(CH$_2$)NHC(O)—(C$_1$-C$_4$)alkylene-N$^+$R$_a$R$_b$R$_c$, or one of the following groups R$_6$ is —H, —(C$_1$-C$_4$)alkyl, aryl-(C$_1$-C$_4$)alkylene-OCO—, CF$_3$C(O)—, aryl-(C$_1$-C$_4$)alkylene, linear or branched (C$_1$-C$_4$)alkyl-OC(O)—, —C(O)—(C$_1$-C$_4$)alkylene-NR$_d$R$_e$, —C(O)—(C$_1$-C$_4$)alkylene-N$^+$R$_a$R$_b$R$_c$, —C(O)O—(C$_1$-C$_4$)alkylene-NR$_d$R$_e$, —C(O)O—(C$_1$-C$_4$)alkylene-N$^+$R$_a$R$_b$R$_c$—C(O)—N(R$_{10}$)(C$_1$-C$_4$)alkylene-NR$_d$R$_e$, or —C(O)N(R$_{10}$)(C$_1$-C$_4$)alkylene-N$^+$R$_a$R$_b$R$_c$;

R$_a$ is —(C$_1$-C$_4$)alkyl;

R$_b$ is —(C$_1$-C$_4$)alkyl;

R$_c$ is —(C$_1$-C$_4$)alkyl, aryl-(C$_1$-C$_4$)alkylene or heteroaryl-(C$_1$-C$_4$)alkylene, wherein said heteroaryl-(C$_1$-C$_4$)alkylene may be optionally substituted by one or more —(C$_1$-C$_4$)alkyl groups;

R$_d$ is —H or —(C$_1$-C$_4$)alkyl;

R$_e$ is —H or —(C$_1$-C$_4$)alkyl;

R$_7$ is —H or —(C$_1$-C$_4$)alkyl;

R$_8$ is —H or —(C$_1$-C$_4$)alkyl;

R$_9$ is heterocycloalkyl, heterocycloalkyl-(C$_1$-C$_4$)alkylene-, (C$_1$-C$_4$)alkylene-NR$_d$R$_e$ and (C$_1$-C$_4$)alkylene-N$^+$R$_a$R$_b$R$_c$;

R$_{10}$ is —H or —(C$_1$-C$_4$)alkyl; and

* and #, indicate the points of attachment for the radical groups to the rest of the molecule, wherein any of such heterocycloalkyl, aryl, heteroaryl and aryl-(C$_1$-C$_4$)alkylene may be optionally substituted by one or more groups independently selected from (C$_1$-C$_4$)alkyl and OR$_7$ and wherein the nitrogen atom in the heterocycloalkyl and heteroaryl groups may be quaternized, or a pharmaceutically acceptable salt thereof.

2. A compound or salt according to claim 1, wherein A is n is 2 or 3; m is 0 or 2; R$_7$ is —H; R$_5$ is aryl-(C$_1$-C$_4$)alkylenoxy-, linear or branched (C$_1$-C$_4$)alkyl-OC(O)—NH, C(O)O(C$_1$-C$_4$)alkylene-N$^+$R$_a$R$_b$R$_c$, —(CH$_2$)$_t$NHC(O)—(C$_1$-C$_4$)alkylene-NR$_d$R$_e$, —(CH$_2$)$_t$NHC(O)—(C$_1$-C$_4$)alkylene-N$^+$R$_a$R$_b$R$_c$, or —C(O)N(R$_{10}$)(C$_1$-C$_4$)alkylene-N$^+$R$_a$R$_b$R$_c$— wherein t is 0 or 1, R$_a$ and R$_b$ are independently —(C$_1$-C$_4$)alkyl, R$_c$ is —(C$_1$-C$_4$)alkyl, heteroaryl-(C$_1$-C$_4$)alkylene or aryl-(C$_1$-C$_4$)alkylene, R$_d$ and R$_e$ are independently —(C$_1$-C$_4$)alkyl, R$_{10}$ is —H or —(C$_1$-C$_4$)alkyl.

3. A compound or salt according to claim 1, wherein, A is n is 1 or 2; m is 1 or 2; R$_7$ is —H; R$_5$ is —(CH$_2$)$_t$—NR$_d$R$_e$, or —(CH$_2$)$_t$—N$^+$R$_a$R$_b$R$_c$, wherein t is 0 or 1, R$_a$ and R$_b$ are independently —(C$_1$-C$_4$)alkyl, R$_c$ is —(C$_1$-C$_4$)alkyl, heteroaryl-(C$_1$-C$_4$)alkylene or aryl-(C$_1$-C$_4$)alkylene.

4. A compound or salt according to claim 1, wherein A is n is 2; m is 2; R$_7$ is —H; R$_5$ is R$_a$ is —(C$_1$-C$_4$)alkyl; R$_b$ is —(C$_1$-C$_4$)alkyl; R$_{10}$ is —H or —(C$_1$-C$_4$)alkyl.

5. A compound or salt according to claim 1, wherein A is n is 2; m is 2; R$_7$ is —H; R$_5$ is

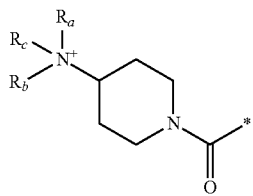

R$_a$ is —(C$_1$-C$_4$)alkyl; R$_b$ is —(C$_1$-C$_4$)alkyl; R$_c$ is —(C$_1$-C$_4$)alkyl.

6. A compound or salt according to claim 1, wherein A is

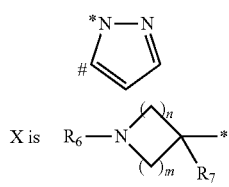

n is 2; m is 2; R$_7$ is —H or —(C$_1$-C$_4$)alkyl; R$_6$ is aryl-(C$_1$-C$_4$)alkylenoxy-, aryl-(C$_1$-C$_4$)alkylene-OCO—, CF$_3$C(O)—, —C(O)—(C$_1$-C$_4$)alkylene-NR$_d$R$_e$, —C(O)O—(C$_1$-C$_4$)alkylene-N$^+$R$_a$R$_b$R$_c$, —C(O)N(R$_{10}$)(C$_1$-C$_4$)alkylene-N$^+$R$_a$R$_b$R$_c$, or —C(O)—(C$_1$-C$_4$)alkylene-N$^+$R$_a$R$_b$R$_c$ wherein R$_d$ is —H or —(C$_1$-C$_4$)alkyl; R$_e$ is —H or —(C$_1$-C$_4$)alkyl, R$_a$ is —(C$_1$-C$_4$)alkyl; R$_b$ is —(C$_1$-C$_4$)alkyl; R$_c$ is selected from —(C$_1$-C$_4$)alkyl; R$_{10}$ is —H or —(C$_1$-C$_4$)alkyl.

7. A compound or salt according to claim 1, wherein A is

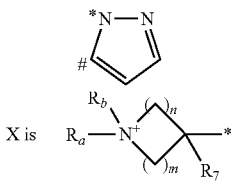

n is 1 or 2; m is 2; R$_7$ is —H or —(C$_1$-C$_4$)alkyl; R$_a$ and R$_b$ are each independently —(C$_1$-C$_4$)alkyl.

8. A compound or salt according to claim 1, wherein A is

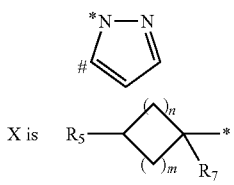

n is 2; m is 2; R$_7$ is —H; R$_5$ is —(CH$_2$)$_t$—N$^+$R$_a$R$_b$R$_c$, wherein t is 1, R$_a$ and R$_b$ are each independently —(C$_1$-C$_4$)alkyl, and R$_c$ is aryl-(C$_1$-C$_4$)alkylene.

9. A compound, which is selected in the group consisting of

5-[2-(4-cyano-phenyl)-2H-pyrazol-3-yl]-4-methyl-2-oxo-3-(3-trifluoromethyl-phenyl)-2,3-dihydro-imidazole-1-carboxylic acid trans-(4-dimethylaminomethyl-cyclohexyl)-amide;

5-[2-(4-cyano-phenyl)-2H-pyrazol-3-yl]-4-methyl-2-oxo-3-(3-trifluoromethyl-phenyl)-2,3-dihydro-imidazole-1-carboxylic acid ((1 S,2S)-2-benzyloxy-cyclopentyl)-amide;

4-{[5-[2-(4-cyano-phenyl)-2H-pyrazol-3-yl]-4-methyl-2-oxo-3-(3-trifluoromethyl-phenyl)-2,3-dihydro-imidazole-1-carbonyl]-amino}-piperidine-1-carboxylic acid benzyl ester;

5-[2-(4-cyano-phenyl)-2H-pyrazol-3-yl]-4-methyl-2-oxo-3-(3-trifluoromethyl-phenyl)-2,3-dihydro-imidazole-1-carboxylic acid [1-(2,2,2-trifluoro-acetyl)-piperidin-4-yl]-amide;

5-[2-(4-cyano-phenyl)-2H-pyrazol-3-yl]-4-methyl-2-oxo-3-(3-trifluoromethyl-phenyl)-2,3-dihydro-imidazole-1-carboxylic acid ((S)-1-pyridin-4-yl-ethyl)-amide;

5-[2-(4-cyano-phenyl)-2H-pyrazol-3-yl]-4-methyl-2-oxo-3-(3-trifluoromethyl-phenyl)-2,3-dihydro-imidazole-1-carboxylic acid ((R)-1-pyridin-4-yl-ethyl)-amide;

5-[2-(4-cyano-phenyl)-2H-pyrazol-3-yl]-4-methyl-2-oxo-3-(3-trifluoromethyl-phenyl)-2,3-dihydro-imidazole-1-carboxylic acid [3-(4-methoxy-benzyl)-3-azabicyclo[3.1.0]hex-6-yl]-amide;

(trans-4-{[5-[2-(4-cyano-phenyl)-2H-pyrazol-3-yl]-4-methyl-2-oxo-3-(3-trifluoromethyl-phenyl)-2,3-dihydro-imidazole-1-carbonyl]-amino}-cyclohexyl)-carbamic acid tert-butyl ester;

5-[2-(4-cyano-phenyl)-2H-pyrazol-3-yl]-4-methyl-2-oxo-3-(3-trifluoromethyl-phenyl)-2,3-dihydro-imidazole-1-carboxylic acid (trans-4-dimethylamino-cyclohexyl)-amide;

(3aS,5R,6aR)-5-{[5-[2-(4-cyano-phenyl)-2H-pyrazol-3-yl]-4-methyl-2-oxo-3-(3-trifluoromethyl-phenyl)-2,3-dihydro-imidazole-1-carbonyl]-amino}-hexahydro-cyclopenta[c]pyrrole-2-carboxylic acid tert-butyl ester 5-[2-(4-cyano-phenyl)-2H-pyrazol-3-yl]-4-methyl-2-oxo-3-(3-trifluoromethyl-phenyl)-2,3-dihydro-imidazole-1-carboxylic acid [(S)-1-methyl-2-(4-methyl-piperazin-1-yl)-2-oxo-ethyl]-amide;

(3aR,5S,6aS)-5-{[5-[2-(4-cyano-phenyl)-2H-pyrazol-3-yl]-4-methyl-2-oxo-3-(3-trifluoromethyl-phenyl)-2,3-dihydro-imidazole-1-carbonyl]-amino}-hexahydro-cyclopenta[c]pyrrole-2-carboxylic acid tert-butyl ester 5-[2-(4-cyano-phenyl)-2H-pyrazol-3-yl]-4-methyl-2-oxo-3-(3-trifluoromethyl-phenyl)-2,3-dihydro-imidazole-1-carboxylic acid [(S)-1-(1-methyl-piperidin-4-yl-carbamoyl)-ethyl]-amide;

5-[2-(4-cyano-phenyl)-2H-pyrazol-3-yl]-4-methyl-2-oxo-3-(3-trifluoromethyl-phenyl)-2,3-dihydro-imidazole-1-carboxylic acid [(S)-1-(4-dimethylaminomethyl-phenyl)-ethyl]-amide;

5-[2-(4-cyano-phenyl)-2H-pyrazol-3-yl]-4-methyl-2-oxo-3-(3-trifluoromethyl-phenyl)-2,3-dihydro-imidazole-1-carboxylic acid [1-(3-dimethylamino-propionyl)-piperidin-4-yl]-amide;

5-[2-(4-cyano-phenyl)-2H-pyrazol-3-yl]-4-methyl-2-oxo-3-(3-trifluoromethyl-phenyl)-2,3-dihydro-imidazole-1-carboxylic acid [(S)-1-(5-dimethylaminomethyl-oxazol-2-yl)-ethyl]-amide;

5-[2-(4-cyano-phenyl)-2H-pyrazol-3-yl]-4-methyl-2-oxo-3-(3-trifluoromethyl-phenyl)-2,3-dihydro-imidazole-1-carboxylic acid [1-(2-dimethylamino-acetyl)-piperidin-4-yl]-amide;

5-[2-(4-cyano-phenyl)-2H-pyrazol-3-yl]-4-methyl-2-oxo-3-(3-trifluoromethyl-phenyl)-2,3-dihydro-imidazole-1-carboxylic acid {(S)-1-[methyl-(1-methyl-piperidin-4-ylmethyl)-carbamoyl]-ethyl}-amide;

5-[2-(4-cyano-phenyl)-2H-pyrazol-3-yl]-4-methyl-2-oxo-3-(3-trifluoromethyl-phenyl)-2,3-dihydro-imidazole-1-carboxylic acid [(S)-2-(4-dimethylamino-piperidin-1-yl)-1-methyl-2-oxo-ethyl]-amide;

5-[2-(4-cyano-phenyl)-2H-pyrazol-3-yl]-4-methyl-2-oxo-3-(3-trifluoromethyl-phenyl)-2,3-dihydro-imidazole-1-carboxylic acid {(S)-1-[(2-dimethylamino-ethyl)-methyl-carbamoyl]-ethyl}-amide;

5-[2-(4-cyano-phenyl)-2H-pyrazol-3-yl]-4-methyl-2-oxo-3-(3-trifluoromethyl-phenyl)-2,3-dihydro-imidazole-1-carboxylic acid [(S)-1-(5-dimethylaminomethyl-oxazol-2-yl)-2-methyl-propyl]-amide;

5-[2-(4-cyano-phenyl)-2H-pyrazol-3-yl]-4-methyl-2-oxo-3-(3-trifluoromethyl-phenyl)-2,3-dihydro-imidazole-1-carboxylic acid [(S)-1-(5-dimethylaminomethyl-oxazol-2-yl)-propyl]-amide;

5-[2-(4-cyano-phenyl)-2H-pyrazol-3-yl]-4-methyl-2-oxo-3-(3-trifluoromethyl-phenyl)-2,3-dihydro-imidazole-1-carboxylic acid [1-(5-dimethylaminomethyl-oxazol-2-yl)-cyclopropyl]-amide;

5-[2-(4-cyano-phenyl)-2H-pyrazol-3-yl]-4-methyl-2-oxo-3-(3-trifluoromethyl-phenyl)-2,3-dihydro-imidazole-1-carboxylic acid [1-(5-dimethylaminomethyl-oxazol-2-yl)-1-methyl-ethyl]-amide;

5-[2-(4-cyano-phenyl)-2H-pyrazol-3-yl]-4-methyl-2-oxo-3-(3-trifluoromethyl-phenyl)-2,3-dihydro-imidazole-1-carboxylic acid [1-(2-dimethylamino-acetyl)-4-methyl-piperidin-4-yl]-amide;

5-[2-(4-cyano-phenyl)-2H-pyrazol-3-yl]-4-methyl-2-oxo-3-(3-trifluoromethyl-phenyl)-2,3-dihydro-imidazole-1-carboxylic acid [trans-4-(2-dimethylamino-acetylamino)-cyclohexyl]-amide;

5-[2-(4-cyano-phenyl)-2H-pyrazol-3-yl]-4-methyl-2-oxo-3-(3-trifluoromethyl-phenyl)-2,3-dihydro-imidazole-1-carboxylic acid {trans-4-[(2-dimethylamino-acetylamino)-methyl]-cyclohexyl}-amide;

5-[2-(4-cyano-phenyl)-2H-pyrazol-3-yl]-4-methyl-2-oxo-3-(3-trifluoromethyl-phenyl)-2,3-dihydro-imidazole-1-carboxylic acid {(S)-1-[methyl-(1-methyl-piperidin-4-yl)-carbamoyl]-ethyl}-amide;

(trans-4-{[5-[2-(4-cyano-phenyl)-2H-pyrazol-3-yl]-4-methyl-2-oxo-3-(3-trifluoromethyl-phenyl)-2,3-dihydro-imidazole-1-carbonyl]-amino}-cyclohexylmethyl)-trimethyl-ammonium benzene sulfonate;

benzyl-(trans-4-{[5-[2-(4-cyano-phenyl)-2H-pyrazol-3-yl]-4-methyl-2-oxo-3-(3-trifluoromethyl-phenyl)-2,3-dihydro-imidazole-1-carbonyl]-amino}-cyclohexylmethyl)-dimethyl-ammonium bromide;

(trans-4-{[5-[2-(4-cyano-phenyl)-2H-pyrazol-3-yl]-4-methyl-2-oxo-3-(3-trifluoromethyl-phenyl)-2,3-dihydro-imidazole-1-carbonyl]-amino}-cyclohexylmethyl)-ethyl-dimethyl-ammonium benzene sulfonate;

4-{[5-[2-(4-cyano-phenyl)-2H-pyrazol-3-yl]-4-methyl-2-oxo-3-(3-trifluoromethyl-phenyl)-2,3-dihydro-imidazole-1-carbonyl]-amino}-1,1-dimethyl-piperidinium benzenesulfonate;

(R)-3-{[5-[2-(4-cyano-phenyl)-2H-pyrazol-3-yl]-4-methyl-2-oxo-3-(3-trifluoromethyl-phenyl)-2,3-dihydro-imidazole-1-carbonyl]-amino}-1,1-dimethyl-pyrrolidinium benzenesulfonate;

(S)-3-{[5-[2-(4-cyano-phenyl)-2H-pyrazol-3-yl]-4-methyl-2-oxo-3-(3-trifluoromethyl-phenyl)-2,3-dihydro-imidazole-1-carbonyl]-amino}-1,1-dimethyl-pyrrolidinium benzenesulfonate;

4-(1-{[5-[2-(4-cyano-phenyl)-2H-pyrazol-3-yl]-4-methyl-2-oxo-3-(3-trifluoromethyl-phenyl)-2,3-dihydro-imidazole-1-carbonyl]-amino}-ethyl)-1,1-dimethyl-piperidinium benzene sulfonate;

(1S,3R,5R)-3-{[5-[2-(4-cyano-phenyl)-2H-pyrazol-3-yl]-4-methyl-2-oxo-3-(3-trifluoromethyl-phenyl)-2,3-dihydro-imidazole-1-carbonyl]-amino}-8,8-dimethyl-8-azonia-bicyclo[3.2.1]octane benzene sulfonate;

(3 aS,5R,6aR)-5-{[5-[2-(4-cyano-phenyl)-2H-pyrazol-3-yl]-4-methyl-2-oxo-3-(3-trifluoromethyl-phenyl)-2,3-dihydro-imidazole-1-carbonyl]-amino}-2,2-dimethyl-octahydro-cyclopenta[c]pyrrolium benzene sulfonate;

4-((S)-1-{[5-[2-(4-cyano-phenyl)-2H-pyrazol-3-yl]-4-methyl-2-oxo-3-(3-trifluoromethyl-phenyl)-2,3-dihydro-imidazole-1-carbonyl]-amino}-ethyl)-1-methyl-pyridinium benzene sulfonate;

(1R,3S,5S)-3-{[5-[2-(4-cyano-phenyl)-2H-pyrazol-3-yl]-4-methyl-2-oxo-3-(3-trifluoromethyl-phenyl)-2,3-dihydro-imidazole-1-carbonyl]-amino}-8,8-dimethyl-8-azonia-bicyclo[3.2.1]octane benzene sulfonate;

4-{[5-[2-(4-cyano-phenyl)-2H-pyrazol-3-yl]-4-methyl-2-oxo-3-(3-trifluoromethyl-phenyl)-2,3-dihydro-imidazole-1-carbonyl]-amino}-1,1-diethyl-piperidinium benzene sulfonate;

(trans-4-{[5-[2-(4-cyano-phenyl)-2H-pyrazol-3-yl]-4-methyl-2-oxo-3-(3-trifluoromethyl-phenyl)-2,3-dihydro-imidazole-1-carbonyl]-amino}-cyclohexyl)-trimethyl-ammonium benzene sulfonate;

4-((S)-1-{[5-[2-(4-cyano-phenyl)-2H-pyrazol-3-yl]-4-methyl-2-oxo-3-(3-trifluoromethyl-phenyl)-2,3-dihydro-imidazole-1-carbonyl]-amino}-ethyl)-1-ethyl-pyridinium benzene sulfonate;

benzyl-(trans-4-{[5-[2-(4-cyano-phenyl)-2H-pyrazol-3-yl]-4-methyl-2-oxo-3-(3-trifluoromethyl-phenyl)-2,3-dihydro-imidazole-1-carbonyl]-amino}-cyclohexyl)-dimethyl-ammonium bromide;

(trans-4-{[5-[2-(4-cyano-phenyl)-2H-pyrazol-3-yl]-4-methyl-2-oxo-3-(3-trifluoromethyl-phenyl)-2,3-dihydro-imidazole-1-carbonyl]-amino}-cyclohexyl)-ethyl-dimethyl-ammonium benzene sulfonate;

(cis-4-{[5-[2-(4-cyano-phenyl)-2H-pyrazol-3-yl]-4-methyl-2-oxo-3-(3-trifluoromethyl-phenyl)-2,3-dihydro-imidazole-1-carbonyl]-amino}-cyclohexyl)-trimethyl-ammonium benzene sulfonate;

benzyl-(cis-4-{[5-[2-(4-cyano-phenyl)-2H-pyrazol-3-yl]-4-methyl-2-oxo-3-(3-trifluoromethyl-phenyl)-2,3-dihydro-imidazole-1-carbonyl]-amino}-cyclohexyl)-dimethyl-ammonium bromide;

4-(1-{[5-[2-(4-cyano-phenyl)-2H-pyrazol-3-yl]-4-methyl-2-oxo-3-(3-trifluoromethyl-phenyl)-2,3-dihydro-imidazole-1-carbonyl]-amino}-1-methyl-ethyl)-1-methyl-pyridinium benzene sulfonate;

(cis-4-{[5-[2-(4-cyano-phenyl)-2H-pyrazol-3-yl]-4-methyl-2-oxo-3-(3-trifluoromethyl-phenyl)-2,3-dihydro-imidazole-1-carbonyl]-amino}-cyclohexyl)-ethyl-dimethyl-ammonium benzene sulfonate;

1-benzyl-4-((S)-2-{[5-[2-(4-cyano-phenyl)-2H-pyrazol-3-yl]-4-methyl-2-oxo-3-(3-trifluoromethyl-phenyl)-2,3-dihydro-imidazole-1-carbonyl]-amino}-propionyl)-1-methyl-piperazin-1-ium bromide;

4-((S)-2-{[5-[2-(4-cyano-phenyl)-2H-pyrazol-3-yl]-4-methyl-2-oxo-3-(3-trifluoromethyl-phenyl)-2,3-dihydro-imidazole-1-carbonyl]-amino}-propionyl)-1,1-dimethyl-piperazin-1-ium benzene sulfonate;

2-{[5-[2-(4-cyano-phenyl)-2H-pyrazol-3-yl]-4-methyl-2-oxo-3-(3-trifluoromethyl-phenyl)-2,3-dihydro-imidazole-1-carbonyl]-amino}-7,7-dimethyl-7-azonia-spiro[3.5]nonane benzene sulfonate;

4-((R)-1-{[5-[2-(4-cyano-phenyl)-2H-pyrazol-3-yl]-4-methyl-2-oxo-3-(3-trifluoromethyl-phenyl)-2,3-dihydro-imidazole-1-carbonyl]-amino}-ethyl)-1-methyl-pyridinium benzene sulfonate;

(cis-4-{[5-[2-(4-cyano-phenyl)-2H-pyrazol-3-yl]-4-methyl-2-oxo-3-(3-trifluoromethyl-phenyl)-2,3-dihydro-imidazole-1-carbonyl]-amino}-cyclohexylmethyl)-trimethyl-ammonium benzene sulfonate;

benzyl-(cis-4-{[5-[2-(4-cyano-phenyl)-2H-pyrazol-3-yl]-4-methyl-2-oxo-3-(3-trifluoromethyl-phenyl)-2,3-dihydro-imidazole-1-carbonyl]-amino}-cyclohexylmethyl)-dimethyl-ammonium bromide;

(cis-4-{[5-[2-(4-cyano-phenyl)-2H-pyrazol-3-yl]-4-methyl-2-oxo-3-(3-trifluoromethyl-phenyl)-2,3-dihydro-imidazole-1-carbonyl]-amino}-cyclohexylmethyl)-ethyl-dimethyl-ammonium benzene sulfonate;

(3aR,5S,6aS)-5-{[5-[2-(4-cyano-phenyl)-2H-pyrazol-3-yl]-4-methyl-2-oxo-3-(3-trifluoromethyl-phenyl)-2,3-dihydro-imidazole-1-carbonyl]-amino}-2,2-dimethyl-octahydro-cyclopenta[c]pyrrolium benzene sulfonate;

4-((S)-2-{[5-[2-(4-cyano-phenyl)-2H-pyrazol-3-yl]-4-methyl-2-oxo-3-(3-trifluoromethyl-phenyl)-2,3-dihydro-imidazole-1-carbonyl]-amino}-propionylamino)-1,1-dimethyl-piperidinium benzene sulfonate;

[4-((S)-1-{[5-[2-(4-cyano-phenyl)-2H-pyrazol-3-yl]-4-methyl-2-oxo-3-(3-trifluoromethyl-phenyl)-2,3-dihydro-imidazole-1-carbonyl]-amino}-ethyl)-benzyl]-trimethyl-ammonium benzene sulfonate;

[4-((S)-1-{[5-[2-(4-cyano-phenyl)-2H-pyrazol-3-yl]-4-methyl-2-oxo-3-(3-trifluoromethyl-phenyl)-2,3-dihydro-imidazole-1-carbonyl]-amino}-ethyl)-benzyl]-trimethyl-ammonium benzene sulfonate;

[5-((S)-1-{[5-[2-(4-cyano-phenyl)-2H-pyrazol-3-yl]-4-methyl-2-oxo-3-(3-trifluoromethyl-phenyl)-2,3-dihydro-imidazole-1-carbonyl]-amino}-ethyl)-[1,2,4]oxadiazol-3-ylmethyl]-trimethyl-ammonium benzene sulfonate;

[2-(4-{[5-[2-(4-cyano-phenyl)-2H-pyrazol-3-yl]-4-methyl-2-oxo-3-(3-trifluoromethyl-phenyl)-2,3-dihydro-imidazole-1-carbonyl]-amino}-piperidin-1-yl)-2-oxo-ethyl]-trimethyl-ammonium benzene sulfonate;

4-{[(((S)-2-{[5-[2-(4-cyano-phenyl)-2H-pyrazol-3-yl]-4-methyl-2-oxo-3-(3-trifluoromethyl-phenyl)-2,3-dihydro-imidazole-1-carbonyl]-amino}-propionyl)-methyl-amino]-methyl}-1,1-dimethyl-piperidinium benzene sulfonate;

[5-((S)-1-{[5-[2-(4-cyano-phenyl)-2H-pyrazol-3-yl]-4-methyl-2-oxo-3-(3-trifluoromethyl-phenyl)-2,3-dihydro-imidazole-1-carbonyl]-amino}-ethyl)-[1,3,4]oxadiazol-2-ylmethyl]-trimethyl-ammonium benzene sulfonate;

[2-((S)-1-{[5-[2-(4-cyano-phenyl)-2H-pyrazol-3-yl]-4-methyl-2-oxo-3-(3-trifluoromethyl-phenyl)-2,3-dihydro-imidazole-1-carbonyl]-amino}-ethyl)-oxazol-5-ylmethyl]-trimethyl-ammonium benzene sulfonate;

[3-(4-{[5-[2-(4-cyano-phenyl)-2H-pyrazol-3-yl]-4-methyl-2-oxo-3-(3-trifluoromethyl-phenyl)-2,3-dihydro-imidazole-1-carbonyl]-amino}-piperidin-1-yl)-3-oxo-propyl]-trimethyl-ammonium benzene sulfonate;

9-{[5-[2-(4-cyano-phenyl)-2H-pyrazol-3-yl]-4-methyl-2-oxo-3-(3-trifluoromethyl-phenyl)-2,3-dihydro-imidazole-1-carbonyl]-amino}-3,3-dimethyl-3-azonia-spiro[5.5]undecane benzene sulfonate;

(cis-3-{[5-[2-(4-cyano-phenyl)-2H-pyrazol-3-yl]-4-methyl-2-oxo-3-(3-trifluoromethyl-phenyl)-2,3-dihydro-imidazole-1-carbonyl]-amino}-cyclobutylmethyl)-trimethyl-ammonium benzene sulfonate;

(trans-3-{[5-[2-(4-cyano-phenyl)-2H-pyrazol-3-yl]-4-methyl-2-oxo-3-(3-trifluoromethyl-phenyl)-2,3-dihydro-imidazole-1-carbonyl]-amino}-cyclobutylmethyl)-trimethyl-ammonium benzene sulfonate;

[1-((S)-2-{[5-[2-(4-cyano-phenyl)-2H-pyrazol-3-yl]-4-methyl-2-oxo-3-(3-trifluoromethyl-phenyl)-2,3-dihydro-imidazole-1-carbonyl]-amino}-propionyl)-piperidin-4-yl]-trimethyl-ammonium benzene sulfonate;

benzyl-[1-((S)-2-{[5-[2-(4-cyano-phenyl)-2H-pyrazol-3-yl]-4-methyl-2-oxo-3-(3-trifluoromethyl-phenyl)-2,3-dihydro-imidazole-1-carbonyl]-amino}-propionyl)-piperidin-4-yl]-dimethyl-ammonium bromide;

{2-[((S)-2-{[5-[2-(4-cyano-phenyl)-2H-pyrazol-3-yl]-4-methyl-2-oxo-3-(3-trifluoromethyl-phenyl)-2,3-dihydro-imidazole-1-carbonyl]-amino}-propionyl)-methyl-amino]-ethyl}-trimethyl-ammonium benzene sulfonate;

(trans-4-{[5-[2-(4-cyano-phenyl)-2H-pyrazol-3-yl]-4-methyl-2-oxo-3-(3-trifluoromethyl-phenyl)-2,3-dihydro-imidazole-1-carbonyl]-amino}-cyclohexyl)-dimethyl-[1,2,4]oxadiazol-3-ylmethyl-ammonium chloride;

[2-((S)-1-{[5-[2-(4-cyano-phenyl)-2H-pyrazol-3-yl]-4-methyl-2-oxo-3-(3-trifluoromethyl-phenyl)-2,3-dihydro-imidazole-1-carbonyl]-amino}-2-methyl-propyl)-oxazol-5-ylmethyl]-trimethyl-ammonium benzene sulfonate;

[2-((S)-1-{[5-[2-(4-cyano-phenyl)-2H-pyrazol-3-yl]-4-methyl-2-oxo-3-(3-trifluoromethyl-phenyl)-2,3-dihydro-imidazole-1-carbonyl]-amino}-propyl)-oxazol-5-ylmethyl]-trimethyl-ammonium benzene sulfonate;

(4-{[5-[2-(4-cyano-phenyl)-2H-pyrazol-3-yl]-4-methyl-2-oxo-3-(3-trifluoromethyl-phenyl)-2,3-dihydro-imidazole-1-carbonyl]-amino}-cyclohexyl)-dimethyl-(5-methyl-isoxazol-3-ylmethyl)-ammonium chloride;

(4-{[5-[2-(4-cyano-phenyl)-2H-pyrazol-3-yl]-4-methyl-2-oxo-3-(3-trifluoromethyl-phenyl)-2,3-dihydro-imidazole-1-carbonyl]-amino}-cyclohexyl)-(2,5-dimethyl-2H-pyrazol-3-ylmethyl)-dimethyl-ammonium chloride;

{2-[(trans-4-{[5-[2-(4-cyano-phenyl)-2H-pyrazol-3-yl]-4-methyl-2-oxo-3-(3-trifluoromethyl-phenyl)-2,3-dihydro-imidazole-1-carbonyl]-amino}-cyclohexanecarbonyl)-amino]-ethyl}-trimethyl-ammonium benzene sulfonate

[2-(1-{[5-[2-(4-cyano-phenyl)-2H-pyrazol-3-yl]-4-methyl-2-oxo-3-(3-trifluoromethyl-phenyl)-2,3-dihydro-imidazole-1-carbonyl]-amino}-1-methyl-ethyl)-oxazol-5-ylmethyl]-trimethyl-ammonium benzene sulfonate;

[2-(1-{[5-[2-(4-cyano-phenyl)-2H-pyrazol-3-yl]-4-methyl-2-oxo-3-(3-trifluoromethyl-phenyl)-2,3-dihydro-imidazole-1-carbonyl]-amino}-cyclopropyl)-oxazol-5-ylmethyl]-trimethyl-ammonium benzene sulfonate;

{2-[(cis-4-{[5-[2-(4-cyano-phenyl)-2H-pyrazol-3-yl]-4-methyl-2-oxo-3-(3-trifluoromethyl-phenyl)-2,3-dihydro-imidazole-1-carbonyl]-amino}-cyclohexanecarbonyl)-amino]-ethyl}-trimethyl-ammonium benzene sulfonate;

{2-[(cis-3-{[5-[2-(4-cyano-phenyl)-2H-pyrazol-3-yl]-4-methyl-2-oxo-3-(3-trifluoromethyl-phenyl)-2,3-dihydro-imidazole-1-carbonyl]-amino}-cyclobutanecarbonyl)-amino]ethyl}-trimethyl-ammonium benzene sulfonate;

[2-(trans-4-{[5-[2-(4-cyano-phenyl)-2H-pyrazol-3-yl]-4-methyl-2-oxo-3-(3-trifluoromethyl-phenyl)-2,3-dihydro-imidazole-1-carbonyl]-amino}-cyclohexanecarbonyloxy)-ethyl]-trimethyl-ammonium benzene sulfonate;

{2-[(trans-3-{[5-[2-(4-cyano-phenyl)-2H-pyrazol-3-yl]-4-methyl-2-oxo-3-(3-trifluoromethyl-phenyl)-2,3-dihydro-imidazole-1-carbonyl]-amino}-cyclobutanecarbonyl)-amino]-ethyl}-trimethyl-ammonium benzene sulfonate;

[2-(4-{[5-[2-(4-cyano-phenyl)-2H-pyrazol-3-yl]-4-methyl-2-oxo-3-(3-trifluoromethyl-phenyl)-2,3-dihydro-imidazole-1-carbonyl]-amino)-4-methyl-piperidin-1-yl)-2-oxo-ethyl]-trimethyl-ammonium benzene sulfonate;

±[2-(1-{[5-[2-(4-cyano-phenyl)-2H-pyrazol-3-yl]-4-methyl-2-oxo-3-(3-trifluoromethyl-phenyl)-2,3-dihydro-imidazole-1-carbonyl]-amino}-ethyl)-thiazol-4-ylmethyl]-trimethyl-ammonium benzene sulfonate;

{[(trans-4-{[5-[2-(4-cyano-phenyl)-2H-pyrazol-3-yl]-4-methyl-2-oxo-3-(3-trifluoromethyl-phenyl)-2,3-dihydro-imidazole-1-carbonyl]-amino}-cyclohexylmethyl)-carbamoyl]-methyl}-trimethyl-ammonium benzene sulfonate;

[(trans-4-{[5-[2-(4-cyano-phenyl)-2H-pyrazol-3-yl]-4-methyl-2-oxo-3-(3-trifluoromethyl-phenyl)-2,3-dihydro-imidazole-1-carbonyl]-amino}-cyclohexylcarbamoyl)-methyl]-trimethyl-ammonium benzene sulfonate;

[1-(trans-4-{[5-[2-(4-cyano-phenyl)-2H-pyrazol-3-yl]-4-methyl-2-oxo-3-(3-trifluoromethyl-phenyl)-2,3-dihydro-imidazole-1-carbonyl]-amino}-cyclohexanecarbonyl)-piperidin-4-yl]-trimethyl-ammonium benzene sulfonate;

{2-[(trans-4-{[5-[2-(4-cyano-phenyl)-2H-pyrazol-3-yl]-4-methyl-2-oxo-3-(3-trifluoromethyl-phenyl)-2,3-dihydro-imidazole-1-carbonyl]-amino}-cyclohexanecarbonyl)-methyl-amino]-ethyl}-trimethyl-ammonium benzene sulfonate;

4-[(trans-4-{[5-[2-(4-cyano-phenyl)-2H-pyrazol-3-yl]-4-methyl-2-oxo-3-(3-trifluoromethyl-phenyl)-2,3-dihydro-imidazole-1-carbonyl]-amino}-cyclohexanecarbonyl)-amino]-1,1-dimethyl-piperidinium benzene sulfonate;

4-[((S)-2-{[5-[2-(4-cyano-phenyl)-2H-pyrazol-3-yl]-4-methyl-2-oxo-3-(3-trifluoromethyl-phenyl)-2,3-dihydro-imidazole-1-carbonyl]-amino}-propionyl)-methyl-amino]-1,1-dimethyl-piperidinium benzene sulfonate;

{2-[(4-{[5-[2-(4-cyano-phenyl)-2H-pyrazol-3-yl]-4-methyl-2-oxo-3-(3-trifluoromethyl-phenyl)-2,3-dihydro-imidazole-1-carbonyl]-amino}-piperidine-1-carbonyl)-amino]-ethyl}-trimethyl-ammonium benzene sulfonate;

[2-(4-{[5-[2-(4-cyano-phenyl)-2H-pyrazol-3-yl]-4-methyl-2-oxo-3-(3-trifluoromethyl-phenyl)-2,3-dihydro-imidazole-1-carbonyl]-amino}-piperidine-1-carbonyloxy)-ethyl]-trimethyl-ammonium benzene sulfonate;

[2-(4-{[1-(4-cyano-phenyl)-5'-methyl-2'-oxo-1'-(3-trifluoromethyl-phenyl)-1',2'-dihydro-1H-[2,4']biimidazolyl-3'-carbonyl]-amino}-piperidin-1-yl)-2-oxo-ethyl]-trimethyl-ammonium benzene sulfonate.

10. A pharmaceutical composition, comprising a compound or salt according to claim 1 and a pharmaceutically acceptable carrier or excipient.

11. A pharmaceutical composition according to claim 10 which is adapted for oral administration or administration by the pulmonary route.

12. A method of treatment of a disease or condition in which HNE is implicated, comprising administering to a subject in need thereof an effective amount of a compound or salt according to claim 1.

13. A method according to claim 12, wherein said disease or condition is chronic obstructive pulmonary disease, bronchiectasis, chronic bronchitis, lung fibrosis, pneumonia, acute respiratory distress syndrome, pulmonary emphysema, smoking-induced emphysema, or cystic fibrosis.

14. A method according to claim 12, wherein said disease or condition is asthma, rhinitis, psoriasis, atopic dermatitis, non-atopic dermatitis, Crohn's disease, ulcerative colitis, or irritable bowel disease.

* * * * *